(12) United States Patent
Ku et al.

(10) Patent No.: US 9,179,974 B2
(45) Date of Patent: Nov. 10, 2015

(54) HELICAL PUSH WIRE ELECTRODE

(71) Applicant: Medtronic Ardian Luxembourg S.a.r.l., Luxembourg (LU)

(72) Inventors: Vincent W. Ku, Mountain View, CA (US); Andrew E. Wu, Mountain View, CA (US)

(73) Assignee: Medtronic Ardian Luxembourg S.a.r.l., Luxembourg (LU)

(*) Notice: Subject to any disclaimer, the term of this patent is extended or adjusted under 35 U.S.C. 154(b) by 145 days.

(21) Appl. No.: 13/870,277

(22) Filed: Apr. 25, 2013

(65) Prior Publication Data

US 2014/0276748 A1    Sep. 18, 2014

Related U.S. Application Data

(60) Provisional application No. 61/801,264, filed on Mar. 15, 2013.

(51) Int. Cl.
*A61B 18/14* (2006.01)
*A61B 18/18* (2006.01)
*A61B 18/00* (2006.01)

(52) U.S. Cl.
CPC .............. *A61B 18/18* (2013.01); *A61B 18/1492* (2013.01); *A61B 2018/00214* (2013.01); *A61B 2018/00267* (2013.01); *A61B 2018/00511* (2013.01); *A61B 2018/00577* (2013.01); *A61B 2018/144* (2013.01); *A61B 2018/1435* (2013.01)

(58) Field of Classification Search
CPC ........... A61B 2018/00267; A61B 2018/00511; A61B 2018/00577; A61B 2018/1435
USPC ............................................. 606/41
See application file for complete search history.

(56) References Cited

U.S. PATENT DOCUMENTS

| 3,935,348 | A | 1/1976 | Smith |
| 4,154,246 | A | 5/1979 | LeVeen |
| 4,169,464 | A | 10/1979 | Obrez |
| 4,419,819 | A | 12/1983 | Dickhudt et al. |
| 4,602,624 | A | 7/1986 | Naples et al. |

(Continued)

FOREIGN PATENT DOCUMENTS

| CN | 201469401 | 5/2010 |
| CN | 102198015 | 9/2011 |

(Continued)

OTHER PUBLICATIONS

International Search Report, PCT/US02/07661, Aug. 13, 2002, 5 Pages.

(Continued)

*Primary Examiner* — Lee S Cohen

(57) ABSTRACT

Helical push wire electrodes are provided. The electrodes may create a continuous helical lesion. One or more electrodes may wind around a support section and create a set of helixes having fixed ends and hitches. Pushing or pulling an end of the electrode transforms the electrodes between a delivery configuration and a deployed configuration such that the set of helixes expand or contract axially. Different portions of the electrodes may be surrounded by sleeves. The sleeves may regulate how the wires transform and provide insulation. Various insulation configurations of the electrodes may provide creations of discrete lesions, efficient energy delivery and reduced power consumption.

12 Claims, 19 Drawing Sheets

(56) References Cited

U.S. PATENT DOCUMENTS

| | | |
|---|---|---|
| 4,649,936 A | 3/1987 | Ungar et al. |
| 4,660,571 A | 4/1987 | Hess et al. |
| 4,706,671 A | 11/1987 | Weinrib |
| 4,709,698 A | 12/1987 | Johnston et al. |
| 4,764,504 A | 8/1988 | Johnson et al. |
| 4,781,682 A | 11/1988 | Patel |
| 4,796,643 A | 1/1989 | Nakazawa et al. |
| 4,819,661 A | 4/1989 | Heil, Jr. et al. |
| 4,834,724 A | 5/1989 | Geiss et al. |
| 4,860,769 A | 8/1989 | Fogarty et al. |
| 4,921,484 A | 5/1990 | Hillstead |
| 4,957,118 A | 9/1990 | Erlebacher |
| 4,961,377 A | 10/1990 | Bando et al. |
| 4,976,711 A | 12/1990 | Parins et al. |
| 4,995,868 A | 2/1991 | Brazier |
| 5,002,067 A | 3/1991 | Berthelsen et al. |
| 5,011,488 A | 4/1991 | Ginsburg |
| 5,016,808 A | 5/1991 | Heil, Jr. et al. |
| 5,052,998 A | 10/1991 | Zimmon |
| 5,054,501 A | 10/1991 | Chuttani et al. |
| 5,071,407 A | 12/1991 | Termin et al. |
| 5,133,365 A | 7/1992 | Heil, Jr. et al. |
| 5,156,151 A | 10/1992 | Imran |
| 5,163,928 A | 11/1992 | Hobbs et al. |
| 5,188,602 A | 2/1993 | Nichols |
| 5,188,619 A | 2/1993 | Myers |
| 5,209,723 A | 5/1993 | Twardowski et al. |
| 5,228,442 A | 7/1993 | Imran |
| 5,239,999 A | 8/1993 | Imran |
| 5,249,585 A | 10/1993 | Turner et al. |
| 5,263,492 A | 11/1993 | Voyce |
| 5,263,493 A | 11/1993 | Avitall |
| 5,279,299 A | 1/1994 | Imran |
| 5,296,510 A | 3/1994 | Yamada et al. |
| 5,300,068 A | 4/1994 | Rosar et al. |
| 5,300,099 A | 4/1994 | Rudie |
| 5,308,323 A | 5/1994 | Sogawa et al. |
| 5,318,525 A | 6/1994 | West et al. |
| 5,324,284 A | 6/1994 | Imran |
| 5,327,905 A | 7/1994 | Avitall |
| 5,345,031 A | 9/1994 | Schwartz et al. |
| 5,345,936 A | 9/1994 | Pomeranz et al. |
| 5,354,297 A | 10/1994 | Avitall |
| 5,358,514 A | 10/1994 | Schulman et al. |
| 5,365,926 A | 11/1994 | Desai |
| 5,368,591 A | 11/1994 | Lennox et al. |
| 5,383,856 A | 1/1995 | Bersin |
| 5,387,233 A | 2/1995 | Alferness et al. |
| 5,397,304 A | 3/1995 | Truckai |
| 5,397,339 A | 3/1995 | Desai |
| 5,405,374 A | 4/1995 | Stein |
| 5,411,546 A | 5/1995 | Bowald et al. |
| 5,423,744 A | 6/1995 | Gencheff et al. |
| 5,425,364 A | 6/1995 | Imran |
| 5,462,545 A | 10/1995 | Wang et al. |
| 5,476,495 A | 12/1995 | Kordis et al. |
| 5,476,498 A | 12/1995 | Ayers |
| 5,484,400 A | 1/1996 | Edwards et al. |
| 5,487,385 A | 1/1996 | Avitall |
| 5,487,757 A | 1/1996 | Truckai et al. |
| 5,497,774 A | 3/1996 | Swartz et al. |
| 5,507,743 A | 4/1996 | Edwards et al. |
| 5,509,909 A | 4/1996 | Moy |
| 5,523,092 A | 6/1996 | Hanson et al. |
| 5,529,820 A | 6/1996 | Nomi et al. |
| 5,545,193 A | 8/1996 | Fleischman et al. |
| 5,545,200 A | 8/1996 | West et al. |
| 5,545,475 A | 8/1996 | Korleski |
| 5,549,661 A | 8/1996 | Kordis et al. |
| 5,564,440 A | 10/1996 | Swartz et al. |
| 5,571,147 A | 11/1996 | Sluijter et al. |
| 5,575,766 A | 11/1996 | Swartz et al. |
| 5,575,810 A | 11/1996 | Swanson et al. |
| 5,582,609 A | 12/1996 | Swanson et al. |
| 5,588,964 A | 12/1996 | Imran et al. |
| 5,591,132 A | 1/1997 | Carrie |
| 5,599,345 A | 2/1997 | Edwards et al. |
| 5,609,151 A | 3/1997 | Mulier et al. |
| 5,617,854 A | 4/1997 | Munsif |
| 5,626,576 A | 5/1997 | Janssen |
| 5,628,775 A | 5/1997 | Jackson et al. |
| 5,636,634 A | 6/1997 | Kordis et al. |
| 5,637,090 A | 6/1997 | McGee et al. |
| 5,642,736 A | 7/1997 | Avitall |
| 5,672,174 A | 9/1997 | Gough et al. |
| 5,676,662 A | 10/1997 | Fleischhacker et al. |
| 5,680,860 A | 10/1997 | Imran |
| 5,681,280 A | 10/1997 | Rusk et al. |
| 5,687,723 A | 11/1997 | Avitall |
| 5,688,266 A | 11/1997 | Edwards et al. |
| 5,690,611 A | 11/1997 | Swartz et al. |
| 5,697,928 A | 12/1997 | Walcott et al. |
| 5,700,282 A | 12/1997 | Zabara |
| 5,707,400 A | 1/1998 | Terry, Jr. et al. |
| 5,709,874 A | 1/1998 | Hanson et al. |
| 5,715,818 A | 2/1998 | Swartz et al. |
| 5,716,410 A | 2/1998 | Wang et al. |
| 5,722,401 A | 3/1998 | Pietroski et al. |
| 5,725,512 A | 3/1998 | Swartz et al. |
| 5,727,555 A | 3/1998 | Chait |
| 5,730,127 A | 3/1998 | Avitall |
| 5,730,741 A | 3/1998 | Horzewski et al. |
| 5,755,760 A | 5/1998 | Maguire et al. |
| 5,755,761 A | 5/1998 | Obino |
| 5,772,590 A | 6/1998 | Webster, Jr. |
| 5,807,395 A | 9/1998 | Mulier et al. |
| 5,814,028 A | 9/1998 | Swartz et al. |
| 5,823,955 A | 10/1998 | Kuck et al. |
| 5,827,242 A | 10/1998 | Follmer et al. |
| 5,827,268 A | 10/1998 | Laufer |
| 5,842,984 A | 12/1998 | Avitall |
| 5,846,355 A | 12/1998 | Spencer et al. |
| 5,860,920 A | 1/1999 | McGee et al. |
| 5,860,974 A | 1/1999 | Abele |
| 5,865,787 A | 2/1999 | Shapland et al. |
| 5,865,815 A | 2/1999 | Tihon |
| 5,871,523 A | 2/1999 | Fleischman et al. |
| 5,871,531 A | 2/1999 | Struble |
| 5,873,865 A | 2/1999 | Horzewski et al. |
| 5,879,295 A | 3/1999 | Li et al. |
| 5,882,346 A | 3/1999 | Pomeranz et al. |
| 5,893,885 A | 4/1999 | Webster et al. |
| 5,910,129 A | 6/1999 | Koblish et al. |
| 5,931,848 A | 8/1999 | Saadat |
| 5,938,694 A | 8/1999 | Jaraczewski et al. |
| 5,941,823 A | 8/1999 | Chait |
| 5,944,710 A | 8/1999 | Dev et al. |
| 5,951,471 A | 9/1999 | de la Rama et al. |
| 5,954,719 A | 9/1999 | Chen et al. |
| 5,957,961 A | 9/1999 | Maguire et al. |
| 5,968,085 A | 10/1999 | Morris et al. |
| 5,972,019 A | 10/1999 | Engelson et al. |
| 5,972,026 A | 10/1999 | Laufer et al. |
| 5,980,516 A | 11/1999 | Mulier et al. |
| 5,983,141 A | 11/1999 | Sluijter et al. |
| 5,993,462 A | 11/1999 | Pomeranz et al. |
| 5,997,526 A | 12/1999 | Giba et al. |
| 6,004,269 A | 12/1999 | Crowley et al. |
| 6,004,348 A | 12/1999 | Banas et al. |
| 6,009,877 A | 1/2000 | Edwards |
| 6,012,457 A | 1/2000 | Lesh |
| 6,032,077 A | 2/2000 | Pomeranz |
| 6,042,578 A | 3/2000 | Dinh et al. |
| 6,048,329 A | 4/2000 | Thompson et al. |
| 6,064,902 A | 5/2000 | Haissaguerre et al. |
| 6,066,134 A | 5/2000 | Eggers et al. |
| 6,071,729 A | 6/2000 | Jeffries et al. |
| 6,074,339 A | 6/2000 | Gambale et al. |
| 6,074,361 A | 6/2000 | Jacobs |
| 6,074,378 A | 6/2000 | Mouri et al. |
| 6,076,012 A | 6/2000 | Swanson et al. |
| 6,078,840 A | 6/2000 | Stokes |
| 6,078,841 A | 6/2000 | Kuzma |
| 6,090,104 A | 7/2000 | Webster, Jr. |

(56) References Cited

U.S. PATENT DOCUMENTS

| | | |
|---|---|---|
| 6,094,596 A | 7/2000 | Morgan |
| 6,096,036 A | 8/2000 | Bowe et al. |
| 6,099,524 A | 8/2000 | Lipson et al. |
| 6,106,522 A | 8/2000 | Fleischman et al. |
| 6,117,101 A | 9/2000 | Diederich et al. |
| 6,123,703 A | 9/2000 | Tu et al. |
| 6,125,302 A | 9/2000 | Kuzma |
| 6,129,750 A | 10/2000 | Tockman et al. |
| 6,132,456 A | 10/2000 | Sommer et al. |
| 6,135,999 A | 10/2000 | Fanton et al. |
| 6,146,381 A | 11/2000 | Bowe et al. |
| 6,149,620 A | 11/2000 | Baker et al. |
| 6,161,048 A | 12/2000 | Sluijter et al. |
| 6,161,049 A | 12/2000 | Rudie et al. |
| 6,164,283 A | 12/2000 | Lesh |
| 6,190,356 B1 | 2/2001 | Bersin |
| 6,214,002 B1 | 4/2001 | Fleischman et al. |
| 6,219,577 B1 | 4/2001 | Brown, III et al. |
| 6,223,070 B1 | 4/2001 | Chait |
| 6,224,592 B1 | 5/2001 | Eggers et al. |
| 6,228,109 B1 | 5/2001 | Tu et al. |
| 6,246,912 B1 | 6/2001 | Sluijter et al. |
| 6,270,496 B1 | 8/2001 | Bowe et al. |
| 6,273,886 B1 | 8/2001 | Edwards et al. |
| 6,280,441 B1 | 8/2001 | Ryan |
| 6,283,951 B1 | 9/2001 | Flaherty et al. |
| 6,292,695 B1 * | 9/2001 | Webster et al. ............... 607/14 |
| 6,308,090 B1 | 10/2001 | Tu et al. |
| 6,314,325 B1 | 11/2001 | Fitz |
| 6,322,558 B1 | 11/2001 | Taylor et al. |
| 6,322,559 B1 | 11/2001 | Daulton et al. |
| 6,325,797 B1 | 12/2001 | Stewart et al. |
| 6,364,904 B1 | 4/2002 | Smith |
| 6,385,472 B1 | 5/2002 | Hall et al. |
| 6,405,732 B1 | 6/2002 | Edwards et al. |
| 6,409,742 B1 | 6/2002 | Fulton, III et al. |
| 6,413,255 B1 | 7/2002 | Stern |
| 6,430,426 B2 | 8/2002 | Avitall |
| 6,442,415 B1 | 8/2002 | Bis et al. |
| 6,451,045 B1 | 9/2002 | Walker et al. |
| 6,480,747 B2 | 11/2002 | Schmidt |
| 6,488,679 B1 | 12/2002 | Swanson et al. |
| 6,496,737 B2 | 12/2002 | Rudie et al. |
| 6,500,174 B1 | 12/2002 | Maguire et al. |
| 6,506,189 B1 | 1/2003 | Rittman, III et al. |
| 6,511,492 B1 | 1/2003 | Rosenbluth et al. |
| 6,514,226 B1 | 2/2003 | Levin et al. |
| 6,514,249 B1 | 2/2003 | Maguire et al. |
| 6,522,926 B1 | 2/2003 | Kieval et al. |
| 6,527,739 B1 | 3/2003 | Bigus et al. |
| 6,529,756 B1 | 3/2003 | Phan et al. |
| 6,530,935 B2 | 3/2003 | Wensel et al. |
| 6,540,734 B1 | 4/2003 | Chiu et al. |
| 6,542,781 B1 | 4/2003 | Koblish et al. |
| 6,546,280 B2 | 4/2003 | Osborne |
| 6,562,031 B2 | 5/2003 | Chandrasekaran et al. |
| 6,562,034 B2 | 5/2003 | Edwards et al. |
| 6,572,612 B2 | 6/2003 | Stewart et al. |
| 6,592,581 B2 | 7/2003 | Bowe |
| 6,602,242 B1 | 8/2003 | Fung et al. |
| 6,605,061 B2 | 8/2003 | VanTassel et al. |
| 6,607,520 B2 | 8/2003 | Keane |
| 6,610,046 B1 | 8/2003 | Usami et al. |
| 6,610,083 B2 | 8/2003 | Keller et al. |
| 6,613,046 B1 | 9/2003 | Jenkins et al. |
| 6,616,624 B1 | 9/2003 | Kieval |
| 6,622,731 B2 | 9/2003 | Daniel et al. |
| 6,623,515 B2 | 9/2003 | Mulier et al. |
| 6,628,976 B1 | 9/2003 | Fuimaono et al. |
| 6,635,054 B2 | 10/2003 | Fjield et al. |
| 6,652,517 B1 | 11/2003 | Hall et al. |
| 6,685,648 B2 | 2/2004 | Flaherty et al. |
| 6,692,490 B1 | 2/2004 | Edwards |
| 6,702,811 B2 | 3/2004 | Stewart et al. |
| 6,711,444 B2 | 3/2004 | Koblish |
| 6,736,835 B2 | 5/2004 | Pellegrino et al. |
| 6,745,080 B2 | 6/2004 | Koblish |
| 6,758,830 B1 | 7/2004 | Schaer et al. |
| 6,773,433 B2 | 8/2004 | Stewart et al. |
| 6,780,183 B2 | 8/2004 | Jimenez, Jr. et al. |
| 6,802,840 B2 | 10/2004 | Chin et al. |
| 6,817,999 B2 | 11/2004 | Berube et al. |
| 6,845,267 B2 | 1/2005 | Harrison et al. |
| 6,850,801 B2 | 2/2005 | Kieval et al. |
| 6,869,431 B2 | 3/2005 | Maguire et al. |
| 6,882,886 B1 | 4/2005 | Witte et al. |
| 6,885,888 B2 | 4/2005 | Rezai |
| 6,890,329 B2 | 5/2005 | Carroll et al. |
| 6,893,436 B2 | 5/2005 | Woodard et al. |
| 6,893,438 B2 | 5/2005 | Hall et al. |
| 6,899,711 B2 | 5/2005 | Stewart et al. |
| 6,905,510 B2 | 6/2005 | Saab |
| 6,909,920 B2 | 6/2005 | Lokhoff et al. |
| 6,923,808 B2 | 8/2005 | Taimisto |
| 6,939,346 B2 | 9/2005 | Kannenberg et al. |
| 6,941,953 B2 | 9/2005 | Feld et al. |
| 6,949,097 B2 | 9/2005 | Stewart et al. |
| 6,960,206 B2 | 11/2005 | Keane |
| 6,960,207 B2 | 11/2005 | Vanney et al. |
| 6,972,016 B2 | 12/2005 | Hill, III et al. |
| 7,013,169 B2 | 3/2006 | Bowe |
| 7,013,170 B2 | 3/2006 | Bowe |
| 7,058,456 B2 | 6/2006 | Pierce |
| 7,081,115 B2 | 7/2006 | Taimisto |
| 7,104,988 B2 | 9/2006 | Altman et al. |
| 7,110,828 B2 | 9/2006 | Kolberg et al. |
| 7,115,134 B2 | 10/2006 | Chambers |
| 7,149,574 B2 | 12/2006 | Yun et al. |
| 7,162,303 B2 | 1/2007 | Levin et al. |
| 7,201,738 B1 | 4/2007 | Bengmark |
| 7,211,082 B2 | 5/2007 | Hall et al. |
| 7,221,979 B2 | 5/2007 | Zhou et al. |
| 7,254,451 B2 | 8/2007 | Seifert et al. |
| 7,285,119 B2 | 10/2007 | Stewart et al. |
| 7,291,146 B2 | 11/2007 | Steinke et al. |
| 7,311,705 B2 | 12/2007 | Sra |
| 7,381,200 B2 | 6/2008 | Katoh et al. |
| 7,390,894 B2 | 6/2008 | Weinshilboum et al. |
| 7,435,248 B2 | 10/2008 | Taimisto et al. |
| 7,517,349 B2 | 4/2009 | Truckai et al. |
| 7,526,343 B2 | 4/2009 | Peterson et al. |
| 7,542,808 B1 | 6/2009 | Peterson et al. |
| 7,617,005 B2 | 11/2009 | Demarais et al. |
| 7,637,903 B2 | 12/2009 | Lentz et al. |
| 7,647,115 B2 | 1/2010 | Levin et al. |
| 7,647,124 B2 * | 1/2010 | Williams |
| 7,653,438 B2 * | 1/2010 | Deem et al. ............... 607/44 |
| 7,682,319 B2 | 3/2010 | Martin et al. |
| 7,717,948 B2 | 5/2010 | Demarais et al. |
| 7,729,782 B2 | 6/2010 | Williams et al. |
| 7,747,334 B2 | 6/2010 | Bly et al. |
| 7,771,421 B2 | 8/2010 | Stewart et al. |
| 7,778,703 B2 | 8/2010 | Gross et al. |
| 7,789,877 B2 | 9/2010 | Vanney |
| 7,850,685 B2 | 12/2010 | Kunis et al. |
| 7,867,219 B2 | 1/2011 | Chambers |
| 7,881,807 B2 | 2/2011 | Schaer |
| 7,890,188 B2 | 2/2011 | Zhang et al. |
| 7,959,630 B2 | 6/2011 | Taimisto et al. |
| 8,019,435 B2 | 9/2011 | Hastings et al. |
| 1,026,408 A1 | 10/2011 | Ingle |
| 8,062,284 B2 | 11/2011 | Booth |
| 8,100,859 B2 | 1/2012 | Patterson et al. |
| 8,123,739 B2 | 2/2012 | McQueen et al. |
| 8,131,371 B2 | 3/2012 | Demarais et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 8,192,428 B2 | 6/2012 | Truckai et al. |
| 8,257,351 B2 | 9/2012 | Stewart et al. |

(56) References Cited

U.S. PATENT DOCUMENTS

| | | |
|---|---|---|
| 8,337,492 B2 | 12/2012 | Kunis et al. |
| 8,380,275 B2 | 2/2013 | Kim et al. |
| 8,571,665 B2 | 10/2013 | Moffitt |
| 8,702,619 B2 * | 4/2014 | Wang .......................... 600/554 |
| 8,956,352 B2 * | 2/2015 | Mauch et al. ................. 606/41 |
| 9,014,821 B2 | 4/2015 | Wang |
| 2001/0005785 A1 | 6/2001 | Sachse |
| 2001/0007070 A1 | 7/2001 | Stewart et al. |
| 2001/0020174 A1 | 9/2001 | Koblish |
| 2001/0031971 A1 | 10/2001 | Dretler et al. |
| 2002/0004631 A1 | 1/2002 | Jenkins et al. |
| 2002/0004644 A1 | 1/2002 | Koblish |
| 2002/0062124 A1 | 5/2002 | Keane |
| 2002/0087208 A1 | 7/2002 | Koblish et al. |
| 2002/0139379 A1 | 10/2002 | Edwards et al. |
| 2002/0165532 A1 | 11/2002 | Hill et al. |
| 2002/0183682 A1 | 12/2002 | Darvish et al. |
| 2003/0050681 A1 | 3/2003 | Pianca et al. |
| 2003/0060858 A1 | 3/2003 | Kieval et al. |
| 2003/0074039 A1 | 4/2003 | Puskas |
| 2003/0088244 A1 | 5/2003 | Swanson et al. |
| 2003/0125790 A1 | 7/2003 | Fastovsky et al. |
| 2003/0153967 A1 | 8/2003 | Koblish et al. |
| 2003/0158584 A1 | 8/2003 | Cates et al. |
| 2003/0181897 A1 | 9/2003 | Thomas et al. |
| 2003/0199863 A1 | 10/2003 | Swanson et al. |
| 2003/0204187 A1 | 10/2003 | Hintringer et al. |
| 2003/0216792 A1 | 11/2003 | Levin et al. |
| 2003/0233099 A1 | 12/2003 | Danaek et al. |
| 2004/0010289 A1 | 1/2004 | Biggs et al. |
| 2004/0030375 A1 | 2/2004 | Pierce |
| 2004/0049181 A1 | 3/2004 | Stewart et al. |
| 2004/0082978 A1 | 4/2004 | Harrison et al. |
| 2004/0215186 A1 | 10/2004 | Cornelius et al. |
| 2005/0010095 A1 | 1/2005 | Stewart et al. |
| 2005/0080409 A1 | 4/2005 | Young et al. |
| 2005/0187579 A1 | 8/2005 | Danek et al. |
| 2005/0228460 A1 | 10/2005 | Levin et al. |
| 2006/0074403 A1 | 4/2006 | Rafiee |
| 2006/0095029 A1 | 5/2006 | Young et al. |
| 2006/0100618 A1 | 5/2006 | Chan et al. |
| 2006/0135870 A1 | 6/2006 | Webler |
| 2006/0135953 A1 | 6/2006 | Kania et al. |
| 2006/0206150 A1 | 9/2006 | Demarais et al. |
| 2006/0241366 A1 | 10/2006 | Falwell et al. |
| 2006/0247618 A1 | 11/2006 | Kaplan et al. |
| 2006/0247619 A1 | 11/2006 | Kaplan et al. |
| 2006/0271111 A1 | 11/2006 | Demarais et al. |
| 2007/0083194 A1 | 4/2007 | Kunis et al. |
| 2007/0129720 A1 * | 6/2007 | Demarais et al. ................ 606/41 |
| 2007/0265687 A1 | 11/2007 | Deem et al. |
| 2008/0045921 A1 | 2/2008 | Anderson et al. |
| 2008/0097398 A1 | 4/2008 | Mitelberg et al. |
| 2008/0108975 A1 | 5/2008 | Appling et al. |
| 2008/0109011 A1 | 5/2008 | Thenuwara et al. |
| 2008/0255539 A1 | 10/2008 | Booth |
| 2008/0288039 A1 | 11/2008 | Reddy |
| 2008/0300587 A1 | 12/2008 | Anderson |
| 2008/0319513 A1 | 12/2008 | Pu et al. |
| 2009/0018534 A1 | 1/2009 | Taimisto et al. |
| 2009/0036948 A1 | 2/2009 | Levin et al. |
| 2009/0287202 A1 | 11/2009 | Ingle et al. |
| 2009/0306650 A1 | 12/2009 | Govari et al. |
| 2009/0312606 A1 | 12/2009 | Dayton et al. |
| 2010/0030112 A1 | 2/2010 | Anderson et al. |
| 2010/0137860 A1 | 6/2010 | Demarais et al. |
| 2010/0137952 A1 | 6/2010 | Demarais et al. |
| 2010/0168777 A1 | 7/2010 | Stangenes et al. |
| 2010/0174282 A1 | 7/2010 | Demarais et al. |
| 2010/0179512 A1 | 7/2010 | Chong et al. |
| 2010/0191112 A1 | 7/2010 | Demarais et al. |
| 2010/0204692 A1 | 8/2010 | Stewart et al. |
| 2010/0222851 A1 | 9/2010 | Deem et al. |
| 2010/0222854 A1 | 9/2010 | Demarais et al. |
| 2010/0261990 A1 | 10/2010 | Gillis et al. |
| 2011/0144639 A1 | 6/2011 | Govari |
| 2011/0160719 A1 | 6/2011 | Govari et al. |
| 2011/0264086 A1 * | 10/2011 | Ingle ............................... 606/33 |
| 2011/0306851 A1 | 12/2011 | Wang |
| 2011/0319908 A1 | 12/2011 | Thenuwara et al. |
| 2012/0010607 A1 | 1/2012 | Malecki et al. |
| 2012/0029509 A1 | 2/2012 | Smith |
| 2012/0029510 A1 | 2/2012 | Haverkost |
| 2012/0029513 A1 | 2/2012 | Smith et al. |
| 2012/0035615 A1 | 2/2012 | Koester et al. |
| 2012/0078076 A1 | 3/2012 | Stewart et al. |
| 2012/0101553 A1 | 4/2012 | Reddy |
| 2012/0116382 A1 | 5/2012 | Ku et al. |
| 2012/0116383 A1 | 5/2012 | Mauch et al. |
| 2012/0123406 A1 | 5/2012 | Edmunds et al. |
| 2012/0130289 A1 | 5/2012 | Demarais et al. |
| 2012/0130345 A1 | 5/2012 | Levin et al. |
| 2012/0130368 A1 | 5/2012 | Jenson |
| 2012/0136350 A1 | 5/2012 | Goshgarian et al. |
| 2012/0143293 A1 * | 6/2012 | Mauch et al. .................... 607/99 |
| 2012/0172837 A1 | 7/2012 | Demarais et al. |
| 2012/0191083 A1 | 7/2012 | Moll et al. |
| 2012/0197246 A1 * | 8/2012 | Mauch .............................. 606/33 |
| 2012/0277842 A1 | 11/2012 | Kunis |
| 2012/0290053 A1 | 11/2012 | Zhang et al. |
| 2012/0310065 A1 | 12/2012 | Falwell et al. |
| 2012/0310239 A1 | 12/2012 | Stewart et al. |
| 2012/0323233 A1 | 12/2012 | Maguire et al. |
| 2013/0053876 A1 | 2/2013 | Ogle |
| 2013/0085360 A1 | 4/2013 | Grunewald |
| 2013/0090637 A1 | 4/2013 | Sliwa |
| 2013/0165920 A1 | 6/2013 | Weber et al. |
| 2013/0165921 A1 | 6/2013 | Sutermeister et al. |
| 2013/0172872 A1 | 7/2013 | Subramaniam et al. |
| 2013/0172879 A1 | 7/2013 | Sutermeister et al. |
| 2013/0184703 A1 | 7/2013 | Shireman et al. |
| 2013/0184773 A1 | 7/2013 | Libbus |
| 2013/0231659 A1 * | 9/2013 | Hill et al. ......................... 606/41 |
| 2013/0253628 A1 | 9/2013 | Chaska |
| 2013/0274614 A1 | 10/2013 | Shimada |
| 2013/0274730 A1 | 10/2013 | Anderson |
| 2013/0274731 A1 | 10/2013 | Anderson |
| 2013/0274737 A1 | 10/2013 | Wang |
| 2013/0282000 A1 | 10/2013 | Parsonage |
| 2013/0282084 A1 | 10/2013 | Mathur |
| 2013/0289686 A1 | 10/2013 | Masson |
| 2013/0304047 A1 | 11/2013 | Grunewald |
| 2013/0304052 A1 | 11/2013 | Rizq et al. |
| 2013/0304062 A1 | 11/2013 | Chan |
| 2014/0025069 A1 * | 1/2014 | Willard et al. ................... 606/41 |
| 2014/0058376 A1 | 2/2014 | Horn |
| 2014/0213873 A1 | 7/2014 | Wang |
| 2014/0214018 A1 | 7/2014 | Behar et al. |
| 2014/0221805 A1 | 8/2014 | Wang |
| 2014/0243821 A1 | 8/2014 | Salahieh et al. |
| 2014/0249524 A1 | 9/2014 | Kocur |
| 2014/0257280 A1 | 9/2014 | Hanson et al. |
| 2014/0257281 A1 | 9/2014 | Squire et al. |
| 2014/0276747 A1 | 9/2014 | Abunassar et al. |
| 2014/0276752 A1 | 9/2014 | Wang et al. |
| 2014/0276787 A1 | 9/2014 | Wang et al. |
| 2014/0276789 A1 | 9/2014 | Dandler et al. |
| 2014/0303617 A1 | 10/2014 | Shimada |
| 2014/0350553 A1 | 11/2014 | Okuyama |
| 2015/0057655 A1 | 2/2015 | Osypka |
| 2015/0112329 A1 | 4/2015 | Ng |
| 2015/0126992 A1 | 5/2015 | Mogul |

FOREIGN PATENT DOCUMENTS

| | | |
|---|---|---|
| CN | 102274075 | 12/2011 |
| CN | 102488552 | 6/2012 |
| CN | 202386778 | 8/2012 |
| CN | 202426649 | 9/2012 |
| CN | 202537649 | 11/2012 |
| CN | 202538132 | 11/2012 |
| CN | 102885648 | 1/2013 |
| CN | 102885649 | 1/2013 |
| CN | 102908188 | 2/2013 |

(56) References Cited

FOREIGN PATENT DOCUMENTS

| | | |
|---|---|---|
| CN | 102908189 | 2/2013 |
| CN | 202761434 | 3/2013 |
| CN | 202843784 | 4/2013 |
| DE | 29909082 | 7/1999 |
| DE | 10252325 | 5/2004 |
| DE | 10257146 | 6/2004 |
| EP | 0132344 | 1/1986 |
| EP | 0510624 | 10/1992 |
| EP | 510624 | 7/1995 |
| EP | 732080 | 9/1996 |
| EP | 0779079 | 6/1997 |
| EP | 0821602 | 2/1998 |
| EP | 0868923 | 10/1998 |
| EP | 0728495 | 4/1999 |
| EP | 0916360 | 5/1999 |
| EP | 1233716 | 8/2002 |
| EP | 963191 | 8/2003 |
| EP | 757575 | 9/2003 |
| EP | 873760 | 1/2004 |
| EP | 779079 | 3/2004 |
| EP | 0778043 | 11/2005 |
| EP | 1042990 | 10/2006 |
| EP | 1733689 | 12/2006 |
| EP | 1802370 | 7/2007 |
| EP | 1009303 | 6/2009 |
| EP | 2208474 | 7/2010 |
| EP | 2263588 | 12/2010 |
| EP | 2519173 | 11/2012 |
| EP | 2558016 | 2/2013 |
| EP | 2598069 | 6/2013 |
| EP | 2664295 | 11/2013 |
| EP | 2694158 | 2/2014 |
| EP | 2759275 | 7/2014 |
| EP | 2760532 | 8/2014 |
| EP | 2804554 | 11/2014 |
| JP | 355137141 | 10/1980 |
| WO | WO-9115254 | 10/1991 |
| WO | WO-9220291 | 11/1992 |
| WO | WO-9421168 | 9/1994 |
| WO | WO-9513111 | 5/1995 |
| WO | WO-9520416 | 8/1995 |
| WO | WO-9525472 | 9/1995 |
| WO | WO-9600036 | 1/1996 |
| WO | WO-9632980 | 10/1996 |
| WO | WO-9638196 | 12/1996 |
| WO | WO9717892 | 5/1997 |
| WO | WO-9736548 | 10/1997 |
| WO | WO-9802201 | 1/1998 |
| WO | WO-9833469 | 8/1998 |
| WO | WO-9843530 | 10/1998 |
| WO | WO9900060 | 1/1999 |
| WO | WO-9923958 | 5/1999 |
| WO | WO-9952421 | 10/1999 |
| WO | WO-9956801 | 11/1999 |
| WO | WO-9962413 | 12/1999 |
| WO | WO-0001313 | 1/2000 |
| WO | WO-0056237 | 9/2000 |
| WO | WO-0067832 | 11/2000 |
| WO | WO-0119270 | 3/2001 |
| WO | WO-0122897 | 4/2001 |
| WO | WO-0137723 | 5/2001 |
| WO | WO-0137746 | 5/2001 |
| WO | WO-0170114 | 9/2001 |
| WO | WO-0180758 | 11/2001 |
| WO | WO-0245608 | 6/2002 |
| WO | WO-02083017 | 10/2002 |
| WO | WO-02087453 | 11/2002 |
| WO | WO-02087679 | 11/2002 |
| WO | WO-02089687 | 11/2002 |
| WO | WO-02089908 | 11/2002 |
| WO | WO-03082080 | 10/2003 |
| WO | WO-2004100813 | 11/2004 |
| WO | WO-2005030072 | 4/2005 |
| WO | WO-2005041748 | 5/2005 |
| WO | WO-2005051216 | 6/2005 |
| WO | WO-2005070491 | 8/2005 |
| WO | WO-2005110528 | 11/2005 |
| WO | WO-2006020920 | 2/2006 |
| WO | WO-2006041881 | 4/2006 |
| WO | WO-2006065949 | 6/2006 |
| WO | WO-2006092000 | 9/2006 |
| WO | WO-2007001981 | 1/2007 |
| WO | WO-2007008954 | 1/2007 |
| WO | WO-2007128064 | 11/2007 |
| WO | WO-2007135431 | 11/2007 |
| WO | WO-2008101244 | 8/2008 |
| WO | WO-2009121017 | 1/2009 |
| WO | WO-2010048676 | 5/2010 |
| WO | WO-2010091701 | 8/2010 |
| WO | WO-2010120835 | 10/2010 |
| WO | WO-2011015218 | 2/2011 |
| WO | WO-2011019838 | 2/2011 |
| WO | WO-2011082279 | 7/2011 |
| WO | WO-2011130534 | 10/2011 |
| WO | WO-2012075156 | 6/2012 |
| WO | WO-2012130337 | 10/2012 |
| WO | WO-2012131107 | 10/2012 |
| WO | WO-2012154219 | 11/2012 |
| WO | WO-2012154796 | 11/2012 |
| WO | WO-2013016203 | 1/2013 |
| WO | WO-2013028993 | 2/2013 |
| WO | WO-2013030807 | 3/2013 |
| WO | WO-2013040201 | 3/2013 |
| WO | WO-2013049601 | 4/2013 |
| WO | WO-2013101452 | 7/2013 |
| WO | WO-2013106054 | 7/2013 |
| WO | WO2013109318 | 7/2013 |
| WO | WO2013158676 | 10/2013 |
| WO | WO2013158678 | 10/2013 |
| WO | WO2013165920 | 11/2013 |
| WO | WO2013154776 | 12/2013 |
| WO | WO-2014036160 | 3/2014 |
| WO | WO-2014036163 | 3/2014 |
| WO | WO-2014056460 | 4/2014 |
| WO | WO-2014163987 | 10/2014 |
| WO | WO-2014163990 | 10/2014 |

OTHER PUBLICATIONS

International Search Report, PCT/US03/031339, Feb. 18, 2004, 3 Pages.
International Search Report, PCT/US01/044977, Jun. 7, 2002, 6 Pages.
Beale et al., "Minimally Invasive Treatment for Varicose Veins: A Review of Endovenous Laser Treatment and Radiofrequency Ablation". Lower Extremity Wounds 3(4), 2004, 10 pages.
Doumas, Michael et al., "Renal Nerve Ablation for Resistant Hypertension: The Dust Has Not Yet Settled." The Journal of Clinical Hypertension. 2014; vol. 16, No. 6, 2 pages.
Messerli, Franz H. et al. "Renal Denervation for Resistant Hypertension: Dead or Alive?" Healio: Cardiology today's Intervention, May/Jun. 2014, 2 pages.
Miller, Reed, "Finding a Future for Renal Denervation With Better Controlled Trials." Pharma & Medtech Business Intelligence, Article # 01141006003, Oct. 6, 2014, 4 pages.
Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.
Papademetriou, Vasilios et al., "Renal Nerve Ablation for Resistant Hypertension: How Did We Get Here, Present Status, and Future Directions." Circulation. 2014; 129: 1440-1450.
Papademetriou, Vasilios, "Renal Denervation and Symplicity HTN-3: "Dubium Sapientiae Initium" (Doubt Is the Beginning of Wisdom)", Circulation Research, 2014; 115: 211-214.
International Search Report and Written Opinion for International App. No. PCT/US2014/026854, mailed Oct. 10, 2014, 15 pages.
Claudine Jaboro, "An in vivo study of the biocompatibility of classic and novel device materials on the central nervous system", (Jan. 1, 2007), ETD Collection for Wayne State University. Paper AA13310737, 2 pages. <http://digitalcommons.wayne.edu/dissertations/AA13310737>.

(56) References Cited

OTHER PUBLICATIONS

European Search Report dated Jan. 30, 2013; European Application No. 12180426.4; Applicant: Medtronic Ardian Luxembourg S.a.r.I.; 6 pages.
European Search Report dated Feb. 28, 2013; European Application No. 12180427.2; Applicant: Medtronic Ardian Luxembourg S.a.r.I.; 4 pages.
European Search Report dated Jan. 30, 2013; Application No. 12180428.0; Applicant: Medtronic Ardian Luxembourg S.a.r.I.; 6 pages.
European Search Report dated Jan. 30, 2013; Application No. 12180430.6; Applicant: Medtronic Ardian Luxembourg S.a.r.I.; 6 pages.
European Search Report dated Jan. 30, 2013; Application No. 12180431.4; Applicant: Medtronic Ardian Luxembourg S.a.r.I.; 6 pages.
European Search Report dated Feb. 22, 2013; Application No. 12180432.2; Applicant: Medtronic Ardian Luxembourg S.a.r.I.; 6 pages.
International Search Report and Written Opinion dated Jan. 23, 2012, International Application No. PCT/US2011/057761, 13 pages.
International Search Report and Written Opinion dated Jan. 20, 2012, International Application No. PCT/US2011/057756, 10 pages.
International Search Report and Written Opinion dated Feb. 16, 2012, International Application No. PCT/US2011/057754, 13 pages.
Lahiri D. et al. "Boron nitride nanotube reinforced polylactide-polycaprolactone copolymer composite: Mechanical properties and cytocompatibility with osteoblasts and macrophages in vitro." Acta Biomater (2010), doi: 10.1016/j.actbio.2010.02.44, 10 pages.
Hanker et al., "Biomedical Materials and Devices," Materials Research Society Symposium Proceedings, vol. 110, Dec. 4, 1987, Boston Massachusetts, USA, 8 pages.
European Search Report for European Application No. 13159256, Date Mailed: Oct. 17, 2013, 6 pages.
U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.
"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europcr-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages. <http://www.cxvascular.com/in-latest-news/interventional-news—latest-news/does-renal-denervation-represent-a-new-treatment-option-for-resistant-hypertension>.
"Iberis—Renal Sympathetic Denervation System: Turning innovation into quality care." [Brochure], Terumo Europe N. V., 2013, Europe, 3 pages.
"Neurotech Reports Announces Winners of Gold Electrode Awards." Neurotech business report, 2009. 1 page. <http://www.neurotechreports.com/pages/goldelectrodes09.html>.
"Quick. Consistent. Controlled. OneShot renal Denervation System" [Brochure], Covidien: positive results for life, 2013, (n.I.), 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison Awards[TM]" Edison Awards: Honoring Innovations & Innovators, 2013, 2 pages, <http://www.edisonawards.com/Awards.php>.
"The Future of Renal denervation for the Treatment of Resistant Hypertension." St. Jude Medical, Inc., 2012, 12 pages.
"Vessix Renal Denervation System: So Advanced Its Simple." [Brochure], Boston Scientific: Advancing science for life, 2013, 6 pages.
Asbell, Penny, "Conductive Keratoplasty for the Correction of Hyperopia." Tr Am Ophth Soc, 2001, vol. 99, 10 pages.
Badoer, Emilio, "Cardiac afferents play the dominant role in renal nerve inhibition elicited by volume expansion in the rabbit." Am J Physiol Regul Integr Comp Physiol, vol. 274, 1998, 7 pages.
Bengel, Frank, "Serial Assessment of Sympathetic Reinnervation After Orthotopic Heart Transplantation: A longitudinal Study Using PET and C-11 Hydroxyephedrine." Circulation, vol. 99, 1999,7 pages.
Benito, F., et al. "Radiofrequency catheter ablation of accessory pathways in infants." Heart, 78:160-162 (1997).
Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global Symplicity registry." EuroIntervention, vol. 9, 2013, 9 pages.
Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.
Davis, Mark et al., "Effectiveness of Renal Denervation Therapy for Resistant Hypertension." Journal of the American College of Cardiology, vol. 62, No. 3, 2013, 11 pages.
Dibona, G.F. "Sympathetic nervous system and kidney in hypertension." Nephrol and Hypertension, 11: 197-200 (2002).
Dubuc, M., et al., "Feasibility of cardiac cryoablation using a transvenous steerable electrode catheter." J Interv Cardiac Electrophysiol, 2:285-292 (1998).
Final Office Action; U.S. Appl. No. 12/827,700; Mailed on Feb. 5, 2013, 61 pages.
Geisler, Benjamin et al., "Cost-Effectiveness and Clinical Effectiveness of Catheter-Based Renal Denervation for Resistant Hypertension." Journal of the American College of Cardiology, Col. 60, No. 14, 2012, 7 pages.
Gelfand, M., et al., "Treatment of renal failure and hypertension." U.S. Appl. No. 60/442,970, Jan. 29, 2003, 23 pages.
Gertner, Jon, "Meet the Tech Duo That's Revitalizing the Medical Device Industry." Fast Company, Apr. 15, 2013, 6:00 AM, 17 pages, <http://www.fastcompany.com/3007845/meet-tech-duo-thats-revitalizing-medical-device-industry>.

(56) References Cited

OTHER PUBLICATIONS

Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).
Hall, W. H., et al. "Combined embolization and percutaneous radiofrequency ablation of a solid renal tumor." *Am. J. Roentgenol*,174: 1592-1594 (2000).
Han, Y.-M, et al., "Renal artery ebolization with diluted hot contrast medium: An experimental study." J Vasc Intery Radiol, 12: 862-868 (2001).
Hansen, J. M., et al. "The transplanted human kidney does not achieve functional reinnervation." *Clin. Sci*, 87: 13-19 (1994).
Hendee, W. R. et al. "Use of Animals in Biomedical Research: The Challenge and Response." *American Medical Association White Paper* (1988) 39 pages.
Hering, Dagmara et al., "Chronic kidney disease: role of sympathetic nervous system activation and potential benefits of renal denervation." EuroIntervention, vol. 9, 2013, 9 pages.
Huang et al., "Renal denervation prevents and reverses hyperinsulinemia-induced hypertension in rats." Hypertension 32 (1998) pp. 249-254.
Imimdtanz, "Medtronic awarded industry's highest honour for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.
Kaiser, Chris, AHA Lists Year's Big Advances in CV Research, medpage Today, Dec. 18, 2012, 4 pages, <http://www.medpagetoday.com/Cardiology/PCI/36509>.
Kompanowska, E., et al., "Early Effects of renal denervation in the anaesthetised rat: Natriuresis and increased cortical blood flow." J Physiol, 531. 2:527-534 (2001).
Lee, S.J., et al. "Ultrasonic energy in endoscopic surgery." Yonsei Med J, 40:545-549 (1999).
Linz, Dominik et al., "Renal denervation suppresses ventricular arrhythmias during acute ventricular ischemia in pigs." Heart Rhythm, vol. 0, No. 0, 2013, 6 pages.
Lustgarten, D.L.,et al., "Cryothermal ablation: Mechanism of tissue injury and current experience in the treatment of tachyarrhythmias." Progr Cardiovasc Dis, 41:481-498 (1999).
Mabin, Tom et al., "First experience with endovascular ultrasound renal denervation for the treatment of resistant hypertension." EuroIntervention, vol. 8, 2012, 5 pages.
Mahfoud, Felix et al., "Ambulatory Blood Pressure Changes after Renal Sympathetic Denervation in Patients with Resistant Hypertension." Circulation, 2013, 25 pages.
Mahfoud, Felix et al., "Expert consensus document from the European Society of Cardiology on catheter-based renal denervation." European Heart Journal, 2013, 9 pages.
Mahfoud, Felix et al., "Renal Hemodynamics and Renal Function After Catheter-Based Renal Sympathetic Denervation in Patients With Resistant Hypertension." Hypertension, 2012, 6 pages.
Medical-Dictionary.com, Definition of "Animal Model," http://medical-dictionary.com (search "Animal Model"), 2005, 1 page.
Medtronic, Inc., Annual Report (Form 10-K) (Jun. 28, 2011) 44 pages.
Millard, F. C., et al, "Renal Embolization for ablation of function in renal failure and hypertension." Postgraduate Medical Journal, 65, 729-734, (1989).
Oliveira, V., et al., "Renal denervation normalizes pressure and baroreceptor reflex in high renin hypertension in conscious rats." Hypertension, 19:II-17-II-21 (1992).
Ong, K. L., et al. "Prevalence, Awareness, Treatment, and Control of Hypertension Among United States Adults 1999-2004." Hypertension, 49: 69-75 (2007) (originally published online Dec. 11, 2006).
Ormiston, John et al., "First-in-human use of the OneShot$^{TM}$ renal denervation system from Covidien." EuroIntervention, vol. 8, 2013, 4 pages.
Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.
Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.
Peet, M., "Hypertension and its Surgical Treatment by bilateral supradiaphragmatic splanchnicectomy" Am J Surgery (1948) pp. 48-68.
Renal Denervation (RDN), Symplicity RDN System Common Q&A (2011), 4 pages, http://www.medtronic.com/rdn/mediakit/RDN%20FAQ.pdf.
Schauerte, P., et al. "Catheter ablation of cardiac autonomic nerves for prevention of vagal atrial fibrillation." Circulation, 102:2774-2780 (2000).
Schlaich, Markus et al., "Renal Denervation in Human Hypertension: Mechanisms, Current Findings, and Future Prospects." Curr Hypertens Rep, vol. 14, 2012, 7 pages.
Schmid, Axel et al., "Does Renal Artery Supply Indicate Treatment Success of Renal Denervation." Cardiovasc Intervent Radiol, vol. 36, 2013, 5 pages.
Schmieder, Roland E. et al., "Updated ESH position paper on interventional therapy of resistant hypertension." EuroIntervention, vol. 9, 2013, 9 pages.
Sievert, Horst, "Novelty Award EuroPCR 2010." Euro PCR, 2010, 15 pages.
Solis-Herruzo et al., "Effects of lumbar sympathetic block on kidney function in cirrhotic patients with hepatorenal syndrome," J. Hepatol. 5 (1987), pp. 167-173.
Stella, A., et al., "Effects of reversible renal deneravation on haemodynamic and excretory functions on the ipsilateral and contralateral kidney in the cat." Hypertension, 4:181-188 (1986).
Stouffer, G. A. et al., Journal of Molecular and Cellular Cardiology, vol. 62, 2013, 6 pages.
Swartz, J.F., et al., "Radiofrequency endocardial catheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." PACE, 21:2517-2521 (1998).
Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.
Weinstock, M., et al., "Renal denervation prevents sodium rentention and hypertension in salt sensitive rabbits with genetic baroreflex impairment." Clinical Science, 90:287-293 (1996).
Wilcox, Josiah N., Scientific Basis Behind Renal Denervation for the Control of Hypertension, ICI 2012, Dec. 5-6, 2012. 38 pages.
Worthley, Stephen et al., "Safety and efficacy of a multi-electrode renal sympathetic denervation system in resistant hypertension: the EnligHTN I trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Avitall et al., "The creation of linear contiguous lesions in the atria with an expandable loop catheter,"Journal of the American College of Cardiology, 1999; 33; pp. 972-984.
Blessing, Erwin et al., Cardiac Ablation and Renal Denervation Systems Have Distinct Purposes and Different Technical Requirements, JACC Cardiovascular Interventions, vol. 6, No. 3, 2013, 1 page.
ClinicalTrials.gov, Renal Denervation in Patients with uncontrolled Hypertension in Chinese (2011), 6pages. www.clinicaltrials.gov/ct2/show/NCT01390831.

(56) References Cited

OTHER PUBLICATIONS

Excerpt of Operator's Manual of Boston Scientific's EPT-1000 XP Cardiac Ablation Controller & Accessories, Version of Apr. 2003, (6 pages).
Excerpt of Operator's Manual of Boston Scientific's Maestro 30000 Cardiac Ablation System, Version of Oct. 17, 2005 , (4 pages).
Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.
Kandarpa, Krishna et al., "Handbook of Interventional Radiologic Procedures", Third Edition, pp. 194-210 (2002).
Mount Sinai School of Medicine clinical trial for Impact of Renal Sympathetic Denervation of Chronic Hypertension, Mar. 2013, http://clinicaltrials.gov/ct2/show/NCT01628198.
Opposition to European Patent No. EP1802370, Granted Jan. 5, 2011, Date of Opposition Oct. 5, 2011, 20 pages.
Opposition to European Patent No. EP2037840, Granted Dec. 7, 2011, Date of Opposition Sep. 7, 2012, 25 pages.
Opposition to European Patent No. EP2092957, Granted Jan. 5, 2011, Date of Opposition Oct. 5, 2011, 26 pages.
Oz, Mehmet, Pressure Relief, TIME, Jan. 9, 2012, 2 pages. <www.time.come/time/printout/0,8816,2103278,00.html>.
Papademetriou, Vasilios, Renal Sympathetic Denervation for the Treatment of Difficult-to-Control or Resistant Hypertension, Int. Journal of Hypertension, 2011, 8 pages.
Prochnau, Dirk et al., Catheter-based renal denervation for drug-resistant hypertension by using a standard electrophysiology catheter; Euro Intervention 2012, vol. 7, pp. 1077-1080.
Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.
Purerfellner, Helmut et al., Pulmonary Vein Stenosis Following Catheter Ablation of Atrial Fibrillation, Curr. Opin. Cardio. 20 :484-490, 2005.
Schneider, Peter A., "Endovascular Skills—Guidewire and Catheter Skills for Endovascular Surgery," Second Edition Revised and Expanded, 10 pages, (2003).
ThermoCool Irrigated Catheter and Integrated Ablation System, Biosense Webster (2006), 6 pages.
Tsao, Hsuan-Ming, Evaluation of Pulmonary Vein Stenosis after Catheter Ablation of Atrial Fibrillation, Cardiac Electrophysiology Review, 6, 2002, 4 pages.
Wittkampf et al., "Control of radiofrequency lesion size by power regulation," Journal of the American Heart Associate, 1989, 80: pp. 962-968.
Zheng et al., "Comparison of the temperature profile and pathological effect at unipolar, bipolar and phased radiofrequency current configurations," Journal of Interventional Cardiac Electrophysiology, 2001, pp. 401-410.
Allen, E.V., Sympathectomy for essential hypertension, Circulation, 1952, 6:131-140.
Bello-Reuss, E. et al., "Effects of Acute Unilateral Renal Denervation in the Rat," Journal of Clinical Investigation, vol. 56, Jul. 1975, pp. 208-217.
Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.
Bhandari, A. and Ellias, M., "Loin Pain Hemaluria Syndrome: Pain Control with RFA to the Splanchanic Plexus," The Pain Clinc, 2000, vol. 12, No. 4, pp. 323-327.

Curtis, John J. et al., "Surgical Therapy for Persistent Hypertension After Renal Transplantation" Transplantation, 31:125-128 (1981).
Dibona, Gerald F. et al., "Neural Control of Renal Function," Physiological Reviews, vol. 77, No. 1, Jan. 1997, The American Physiological Society 1997, pp. 75-197.
Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.
Janssen, Ben J.A. et al., "Effects of Complete Renal Denervation and Selective Afferent Renal Denervation on the Hypertension Induced by Intrenal Norepinephrine Infusion in Conscious Rats", Journal of Hypertension 1989, 7: 447-455.
Katholi, Richard E., "Renal Nerves in the Pathogenesis of Hypertension in Experimental Animals and Humans," Am J. Physiol. vol. 245, 1983, the American Physiological Society 1983, pp. F1-F14.
Krum, Henry et al., "Catheter-Based Renal Sympathetic Denervation for Resistant Hypertension: A Mulitcentre Safety and Proof-of Principle Cohort Study," Lancet 2009; 373:1275-81.
Krum, et al., "Renal Sympathetic-Nerve Ablation for Uncontrolled Hypertension." New England Journal of Med, Aug. 2009, 361;9.
Luippold, Gerd et al., "Chronic Renal Denervation Prevents Glomerular Hyperfiltration in Diabetic Rats", Nephrol Dial Transplant, vol. 19, No. 2, 2004, pp. 342-347.
Mahfoud et al. "Treatment strategies for resistant arterial hypertension" Dtsch Arztebl Int. 2011;108:725-731.
Osborn, et al., "Effect of Renal Nerve Stimulation on Renal Blood Flow Autoregulation and Antinatriuresis During Reductions in Renal Perfusion Pressure," Proceedings of the Society for Experimentla Biology and Medicine, vol. 168, 77-81, 1981.
Page, I.H. et al., "The Effect of Renal Denervation on Patients Suffering From Nephritis," Feb. 27, 1935;443-458.
Page, I.H. et al., "The Effect of Renal Denervation on the Level of Arterial Blood Pressure and Renal Function in Essential Hypertension," J. Clin Invest. 1934;14:27-30.
Rocha-Singh, "Catheter-Based Sympathetic Renal Denervation," Endovascular Today, Aug. 2009.
Schlaich, M.P. et al., "Renal Denervation as a Therapeutic Approach for Hypertension: Novel Implictions for an Old Concept," Hypertension, 2009; 54:1195-1201.
Schlaich, M.P. et al., "Renal Sympathetic-Nerve Ablation for Uncontrolled Hypertension," N Engl J Med 2009; 361(9): 932-934.
Smithwick, R.H. et al., "Splanchnicectomy for Essential Hypertension," Journal Am Med Assn, 1953; 152:1501-1504.
Symplicity HTN-1 Investigators; Krum H, Barman N, Schlaich M, et al. Catheter-based renal sympathetic denervation for resistant hypertension: durability of blood pressure reduction out to 24 months. Hypertension. 2011 ;57(5):911-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.
Valente, John F. et al., "Laparoscopic Renal Denervation for Intractable ADPKD-Related Pain", Nephrol Dial Transplant (2001) 16:160.
Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.

\* cited by examiner

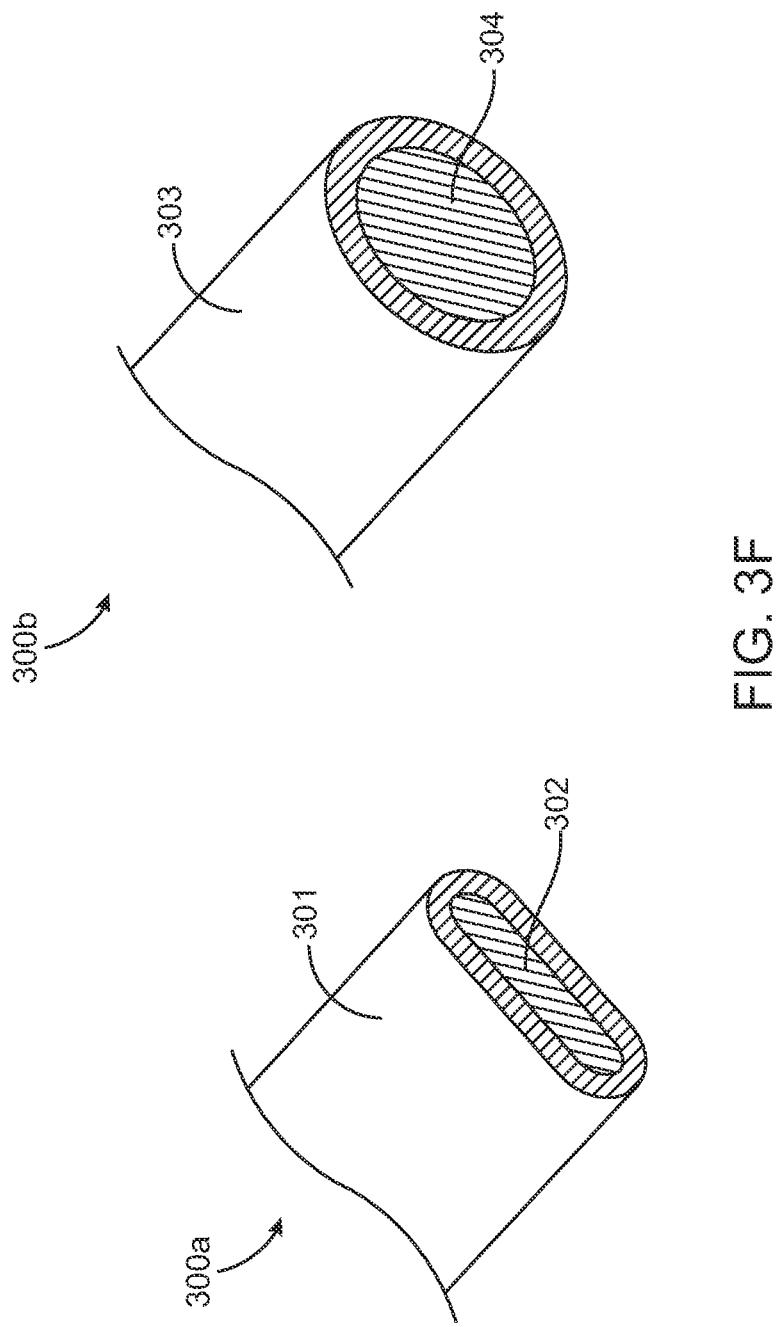

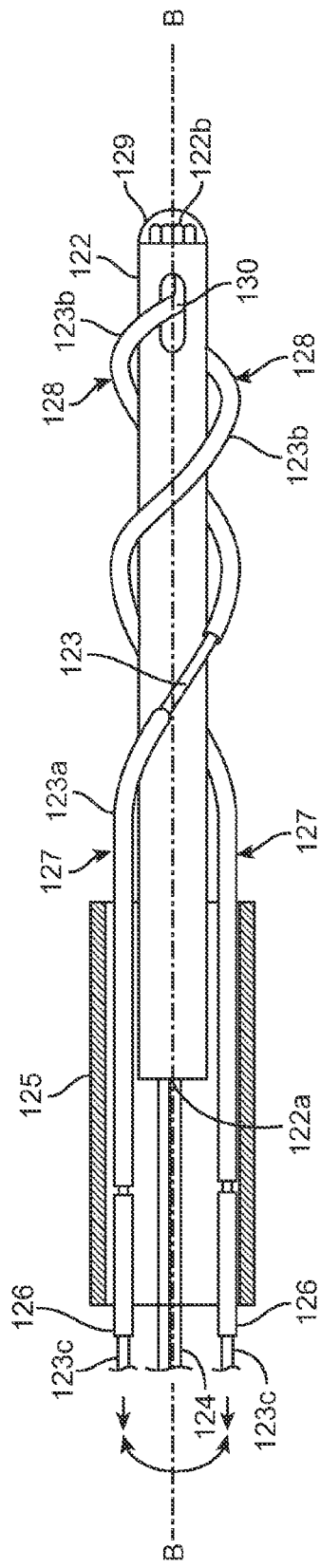
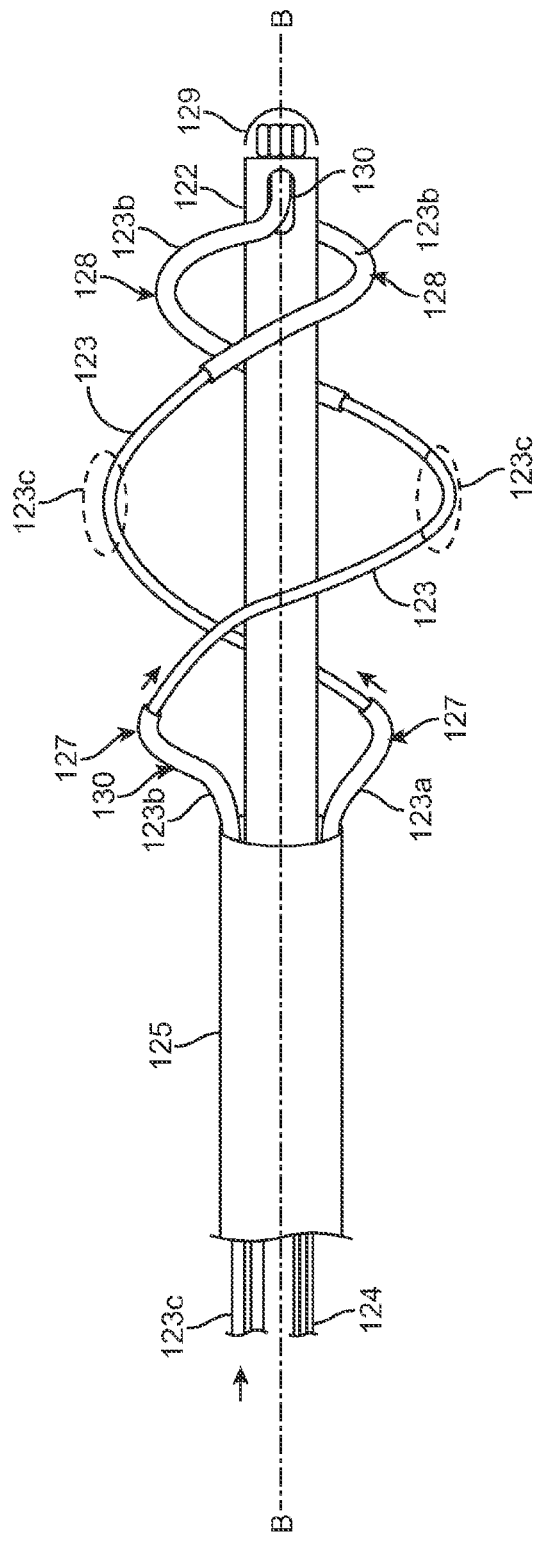
FIG. 5B
FIG. 5C

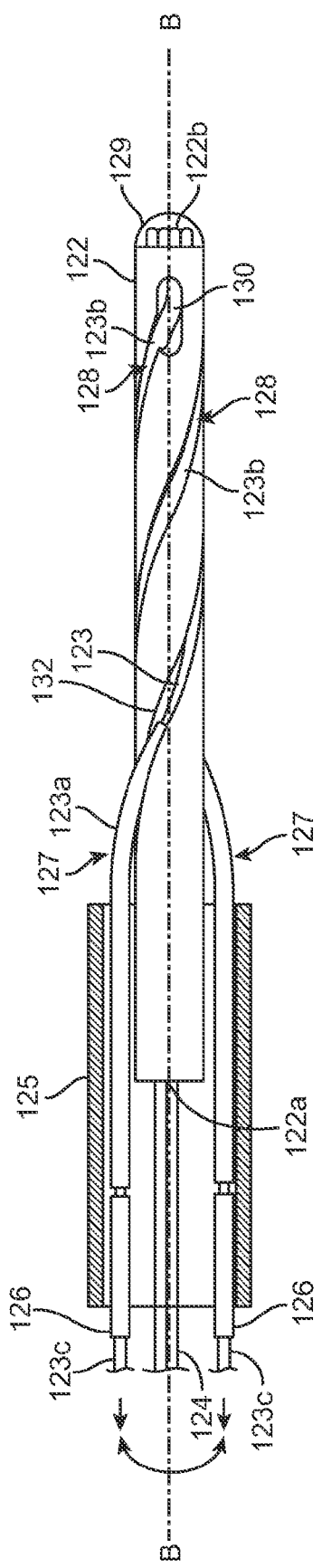
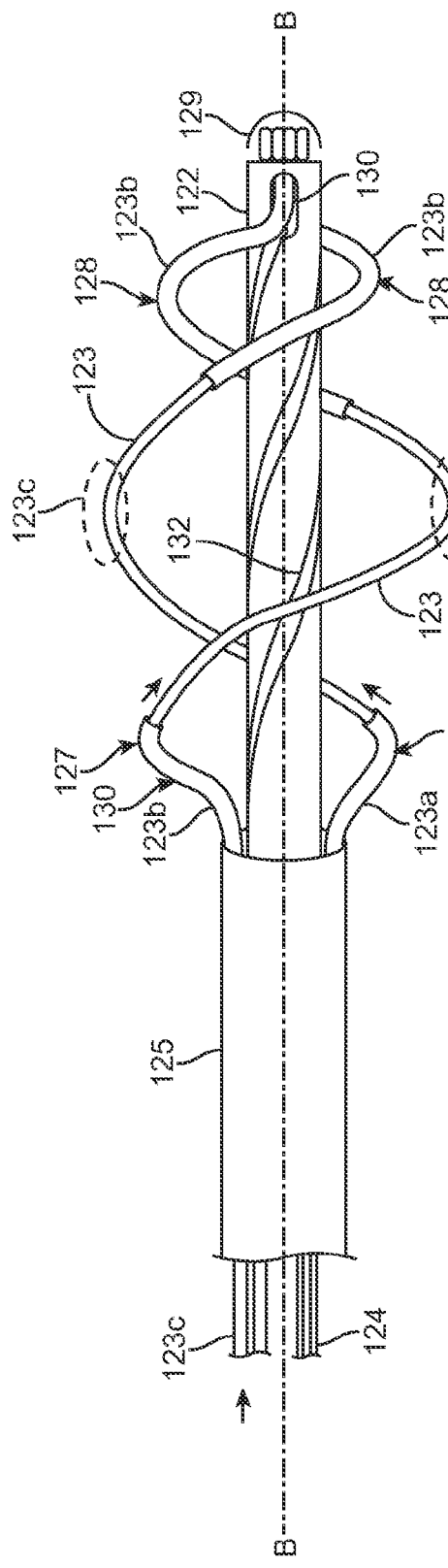

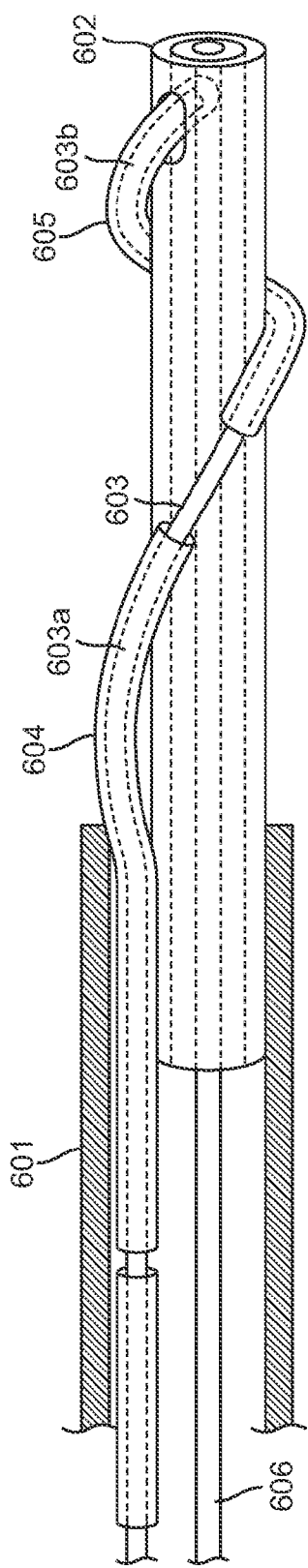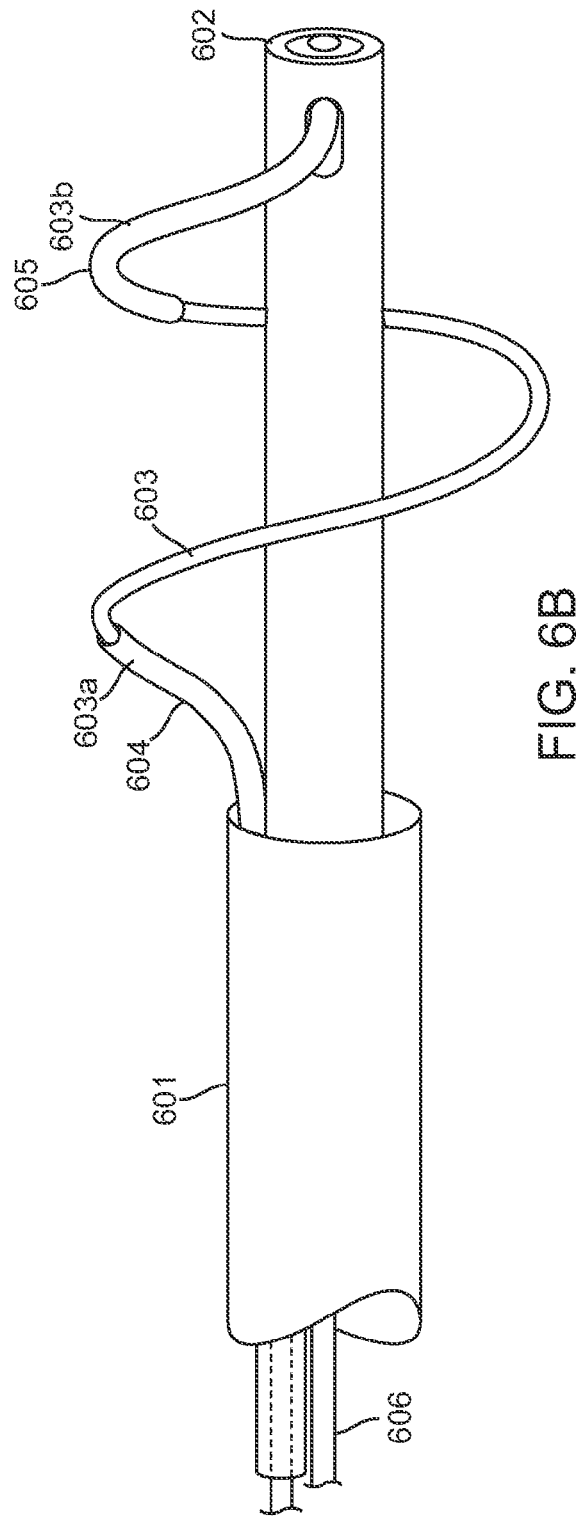
FIG. 6A
FIG. 6B

HELICAL PUSH WIRE ELECTRODE

TECHNICAL FIELD

The present disclosure relates generally to the field of neuromodulation and associated systems and methods. More particularly, some embodiments relate to the use of helical push wire electrode radio frequency (RF) ablation catheter apparatuses for intravascular neuromodulation (e.g., renal neuromodulation) and associated systems and methods.

BACKGROUND

The sympathetic nervous system (SNS) is primarily an involuntary bodily control system associated with stress responses. Fibers of the SNS innervate tissue and are present in almost every organ of the human body. The SNS can regulate characteristics such as pupil diameter, gut motility, and urinary output. Such regulation has adaptive utility in maintaining homeostasis or preparing the body for rapid responses to changes in environmental conditions. Chronic activation of the SNS, however, is a common maladaptive response that can drive the progression of many diseases. Excessive activation of the renal SNS, in particular, has been experimentally identified as a likely contributor to the complex pathophysiology of hypertension, volume overload states (such as heart failure), and progressive renal disease. Radiotracer dilution has demonstrated, for example, increased renal norepinephrine ("NE") spillover rates in patients with essential hypertension.

Cardio-renal sympathetic nerve hyperactivity can be pronounced in patients with heart failure. These patients often have an exaggerated NE overflow of plasma from the heart and kidneys. Heightened SNS activation commonly characterizes both chronic and end stage renal disease. In patients with end stage renal disease, NE plasma levels above the median are predictive of cardiovascular diseases and causes of death. This is also true for patients suffering from diabetic or contrast nephropathy. Evidence suggests that sensory afferent signals originating from diseased kidneys are major contributors to initiating and sustaining elevated central sympathetic outflow.

Sympathetic nerves innervating the kidneys terminate in the blood vessels, the juxtaglomerular apparatus, and the renal tubules. Stimulation of the renal sympathetic nerves can cause increased renin release, increased sodium (Na+) reabsorption, and a reduction of renal blood flow. These neural regulation components of renal function are considerably stimulated in disease states characterized by heightened sympathetic tone and likely contribute to increased blood pressure in hypertensive patients. The reduction of renal blood flow and glomerular filtration rate because of renal sympathetic efferent stimulation is likely a cornerstone of the loss of renal function in cardio-renal syndrome (i.e., renal dysfunction as a progressive complication of chronic heart failure). Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release), and diuretics (intended to counter the renal sympathetic mediated sodium and water retention). These pharmacologic strategies, however, have significant limitations including limited efficacy, compliance issues, side effects, and others. Recently, intravascular devices that reduce sympathetic nerve activity by applying an energy field to a target site in the renal artery (e.g., via radiofrequency ablation) have been shown to reduce blood pressure in patients with treatment-resistant hypertension.

BRIEF DESCRIPTION OF THE DRAWINGS

FIG. 3F is a cross-sectional perspective view illustrating a round cored wire and a flat cored wire in accordance with an embodiment of the present technology.

FIG. 5B is a profile view illustrating the treatment device shown in FIG. 5A in a delivery state.

FIG. 5C is a profile view illustrating the treatment device shown in FIG. 5A in a deployed state.

FIG. 5E is a profile view illustrating a distal support section including helical grooves in a delivery state in accordance with an embodiment of the present technology.

FIG. 5F is a cross-sectional end view illustrating the distal support section shown in FIG. 5E in a deployed state in accordance with an embodiment of the present technology.

FIG. 6A is a profile view of a treatment device including a helical push wire electrode in a delivery state in accordance with an embodiment of the present technology.

FIG. 6B is a profile view of the treatment device shown in FIG. 6A in a deployed state in accordance with an embodiment of the present technology.

DETAILED DESCRIPTION

Figure 1:
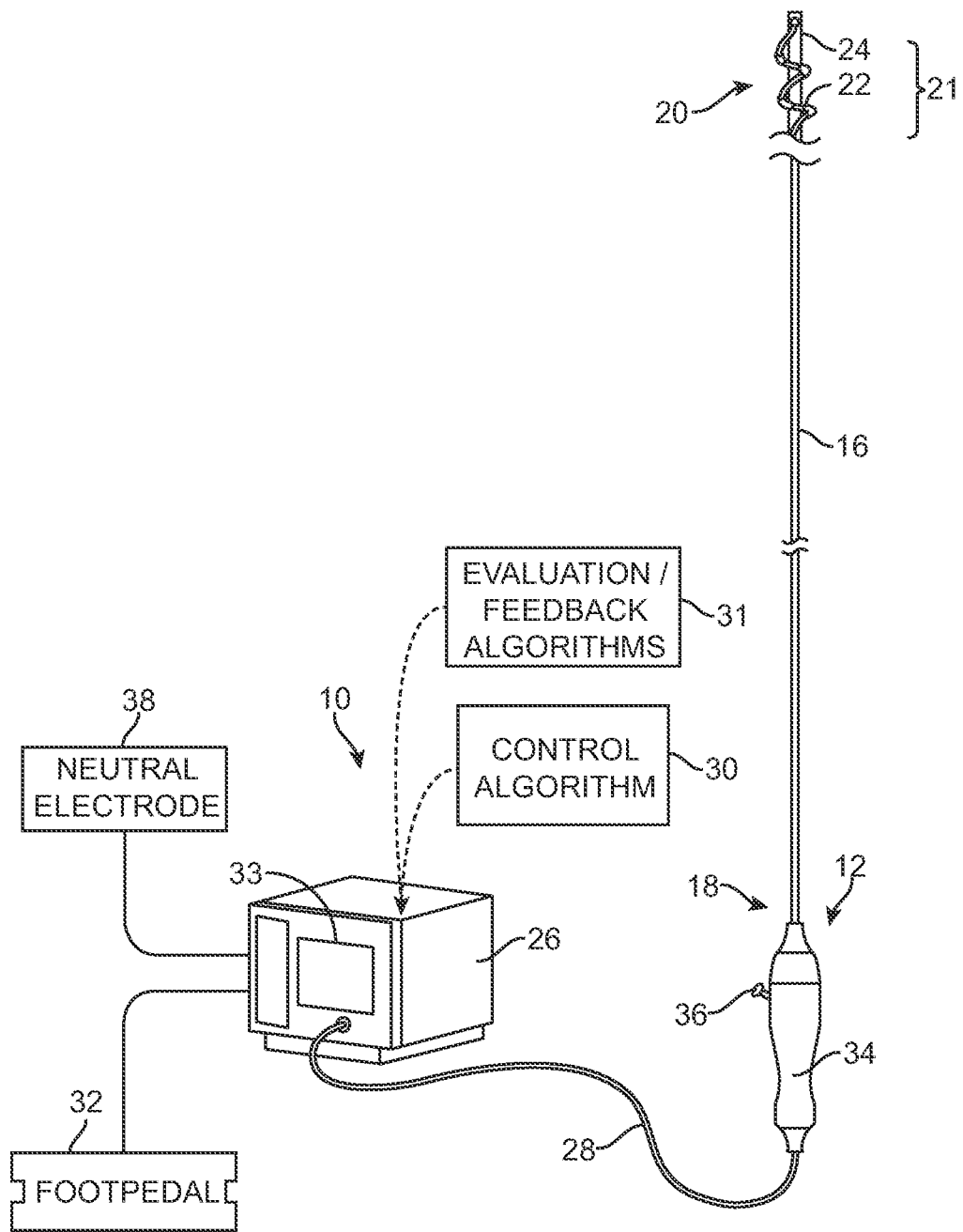
FIG. 1 is a perspective view illustrating a system in accordance with an embodiment of the present technology.

The present technology, in accordance with one or more various embodiments, is described in detail with reference to the accompanying figures. The drawings are provided for purposes of illustration only and merely depict typical or example embodiments of the invention. These drawings are provided to facilitate the reader's understanding of the systems and methods described herein, and shall not be considered limiting of the breadth, scope, or applicability of the claimed invention. The figures are not intended to be exhaustive or to limit the embodiments to the precise form disclosed. It should be understood that the embodiments can be practiced with modification and alteration, and that the invention be limited only by the claims and the equivalents thereof.

The present technology is directed to apparatuses, systems, and methods for achieving electrically and/or thermally induced neuromodulation by percutaneous transluminal intravascular access. In particular, embodiments of the present technology relate to apparatuses, systems, and methods that incorporate a catheter treatment device having a helical push wire electrode between a delivery state (e.g., a generally straight or elongated shape) and a deployed state (e.g., a radially expanded, generally helical shape). The electrodes are configured to deliver energy (e.g., electrical energy, radio frequency (RF) energy, pulsed electrical energy, or thermal energy) to a vessel wall (e.g., wall of a renal artery) after being advanced via a catheter along a percutaneous transluminal path (e.g., a femoral artery puncture, an iliac artery and aorta, a radial artery, or another suitable intravascular path). The helical push wire electrode is sized and shaped so that the electrodes contact an interior wall of the renal artery when the electrode is in the deployed (e.g., helical) state.

The helical shape of the deployed electrode allows blood to flow through the helix. This is expected to help prevent occlusion of the renal artery during activation of the electrode. Furthermore, blood flow in and around the electrode may cool the associated electrode and/or the surrounding tissue. In some embodiments, cooling the electrode allows for the delivery of higher power levels at lower temperatures. This feature is expected to help create deeper and/or larger lesions during therapy, reduce intimal surface temperature, and/or allow longer activation times while reducing the risk of overheating during treatment.

Specific details of several embodiments of the present technology are described herein with reference to the accompanying figures. Although many of the embodiments are described herein with respect to apparatuses, systems, and methods for intravascular modulation of renal nerves using helical push wire electrodes, other treatment modalities and other nerves innervating other organs in addition to those described herein are within the scope of the present technology. Additionally, other embodiments of the present technology can have configurations, components, or procedures different from those described herein. For example, other embodiments can include additional elements and features beyond those described herein or be without several of the elements and features shown and described herein.

Generally, unless the context indicates otherwise, the terms "distal" and "proximal" within this disclosure reference a position relative to an operator or an operator's control device. For example, "proximal" can refer to a position closer to an operator or an operator's control device, and "distal" can refer to a position that is more distant from an operator or an operator's control device. The headings provided herein are for convenience only.

I. RENAL NEUROMODULATION

Renal neuromodulation is the partial or complete incapacitation or other effective disruption of nerves innervating the kidneys. In particular, renal neuromodulation comprises inhibiting, reducing, and/or blocking neural communication along efferent and/or afferent neural fibers innervating the kidneys. Such incapacitation can be for any length of time—minutes, hours, days, weeks, months, years, or permanent. Renal neuromodulation is expected to effectively treat several clinical conditions characterized by increased overall sympathetic activity, particularly conditions associated with central sympathetic overstimulation such as hypertension, heart failure, acute myocardial infarction, metabolic syndrome, insulin resistance, diabetes, left ventricular hypertrophy, chronic and end stage renal disease, cardio-renal syndrome, osteoporosis and conditions causing sudden deaths. The reduction of afferent neural signals contributes to the systemic reduction of sympathetic drive. Renal neuromodulation can potentially benefit a variety of organs and bodily structures innervated by sympathetic nerves. For example, a reduction in central sympathetic drive may reduce insulin resistance that afflicts patients with metabolic syndrome and Type II diabetes.

Various techniques can be used to partially or completely incapacitate neural pathways such as those innervating the kidney. The application of energy to tissue by the helical push wire electrode(s) can induce one or more desired thermal heating effects on localized regions of the renal artery and adjacent regions of the renal plexus (RP), which lay within or adjacent to the adventitia of the renal artery. The application of thermal heating can achieve neuromodulation along all or a portion of the RP.

Desired effects of thermal heating may include raising the temperature of target neural fibers above a desired threshold to achieve non-ablative or ablative thermal alteration (e.g., via sustained heating and/or resistive heating). For example, the threshold temperature can be above body temperature (about 37° C.) but less than about 45° C. for non-ablative thermal alteration, or the threshold temperature can be about 45° C. or higher for ablative thermal alteration.

More specifically, exposure to thermal heating between about 37° C. and 45° C. may induce thermal alteration of the target neural fibers or of vascular structures that perfuse the target fibers. In cases where vascular structures are affected, the target neural fibers are denied perfusion, resulting in necrosis of the neural tissue. Exposure to thermal heating above 45° C. (or above 60° C. in other cases) may induce thermal ablation of the target neural fibers or the vascular structures. In some patients, it may be desirable to achieve temperatures that thermally ablate the target neural fibers or the vascular structures, but that are less than about 90° C., or less than about 85° C., or less than about 80° C., and/or less than about 75° C. Regardless of the level or type of heat exposure utilized to induce thermal neuromodulation, a reduction in renal sympathetic nerve activity ("RSNA") is expected.

II. SELECTED EMBODIMENTS OF CATHETER APPARATUSES HAVING A HELICAL PUSH WIRE ELECTRODE

FIG. 1 illustrates a system 1 in accordance with an embodiment of the present technology. The system 1 includes a renal neuromodulation system 10 ("system 10"). The system 10 includes an intravascular or intraluminal treatment device 12 that is operably coupled to an energy source or console 26. Energy source or console 26 can include, for example, an RF energy generator, a cryotherapy console, an ultrasonic signal generator or other energy source. In the embodiment shown in FIG. 1, the treatment device 12 (e.g., a catheter) includes an elongated shaft 16 having a proximal portion 18, a handle 34 at a proximal region of the proximal portion 18, and a distal portion 20 extending distally relative to the proximal portion 18. The treatment device 12 further includes a therapeutic assembly or treatment section 21 at the distal portion 20 of the shaft 16. The therapeutic assembly 21 can include a helical push wire electrode 22 and a distal electrode support section 24, which are configured to be delivered to a renal blood vessel (e.g., a renal artery) in a delivery configuration.

A lumen runs the entire length of an elongated shaft 16 where a wire (not shown) can be routed. In various embodiments, the entire wire is an electrode configured to be energized and to create a continuous helical lesion within an artery.

The material of the wire is flexible such that the pre-formed helical shape may expand and contract to different diameters so that it can be used in arteries of different sizes. In addition, the wire may have different cross-sectional shapes. For example, the wire can be a round wire, flat wire, or wire of other geometry. A flat wire allows flexibility in the radial direction (i.e., it allows the wire to expand in diameter upon deployment), yet provides greater resistance in the axial direction both of which provide more consistent contact with the artery wall which will be described in greater detail later.

Upon delivery to the target treatment site within the renal blood vessel, the therapeutic assembly 21 is further configured to be placed into a treatment or deployed state (e.g., a generally helical or spiral configuration) for delivering energy at the treatment site and providing electrically induced and/or thermally induced renal neuromodulation. In some embodiments, the therapeutic assembly 21 may be placed or transformed into the deployed state or arrangement via actuation, e.g., via an actuator 36, such as a knob, button, pin, or lever carried by the handle 34. In other embodiments, however, the therapeutic assembly 21 may be transformed between the delivery and deployed states using other suitable mechanisms or techniques.

The wire could include discrete sections of insulation along its length to allow the wire to form discrete lesions. Without insulation, the entire wire is an electrode, which, when expanded, may create a continuous helical lesion. Insulating various or selected portions of the wire creates a patterned electrode having a plurality of conductive sections separated by the insulated portions. Even though the entire wire still carries electrical current, the insulated portions or areas are restricted from delivering energy to tissues. As a result, discrete electrodes are provided to create discrete lesions. A flat or round wire electrode may include insulation on its inner surface, which would prevent RF energy dissipation into the bloodstream. As such, the electrode may provide a greater percentage of its power into the tissue, thus reducing the necessary power levels.

The proximal end of the therapeutic assembly 21 is carried by or affixed to the distal portion 20 of the elongated shaft 16. A distal end of the therapeutic assembly 21 may terminate with, for example, an atraumatic rounded tip or cap (e.g., cover 129 in FIG. 5b). Alternatively, the distal end of the therapeutic assembly 21 may be configured to engage another element of the system 10 or treatment device 12. For example, the distal end of the therapeutic assembly 21 may define a passageway for engaging a guide wire (not shown) for delivery of the treatment device using over-the-wire ("OTW") or rapid exchange ("RX") techniques.

The energy source or console 26 is configured to generate a selected form and magnitude of energy for delivery to the target treatment site via therapeutic assembly 21. The energy generator 26 can be electrically coupled to the treatment device 12 via a cable 28. At least one supply wire (not shown) passes along the elongated shaft 16 or through a lumen in the elongated shaft 16 to one or more helical push wire electrodes 22 and transmits the treatment energy to one or more helical push wire electrodes 22. In some embodiments, each helical push wire electrode 22 includes its own supply wire which would allow for each helical push wire electrode 22 to be independently energized in a sequential or exclusive manner. In other embodiments, however, two or more helical push wire electrodes 22 may be electrically coupled to the same supply wire. The supply wire may be used as a thermocouple wire and may be used to transmit temperature and impedance measurements taken at the distal cap. A control mechanism, such as foot pedal 32 or other operator control, may be connected (e.g., pneumatically connected or electrically connected) to the console to allow the operator to initiate, terminate and/or adjust various operational characteristics of the energy generator such as power delivery.

The system 10 may also include a remote control device (not shown) that can be positioned in a sterile field and operably coupled to the therapeutic assembly 21. The remote control device can be configured to allow for selective activation of the therapeutic assembly 21. For example, the remote control device can be configured to allow the operator to initiate, terminate and, optionally, adjust various operational characteristics of the energy generator. In some embodiments, a control mechanism (not shown) may be built into the handle assembly 34, allowing the operator control through the actuation of buttons, switches or other mechanisms on the handle assembly 34.

The energy source 26 can be configured to deliver the treatment energy under the control of an automated control algorithm 30, under the control of the clinician, or a combination thereof. In addition, the energy source or console 26 may include one or more evaluation or feedback algorithms 31 that can be configured to accept information and provide feedback to the clinician before, during, and/or after therapy. Feedback can be audible, visual or haptic. The feedback can be based on output from a monitoring system (not shown). The monitoring system can be a system including sensors or other monitoring devices integrated with treatment device 12, sensors or other monitoring devices separate from treatment device 12, or a combination thereof. The monitoring devices of the monitoring system can be configured to measure conditions at the treatment site (e.g., the temperature of the tissue being treated), systemic conditions (e.g., patient vital signs), or other conditions germane to the treatment, health, and safety of the patient.

Figure 2:
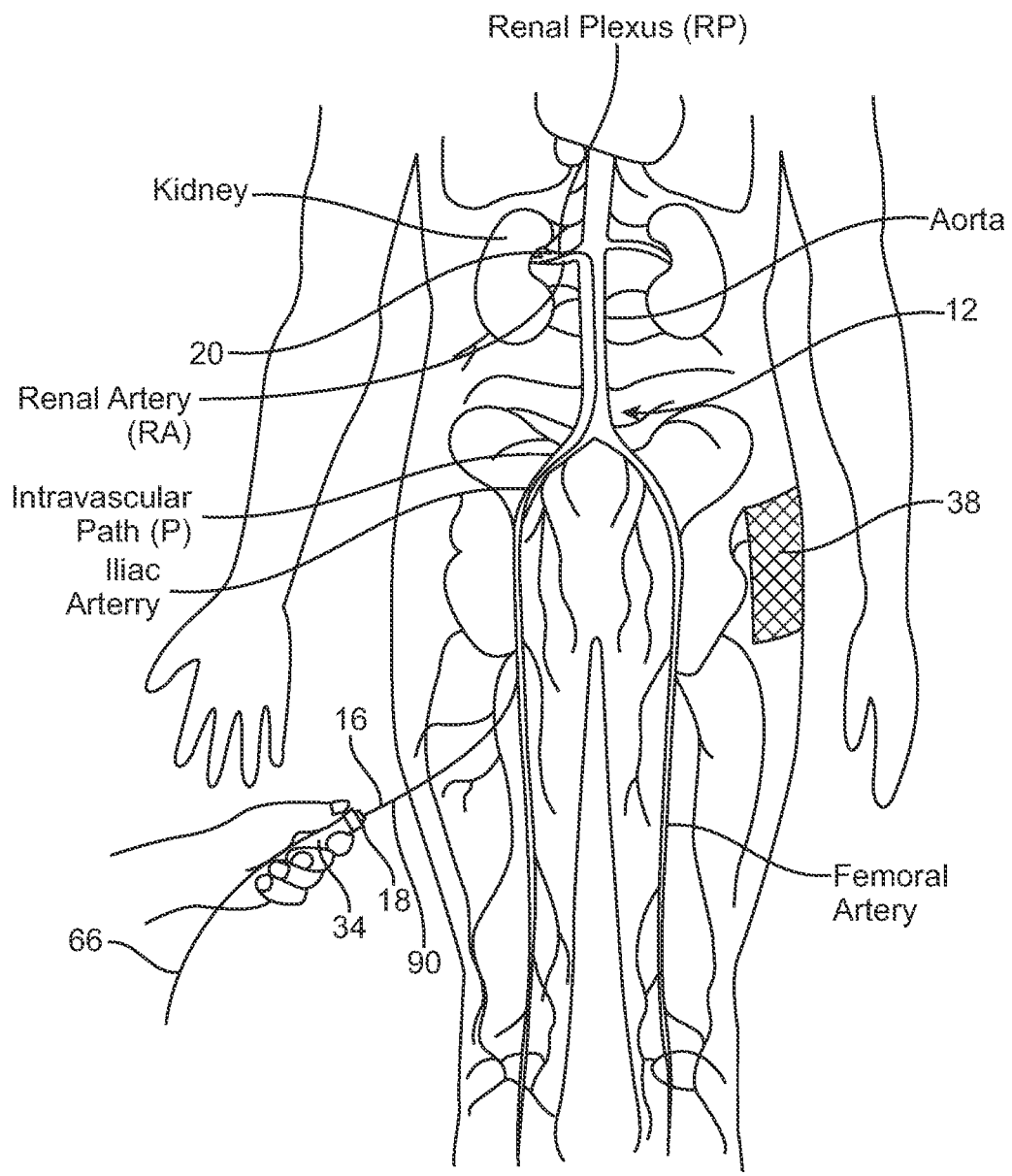
FIG. 2 is an anatomical view illustrating modulating renal nerves using a system in accordance with an embodiment of the present technology.

In some embodiments, the system 10 may be configured to provide delivery of a monopolar electric field via the helical push wire electrodes 22. In such embodiments, a neutral or dispersive electrode 38 may be electrically connected to the energy generator 26 and attached to the exterior of the patient (as shown in FIG. 2). In other embodiments, the system 10 may be configured to provide delivery of a bipolar electric field via the helical push wire electrodes 22. The helical push wire electrode 22 may deliver power between desired portions of the electrode to form a closed circuit within the artery thereby eliminating the need to use the neutral or dispersive electrode 38. Additionally, one or more sensors (not shown), such as one or more temperature (e.g., thermocouple, thermistor, etc.), impedance, pressure, optical, flow, chemical or other sensors, may be located proximate to or within the helical push wire electrodes 22 and connected to one or more supply wires (not shown). For example, a total of two supply wires may be included, in which both wires could transmit the signal from the sensor and one wire could serve dual purpose and also convey the energy to the helical push wire electrodes 22. Alternatively, a different number of supply wires may be used to transmit energy to the helical push wire electrodes 22.

The energy source 26 can further include a device or monitor that may include processing circuitry such as one or more microprocessors, and a display 33. The processing circuitry may be configured to execute stored instructions relating to the control algorithm 30. The energy source 26 may be configured to communicate with the treatment device 12 (e.g., via the cable 28) to control the neuromodulation assembly and/or to send signals to or receive signals from the monitoring system. The display 33 may be configured to indicate power levels or sensor data visually, by audio, or other means, or may be configured to communicate the information to another device. The console 26 may also be operably coupled to a catheter lab screen or system for displaying treatment information (e.g., nerve activity before and after treatment, effects of ablation, efficacy of ablation of nerve tissue, lesion location, lesion size, etc.).

The energy source or console 26 can be configured to control, monitor, supply, or otherwise support operation of the treatment device 12. In other embodiments, the treatment device 12 can be self-contained and/or otherwise configured for operation without connection to the energy source or console 26. As shown in the example of FIG. 1, the energy source or console 26 can include a primary housing having a display 33.

In some embodiments, the energy source or console 26 can include a processing device or module (not shown) having processing circuitry such as a microprocessor. The processing device can be configured to execute stored instructions relating to the control algorithm 30, the evaluation/feedback algorithm 31 and other functions. Furthermore, the energy source or console 26 can be configured to communicate with the treatment device 12 via cable 28. For example, the therapeutic assembly 21 of the treatment device 12 can include a sensor (not shown) (e.g., a recording electrode, a temperature sensor, a pressure sensor, or a flow rate sensor) and a sensor lead (not shown) (e.g., an electrical lead or a pressure lead) configured to carry a signal from the sensor to the handle 34. The cable 28 can be configured to carry the signal from the handle 34 to the energy source or console 26.

The energy source or console 26 can have different configurations depending on the treatment modality of the treatment device 12. For example, when the treatment device 12 is configured for electrode-based or transducer-based treatment, the energy source or console 26 can include an energy generator (not shown) configured to generate RF energy, pulsed energy, microwave energy, optical energy, focused ultrasound energy, heat energy, or another suitable type of energy. In some embodiments, the energy source or console 26 can include an RF generator operably coupled to one or more electrodes (not shown) of the therapeutic assembly 21.

FIG. 2 illustrates one example of modulating renal nerves with an embodiment of the system 10. In this embodiment, the treatment device 12 provides access to the renal plexus (RP) through an intravascular path (P), such as a percutaneous access site in the femoral (illustrated), brachial, radial, or axillary artery to a targeted treatment site within a respective renal artery (RA). As illustrated, a section of the proximal portion 18 of the shaft 16 is exposed outside the patient. By manipulating the proximal portion 18 of the shaft 16 from outside the intravascular path (P), the clinician may advance the shaft 16 through the intravascular path (P) and remotely manipulate the distal portion 20 of the shaft 16. Image guidance technology, for example, computed tomography (CT), fluoroscopy, intravascular ultrasound (IVUS), optical coherence tomography (OCT), or another suitable guidance modality, or combinations thereof, may be used to aid the clinician's manipulation. Furthermore, in some embodiments image guidance components (e.g., IVUS, OCT) may be incorporated into the treatment device 12.

After the therapeutic assembly 21 is adequately positioned in the renal artery (RA), it can be radially expanded or otherwise deployed using the handle 34 or other suitable means until the neuromodulation assembly is positioned at its target site and the nerve-monitoring device is in stable contact with the inner wall of the renal artery (RA). Energy is then applied from the neuromodulation assembly to induce one or more desired neuromodulating effects on localized regions of the renal artery and adjacent regions of the renal plexus (RP), which lay intimately within, adjacent to, or in close proximity to the adventitia of the renal artery (RA). The application of energy may achieve neuromodulation along all or at least a portion of the renal plexus (RP).

In some embodiments, the helical push wire electrodes 22 of the therapeutic assembly 21 may be proximate to, adjacent to, or carried by (e.g., adhered to, threaded over, wound over, and/or crimped to) a distal electrode support section 24. The proximal end of the distal electrode support section 24 is preferably coupled to the distal portion 20 of the elongated shaft 16 via a coupling (not shown). The coupling may be an integral component of the elongated shaft 16 (i.e., may not be a separate piece) or the coupling may be a separate piece such as a collar (e.g., a radiopaque band) wrapped around an exterior surface of the elongated shaft 16 to secure distal electrode support section 24 to the elongated shaft 16. In other embodiments, however, distal electrode support section 24 may be associated with the elongated shaft 16 using another arrangement and/or different features.

In some embodiments, the therapeutic assembly 21 may function with multiple helical push wire electrodes 22 associated with the same distal electrode support section 24. When multiple helical push wire electrodes 22 are provided, the helical push wire electrodes 22 may deliver power independently (i.e., may be used in a monopolar fashion), either simultaneously, selectively, or sequentially, and/or may deliver power between any desired combination of the elements (i.e., may be used in a bipolar fashion). Furthermore, a user may choose which helical push wire electrode(s) 22 are used for power delivery in order to form highly customized lesion(s) within the renal artery having a variety of shapes or patterns.

Figure 3A:
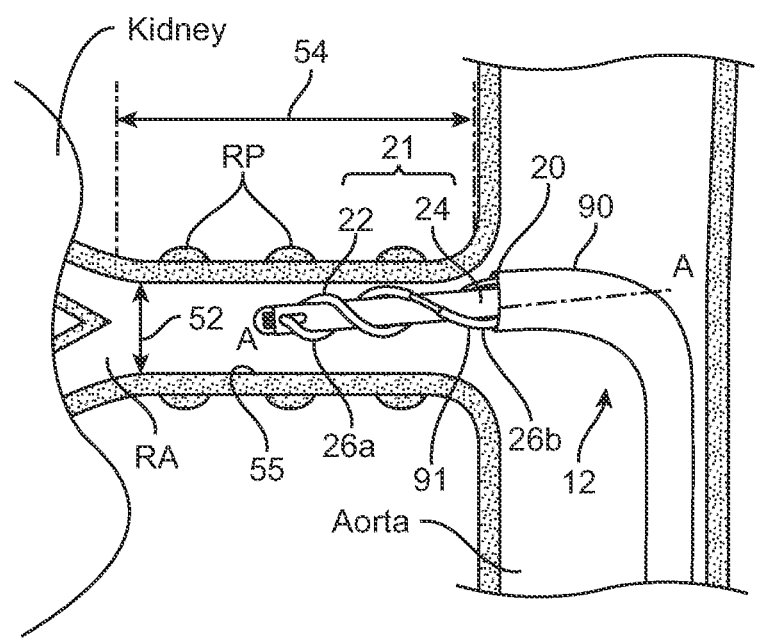
FIG. 3A is an anatomical view illustrating a distal portion of a shaft and a therapeutic assembly in a delivery state within a renal artery in accordance with an embodiment of the present technology.
Figure 3B:
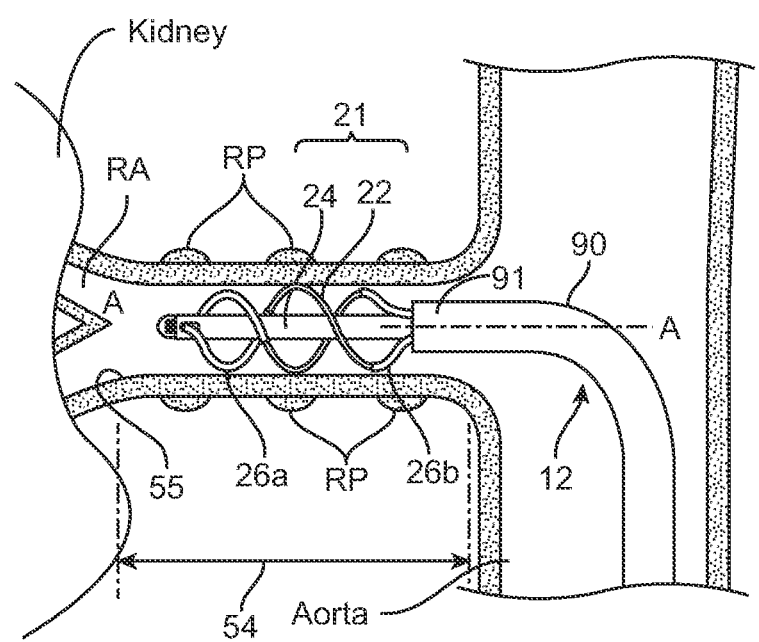
FIG. 3B is an anatomical view illustrating the therapeutic assembly shown in FIG. 3A in a deployed state within a renal artery.
Figure 3C:
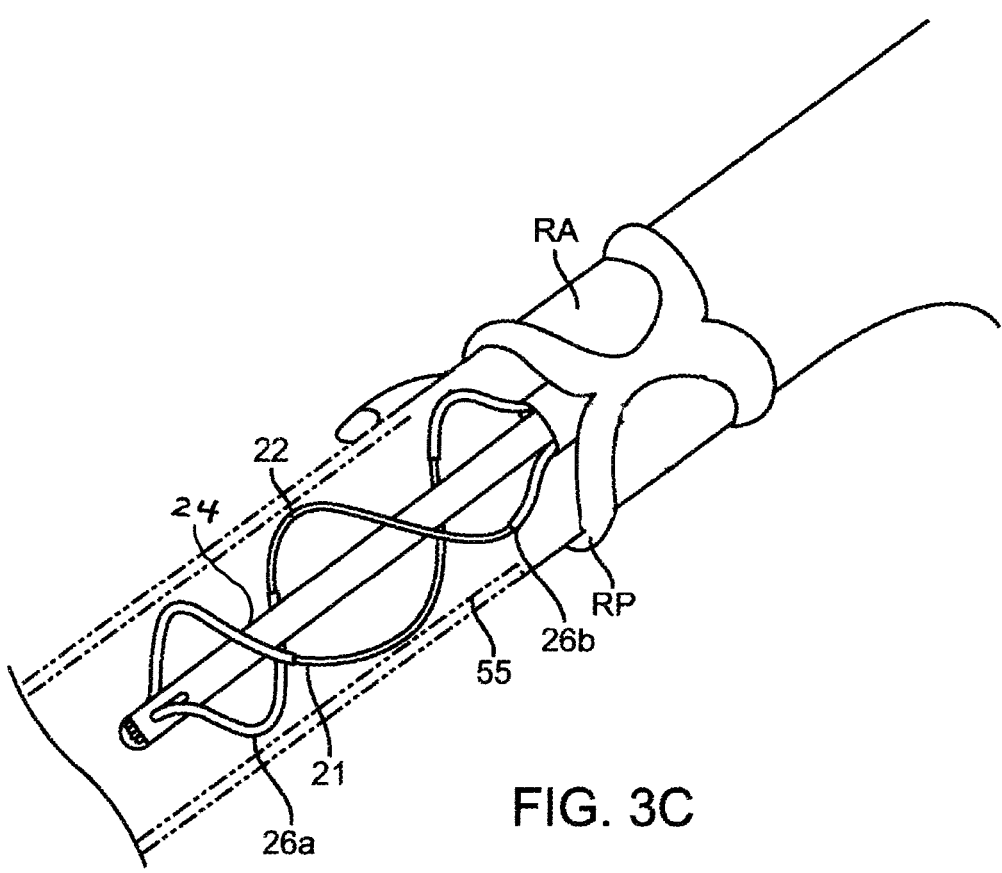
FIG. 3C is an anatomical view illustrating the therapeutic assembly shown in FIG. 3A in a deployed state within a renal artery.

FIG. 3A is a cross-sectional view illustrating one embodiment of the distal portion 20 of the shaft 16 and the therapeutic assembly 21 in a delivery state (e.g., low-profile or collapsed configuration) within a renal artery RA. FIGS. 3B and 3C illustrate the therapeutic assembly 21 in a deployed state (e.g., expanded or helical configuration) within the renal artery. Referring to FIG. 3A, the collapsed or delivery arrangement of the therapeutic assembly 21 defines a low profile about the longitudinal axis A-A of the assembly such that a transverse dimension of the therapeutic assembly 21 is sufficiently small to define a clearance distance between an arterial wall 55 and the treatment device 12. The delivery state facilitates insertion and/or removal of the treatment device 12 and, if desired, repositioning of the therapeutic assembly 21 within the renal artery RA.

In the collapsed configuration where the helical push wire electrodes 22 are in contact with the distal electrode support section 24, for example, the geometry of distal electrode support section 24 facilitates movement of the therapeutic assembly 21 through a guide catheter 90 to the treatment site in the renal artery RA. Moreover, in the collapsed configuration, the therapeutic assembly 21 is sized and shaped to fit within the renal artery RA and has a diameter that is less than a renal artery inner diameter 52 and a length (from a proximal end of the therapeutic assembly 21 to a distal end of the therapeutic assembly 21) that is less than a renal artery length 54. Furthermore, as described in greater detail below, the geometry of the support structure 24 is arranged to define a maximum transverse dimension about its central axis in the collapsed delivery state that is less than the renal artery inner diameter 52 and a maximum length in the direction of the central axis that is preferably less than the renal artery length 54. In one embodiment, the maximum diameter of the therapeutic assembly 21 in the collapsed delivery state is approximately equal to or slightly less than the interior diameter of the elongated shaft 16.

The distal portion 20 of the shaft 16 may flex in a substantial fashion to gain entrance into a respective renal artery by following a path defined by a guide catheter, a guide wire, or a sheath. For example, the flexing of distal portion 20 may be imparted by the guide catheter 90, such as a renal guide catheter with a preformed bend near the distal end that directs the shaft 16 along a desired path from the percutaneous insertion site to the renal artery RA. In another embodiment, the treatment device 12 may be directed to the treatment site within the renal artery RA by engaging and tracking a guide wire (e.g., guide wire 66 of FIG. 2) that is inserted into the renal artery RA and extends to the percutaneous access site. In operation, the guide wire preferably is delivered first into the renal artery RA and the elongated shaft 16 comprising a guide wire lumen is then passed over the guide wire into the renal artery RA. In some guide wire procedures, a tubular delivery sheath may be passed over the guide wire (i.e., the lumen defined by the delivery sheath slides over the guide wire) into the renal artery RA. Once the delivery sheath is placed in the renal artery RA, the guide wire may be removed and exchanged for a treatment catheter (e.g., treatment device 12) that may be delivered through the delivery sheath into the renal artery RA.

Furthermore, in some embodiments, the distal portion 20 can be directed or "steered" into the renal artery RA via the handle assembly 34 (FIGS. 1 and 2), for example, by an actuatable element 36 or by another control element. In particular, the flexing of the elongated shaft 16 may be accomplished as provided in U.S. patent application Ser. No. 12/545,648, "Apparatus, Systems, and Methods for achieving Intravascular, Thermally-Induced Renal Neuromodulation" to Wu et al., which is incorporated herein by reference in its entirety. Alternatively, or in addition, the treatment device 12 and its distal portion 20 may be flexed by being inserted through a steerable guide catheter (not shown) that includes a preformed or steerable bend near its distal end that can be adjusted or re-shaped by manipulation from the proximal end of the guide catheter.

The maximum outer dimensions (e.g., diameter) of any section of the treatment device 12, including elongated shaft 16 and the helical push wire electrodes 22 of the therapeutic assembly 21 can be defined by an inner diameter of the guide catheter 90 through which the device 12 is passed. In one particular embodiment, for example, an 8 French guide catheter having, for example, an inner diameter of approximately 0.091 inch (2.31 mm) may be used as a guide catheter to access the renal artery. Allowing for a reasonable clearance tolerance between helical push wire electrodes 22 and the guide catheter, the maximum outer dimension of the therapeutic assembly 21 is generally less than or equal to approximately 0.085 inch (2.16 mm).

After locating the therapeutic assembly 21 at the distal portion 20 of the shaft 16 in the renal artery RA, the therapeutic assembly 21 is transformed from its delivery state to its deployed state or deployed arrangement. The transformation may be initiated using an arrangement of device components as described herein with respect to the particular embodiments and their various modes of deployment. As described in greater detail below and in accordance with one or more embodiments of the present technology, the therapeutic assembly may be deployed by a control member. The control member may be, for example, a guide wire, a shaft or stylet engaged internally or externally with the support structure of the therapeutic assembly to apply a deforming or shaping force to the assembly to transform it into its deployed state. Further, the modality used to transform the therapeutic assembly 21 from the delivery state into the deployed state may, in various embodiments, be reversed to transform the therapeutic assembly 21 back to the delivery state from the deployed state.

Pulling the wire in tension from the proximal end of the catheter collapses the helix into a delivery configuration for delivery into the renal artery. Once in position, the wire is pushed in compression from the proximal end of the catheter and the wire is forced to expand into a preformed helical shape making contact with the renal artery wall. RF energy may be delivered to the wire and a helical lesion is formed.

Further manipulation of the helical push wire electrodes 22 within the respective renal artery RA establishes apposition of the therapeutic assembly 21 against the tissue along an interior wall of the respective renal artery RA. For example, as shown in FIGS. 3B and 3C, the therapeutic assembly 21 is expanded within the renal artery RA such that the helical push wire electrodes 22 are in contact with the renal artery wall 55. In some embodiments, manipulation of the proximal portion may facilitate contact between the helical push wire electrodes 22 and the wall of the renal artery. The helical push wire electrodes 22 are operated such that the contact force between the renal artery inner wall 55 and the helical push wire electrodes 22 does not exceed a maximum value. For example, the deployment mechanism may comprise a gauge to ensure that the contact force between the therapeutic assembly 21 and the artery wall 55 is less than a predetermined value for arteries of different sizes. In addition, the helical push wire electrodes 22 and the distal electrode support section 24 may provide for a consistent contact force against the arterial wall 55 that may allow for consistent lesion formation.

Figure 4A:
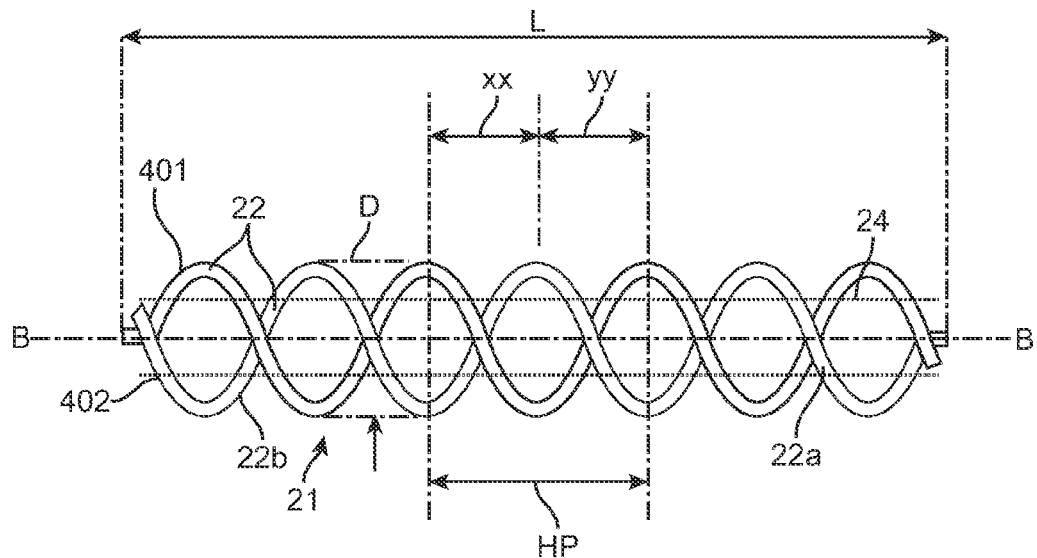
FIG. 4A is a plan view illustrating a therapeutic assembly in accordance with an embodiment of the present technology.

The alignment may also include alignment of geometrical aspects of the helical push wire electrodes 22 with the renal artery wall 55. In various embodiments, a helical push wire electrode may be surrounded by a proximal sleeve and/or a 26b distal sleeve 26a. The proximal sleeve and the distal sleeve may be positioned such that the electrode remains as close to the central longitudinal axis of the helix as possible when exiting from the proximal shaft section. In another embodiment, the helical push wire electrodes 22 may have a non-rounded shape with an active surface can be aligned such that the active surface is in contact with the artery wall 55. Such alignment may be provided by the proximal sleeve 26b. For example, the shape of the electrode and the dimensions of the distal sleeve 26a and/or the proximal sleeve 26b may be selected such that the electrode 22 fits snugly into the sleeves 26A and/or 26b and is prevented from twisting. As best seen in FIGS. 3B and 3C, in the deployed state, the therapeutic assembly 21 defines substantially helical push wire electrodes 22, when expanded, in contact with the renal artery wall 55 along a helical path. One advantage of this arrangement is that pressure from the helical structure can be applied to a large range of radial directions without applying pressure to a circumference of the vessel. Thus, the helically-shaped therapeutic assembly 21 is expected to provide stable contact between the helical push wire electrodes 22 and the artery wall 55 when the wall moves in any direction. Still another feature of the expanded helical structure is that it may contact the vessel wall in a large range of radial directions and maintain a sufficiently open lumen in the vessel allowing blood to flow through the helix during therapy. The helical push wire electrodes 22 may also be well suited for tortuous anatomy. Because the helical push wire electrodes 22 are flexible, they can be manipulated through bends in arteries, and, when positioned, can still expand and create good contact with the inner lumen of the arteries. As illustrated in FIG. 3B, in the deployed state, the helical push wire electrodes 22 define a maximum axial length of the therapeutic assembly 21 that is approximately equal to or less than a renal artery length 54 of a main renal artery (i.e., a section of a renal artery proximal to a bifurcation). Because this length can vary from patient to patient, it is envisioned that the deployed helical push wire electrodes 22 may be fabricated in different sizes (e.g., with varying lengths L and/or diameters D as shown in FIG. 4A) that may be appropriate for different patients. Referring to FIGS. 3B and 3C, in the deployed state, the helical-shaped therapeutic assembly 21 provides circumferentially continuous contact between the helical push wire electrodes 22 and the inner wall 55 of the renal artery RA. That is, the helical path may comprise a partial arc (i.e., <360°), a complete arc (i.e., 360°) or a more than complete arc (i.e., >360°) along the inner wall of a vessel about the longitudinal axis of the vessel. In some embodiments, however, the arc is not substantially in one plane normal to the central axis of the artery, but instead preferably defines an obtuse angle with the central axis of the artery. The helical-shaped therapeutic assembly 21 may also provide circumferentially discrete lesions by including discrete sections of insulation along its length to allow the wire to form discrete lesions. Insulating various or selected portions of the wire creates a patterned electrode having a plurality of conductive sections separated by the insulated portions. The entire helical push wire electrodes 22, when deployed, create a circumferentially continuous contact with the inner wall 55 of the renal artery. The insulated portions or areas are restricted from delivering energy to tissues despite still making contact with the inner wall 55. As a result, the non-insulated portions or areas delivers energy to tissues and discrete lesions are created.

In various embodiments, the helical push wire electrodes 22 may be formed of electrically conductive materials such as pre-shaped nitinol wire, cable, or tubing. A deployed electrode 22, in helical structure, may form a contact region with the renal artery wall. In this configuration, the helical electrode 22 is capable of producing a continuous helical lesion. Referring to FIG. 3E, in some embodiments, the helical push wire electrode 22 may comprise sensors 37 positioned on, in, and/or proximate to the electrodes 22 and may be electrically connected to supply wires 35. Supply wires 35 connect the electrodes to an energy source (not shown) and deliver energy (e.g., RF electrical current) to the electrodes 22.

A. The Helical Structure

Figure 4B:
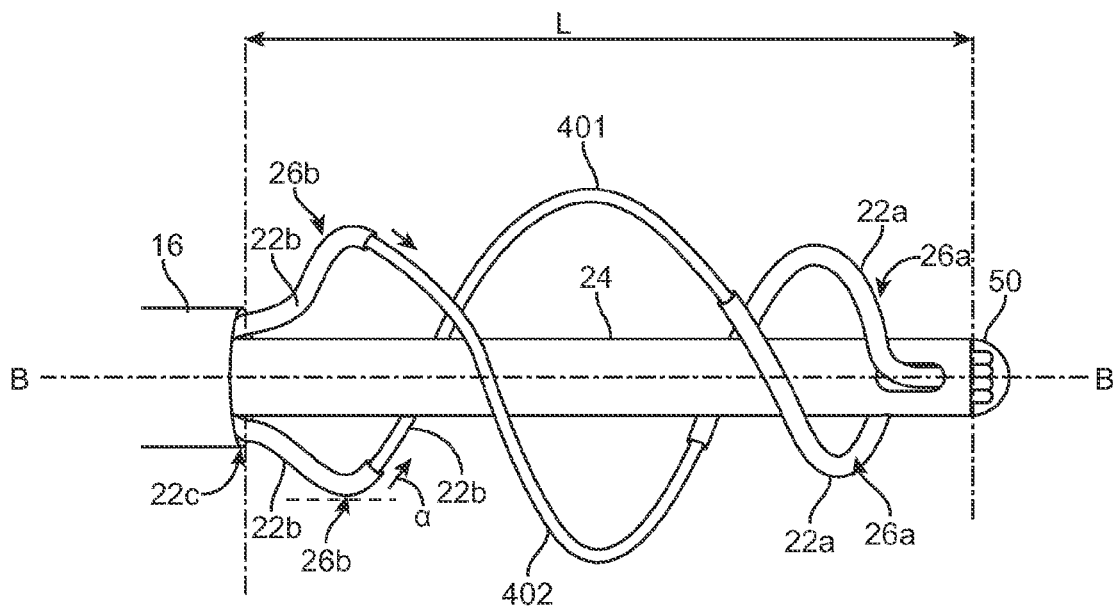
FIG. 4B is a profile view illustrating a therapeutic assembly in accordance with an embodiment of the present technology.

FIG. 4A is a plan view of an embodiment of a therapeutic or treatment assembly 21 for use with a treatment device (e.g., treatment device 12) in accordance with an embodiment of the technology, and FIG. 4B is an isometric view of the therapeutic assembly 21 of FIG. 4A. Various embodiments may comprise multiple helical push wire electrodes to create multiple helical lesions. For example, in the illustrated example, the treatment assembly 21 comprises helical push wire electrodes 401 and 402. The therapeutic assembly 21 may comprise a plurality of helical push wire electrodes. The helical electrodes 401 and 402 wind around the distal electrode support section and are axially and radially spaced from one another.

The helical push wire electrodes 401 and 402 may exit the elongated shaft 16 at its distal end through proximal sleeves 26b. Beyond the proximal sleeves 26b, the helical push wire electrodes 401 and 402 may wind around the distal electrode support section 24 in a helical shape. The proximal sleeves 26b may be fixed to the elongated shaft 16 and the distal electrode support section 24. The distal end of the helical push wire electrodes 401 and 402 are fixed to the distal end of the distal electrode support section 24, which is also the distal end of the therapeutic assembly 21 (shown in FIG. 1).

As shown in FIGS. 4A and 4B, a helix may be characterized, at least in part, by its overall diameter D, length L, helix angle α (an angle between a tangent line to the helix and its axis), pitch HP (longitudinal distance of one complete helix turn measured parallel to its axis), and number of revolutions (number of times the helix completes a 360° revolution about its axis).

In particular, the deployed or expanded configuration of the helix may be characterized by its axial length L along the axis of elongation in free space, e.g., not restricted by a vessel wall or other structure. In some embodiments, the distal tip of the electrode 22a is fixed to the distal electrode support section 24 and the exit point 22c of the electrode from the shaft 16 is also fixed. Accordingly, the exit point 22c of the electrode from the shaft 16 is a fixed distance L away from the distal end of the distal support section 24. As the helical push wire electrode 22 radially expands from its delivery state, its diameter D increases and its length L remains constant. A constant length distal section can work well for short renal arteries where the length may not accommodate insertion and elongation for expansion or deployment of a therapeutic device. Further, the pitch of the helix can be fixed, (i.e., the number of turns on the helix can be fixed regardless of the patient anatomy).

In one embodiment, the distal end portions 22a of the helical electrodes 401 and 402 are fixedly coupled to the distal end of the therapeutic assembly, which is also the distal end of the distal electrode support section. Pulling the wire and thereby creating tension from the proximal end of the catheter collapses the helix into the delivery configuration for delivery into the renal artery. Once in position, the wire is pushed and thereby compressed from the proximal end of the catheter, causing the wire to expand into a helical shape that makes contact with the renal artery wall. RF energy is delivered to the wire and a helical lesion is formed.

Referring to FIG. 4B, the deployed helical electrodes 22 may comprise an atraumatic (e.g., rounded) tip 50. The tip 50 may reduce the risk of injuring the blood vessel as the helical structure is advancing and expanding and/or as a delivery sheath is retracted, and may facilitate alignment of the helical structure in a vessel as it expands. The tip 50 can be made from a polymer or metal that is fixed to the end of the structural element by adhesive, welding, crimping, over-molding, and/or soldering. In other embodiments, the tip 50 may be made from the same material as the structural element and fabricated into the tip 50 by machining or melting. In further embodiments, the tip 50 may comprise an energy delivery element or a radiopaque marker.

As shown in FIG. 4B, the proximal sleeves 26b surround the proximal portions 22b of the helical electrodes 401 and 402. The distal sleeves 26a surround the distal portions 22a of the helical electrodes 401 and 402. The proximal sleeves 26b and/or the distal sleeves 26a may be positioned as close as possible to the surface of the distal electrode support section. Accordingly, the proximal sleeves and/or the distal sleeves may uphold the helical shape when the electrodes are deployed. When transitioning from the delivery configuration to the deployment configuration, the proximal portions 22b and the distal portions 22a may move away from the central longitudinal axis. Especially when the helical electrodes 401 and 402 expand, the electrodes tend to expand away from the central axis as opposed to having an intertwined set of helical shapes.

In addition, the proximal sleeves 26b prevent the proximal portions 22b from buckling and forming a sharp angle, which may increase the friction between the therapeutic assembly and the artery wall. The proximal sleeve is shaped to allow the wire to exit at a predetermined exit angle, for example,)(0-30° from the proximal shaft section. The proximal sleeve may be sufficiently flexible to allow it to collapse onto the distal electrode support section 24, yet stiff enough to provide control of the exit angle. The proximal sleeve 26b may be more flexible than shaft 16 and less flexible than proximal electrode portion 22b. The proximal sleeves 26b and/or the distal sleeves 26a may also provide lubrication or a low-friction surface to allow sliding the wire to expand or contract the helical structure. The proximal sleeves 26b and the distal sleeves 26a may be formed from biocompatible metals and/or polymers, including polyethylene terephthalate (PET), polyamide, polyimide, polyethylene block amide copolymer, polypropylene, or polyether ether ketone (PEEK) polymers. The proximal sleeves 26b and the distal sleeves 26a may further insulate the wire to prevent energy from being dissipated into the bloodstream and from being wasted. In some embodiments, the distal sleeves 26a may not be a separate sleeve (i.e. tubular structure with a lumen) at all but could be a coating or lamination (e.g., a parylene lining) around the push wire electrode.

Referring to FIGS. 4A and 4B (and with reference to FIGS. 3A and 3B), the dimensions of the deployed helically shaped structure 22 are influenced by its physical characteristics and its configuration (e.g., expanded vs. unexpanded), which in turn may be selected with renal artery geometry in mind. For example, the axial length L of the deployed helical structure may be selected to be no longer than a patient's renal artery (e.g., the length 54 of renal artery RA of FIGS. 3A and 3B). For example, the distance between the access site and the ostium of the renal artery (the distance from a femoral access site to the renal artery is typically about 40 cm to about 55 cm) is generally greater than the length of a renal artery from the aorta and the most distal treatment site along the length of the renal artery, which is typically less than about 7 cm. Accordingly, it is envisioned that the elongated shaft 16 is at least 40 cm and the helical structure is less than about 7 cm in its the axial length L. A length of no more than about 4 cm may be suitable for use in a large population of patients. However, a shorter length (e.g., less than about 2 cm) may be used in patients with shorter renal arteries. The helical structure 22 may also be designed to work with typical renal artery diameters. For example, the diameter 52 (FIG. 3A) of the renal artery RA may vary between about 2 mm and about 10 mm.

In one embodiment, a section of or the entire helical push wire electrode of the therapeutic assembly 21, when allowed to fully deploy to an unconstrained configuration (i.e., outside of the body as shown in FIGS. 4A and 4B), comprises a helical shape having a diameter D less than about 15 mm (e.g., about 12 mm, 10 mm, 8 mm, or 6 mm); a length L less than or equal to about 40 mm (e.g., less than about 25 mm, less than about 20 mm, less than about 15 mm); a helix angle α of between about 20° and 75° (e.g., between about 35° and 55°); a range of revolutions between 0.25 and 6 (e.g., between 0.75 and 2, between 0.75 and 1.25); and a pitch HP between about 5 mm and 20 mm (e.g., between about 7 mm and 13 mm). In another example, the therapeutic assembly 21 may be configured to expand radially from its delivery state with a diameter about its central axis being approximately 10 mm to a delivery state in which the entire or a portion of the helical push wire electrode 22 are in contact with the artery wall. The foregoing dimensions and angles are associated with specific embodiments of the technology, and it will be appreciated that therapeutic assemblies configured in accordance with other embodiments of the technology may have different arrangements and/or configurations.

In some embodiments, the deployed helical push wire electrode 22 may be generally cylindrical (i.e., a helical diameter can be consistent along a majority of its length). The helical push wire electrode 22, however, may have a conical helical shape, a tapered structural element, a clockwise or counter-clockwise pathway, and consistent or varied pitch.

In one embodiment, the distal electrode support section 24 can include a solid structural element, such as, a wire, tube, or coiled or braided cable. The distal electrode support section 24 may be formed from biocompatible metals and/or polymers, including polyethylene terephthalate (PET), polyamide, polyimide, polyethylene block amide copolymer, polypropylene, or polyether ether ketone (PEEK) polymers. In some embodiments, the distal electrode support section 24 may be electrically nonconductive, electrically conductive (e.g., stainless steel, nitinol, silver, platinum, nickel-cobalt-chromium-molybdenum alloy), or a combination of electrically conductive and nonconductive materials. In one particular embodiment, for example, the distal electrode support section 24 may be formed of a pre-shaped material, such as spring temper stainless steel or nitinol.

Generally, the helical push wire electrode 22 may be designed to apply a desired outward radial force to the renal artery wall 55 (FIGS. 3A and 3B) when inserted and expanded to contact the inner surface of the renal artery wall 55 (FIGS. 3A and 3B). The radial force may be selected to avoid injury to the patient from stretching or distending the renal artery RA when the helical push wire electrode 22 is expanded against the artery wall 55. Radial forces that may avoid injuring the renal artery RA yet provide adequate stabilization force may be determined by calculating the radial force exerted on an artery wall by typical blood pressure. For example, a suitable radial force may be less than or equal to about 300 mN/mm (e.g., less than 200 mN/mm). Factors that may influence the applied radial force include the geometry and the stiffness of the helical push wire electrode 22. In one particular embodiment, the helical push wire electrode 22 is about 0.003-0.020 inch (0.08-0.51 mm) in diameter. Depending on the composition of the helical push wire electrode 22, the structural element diameter may be selected to facilitate a desired conformability and/or radial force against the renal artery when expanded. The outward pressure of the helical push wire electrode 22 may be assessed by an associated pressure transducer.

In addition, certain secondary processes, including heat treating and annealing may harden or soften the fiber material to affect strength and stiffness. In particular, for shape-memory alloys such as nitinol, these secondary processes may be varied to give the same starting material different final properties. For example, the elastic range or softness may be increased to impart improved flexibility. The secondary processing of shape memory alloys influences the transition temperature, that is, the temperature at which the structure exhibits a desired radial strength and stiffness. In embodiments that employ shape memory properties, the transition temperature may be set at normal body temperature (e.g., around 37° C.) or in a range between about 37° C. and 45° C. In other embodiments that comprise super elastic nitinol, a transition temperature can be well below body temperature, for example below 0° C. Alternatively, the helical structure may be formed from an elastic or super elastic material such as nitinol that is thermally engineered into a desired helical shape. Alternatively, the helical push wire electrode 22 may be formed from multiple materials such as one or more metals. Various embodiments may be made of cored materials, such as, for example, materials having a core of a first metal and an outer shell of a second metal (e.g., Nitinol/tantalum and SST/Nitinol). As illustrated in FIG. 3F, a round cored wire 300a and a flat cored wire 300b may be made having a tantalum core and a Nitinol outer layer. Although these examples show cores 302, 304 made of the tantalum and outer layers 301, 303 made of Nitinol, other materials can be used.

Referring back to FIGS. 3B and 3C, it should be understood that the helical push wire electrode 22 of the treatment assembly 21, when not inserted into a patient, is capable of deploying to a maximum diameter that is larger than the diameter in its delivery state. Further, the helical push wire electrode 22 may be sized so that the maximum diameter is larger than the lumen diameter 52 of the renal artery RA. When inserted into a patient and transformed to the deployed state, however, the helical push wire electrode 22 expands radially to span the renal artery lumen and, at its largest circumferential section, is approximately or slightly less than the diameter 52 of the renal artery RA. A slight amount of vessel distension may be caused without undue injury and the electrode 22 may expand such that its largest circumferential section is slightly more than the diameter 52 of the renal artery RA, or such that one or more portions of the electrode are slightly pressed into the wall 55 of the renal artery RA. A helically-shaped assembly or array that causes slight and non-injurious distension of an artery wall 55 may advantageously provide stable contact force between the helical push wire electrode 22 and the artery wall 55 and/or hold the helical push wire electrode 22 in place even as the artery moves with respiratory motion and pulsing blood flow. Because this diameter 52 of the renal artery RA varies from patient to patient, the treatment assembly 21 may be capable of assuming a range of diameters between the delivery diameter and the maximum diameter.

As provided above, one feature of the deployed therapeutic assembly 21 in the helical configuration is that one or more portions of the helical push wire electrode 22 may be placed into stable contact with a vessel wall to reliably create consistent lesions. Further, the helical push wire electrode 22 may be designed with appropriate spacing between each winding to achieve a desired lesion configuration within the target vessel. Another feature of several embodiments of the therapeutic assembly 21 having the helical configuration described above is that the assembly may be expanded to fit within a relatively wide range of different vessel diameters and/or with various tortuosities.

It should be understood that the embodiments provided herein may be used in conjunction with one or more helical push wire electrodes 22. As described in greater detail below, the helical push wire electrodes 22, when deployed, is configured to provide energy delivery to the renal artery without any repositioning. In some patients, it may be desirable to create a single lesion or multiple focal lesions that are spaced around the circumference of the renal artery. A single focal lesion with desired longitudinal and/or circumferential dimensions, one or more full-circle lesions, multiple circumferentially spaced focal lesions at a common longitudinal position, spiral-shaped lesions, interrupted spiral lesions, generally linear lesions, and/or multiple longitudinally spaced discrete focal lesions at a common circumferential position may be created. In still further embodiments, lesions having a variety of other geometric shapes or patterns may be created. The wire could include varying insulation along its length to allow the wire to create more discrete lesions. A patterned electrode having a plurality of conductive sections separated by the insulated portions may be created by insulating various or selected portions of the wire. The insulated portions or areas are restricting delivering of energy to tissues and thus discrete lesions may be created by the un-insulated portions.

Depending on the size and shape of the helical push wire electrodes 22, the formed lesions may be spaced around the circumference of the renal artery and the same formed lesions also may be spaced along the longitudinal axis of the renal artery. In particular embodiments, it is desirable for each formed lesion to cover at least 10% of the vessel circumference to increase the probability of affecting the renal plexus. Furthermore, to achieve denervation of the kidney, it is considered desirable for the formed lesion pattern, as viewed from a proximal or distal end of the vessel, to at least extend approximately all the way around the circumference of the renal artery. Therefore, each formed lesion covers an arc of the circumference, and each of the lesions, as viewed from an end of the vessel, abut or overlap adjacent or other lesions in the pattern to create either an actual circumferential lesion or a virtually circumferential lesion. The formed lesions defining an actual circumferential lesion lie in a single plane perpendicular to a longitudinal axis of the renal artery. A virtually circumferential lesion is defined by multiple lesions that may not all lie in a single perpendicular plane, although more than one lesion of the pattern can be so formed. At least one of the formed lesions comprising the virtually circumferential lesion is axially spaced apart from other lesions. In one example, a virtually circumferential lesion can comprise six lesions created in a single helical pattern along the renal artery such that each lesion spans an arc extending along at least one sixth of the vessel circumference such that the resulting pattern of lesions completely encompasses the vessel circumference when viewed from an end of the vessel. In other examples, however, a virtually circumferential lesion can comprise a different number of lesions. It is also desirable that each lesion be sufficiently deep to penetrate into and beyond the adventitia to affect the renal plexus. However, lesions that are too deep (e.g., >5 mm) run the risk of interfering with non-target tissue and tissue structures (e.g., a renal vein). Therefore, a controlled depth of energy treatment is also desirable.

As shown in FIGS. 4A and 4B, electrodes 22 may be configured as such that a desired arrangement of lesions is formed. For example, the axial distances between the deployed helical electrodes 22 may be selected so that the edges of the lesions formed by one or more portions of the helical electrodes 22 on the renal artery wall 55 are overlapping or non-overlapping. One or both of the axial distances xx or yy may be about 2 mm to about 10 mm. In one embodiment, the axial distances xx or yy may be in the range of about 2 mm to about 5 mm. The axial distance xx may be less than, about equal to, or greater than the axial distance yy.

Referring to FIG. 3B, in the illustrated example, multiple helical electrodes 22 are connected to the energy generator 26 (FIG. 1) and are sized and configured to contact an internal wall of the renal artery. In other embodiments, each helical electrode 22 may be powered separately. In the illustrated example, the helical push wire electrodes 22 may be operated in a monopolar or unipolar mode. In this arrangement, a return path for the applied RF electric field is established, e.g., by an external dispersive electrode (shown as element 38 in FIGS. 1 and 2), also called an indifferent electrode or neutral electrode. The monopolar application of RF electric field energy serves to ohmically or resistively heat tissue in the vicinity of the electrode. The application of the RF electrical field thermally injures tissue. The treatment objective is to thermally induce neuromodulation (e.g., necrosis, thermal alteration or ablation) in the targeted neural fibers. The thermal injury forms a lesion in the vessel wall. Alternatively, a RF electrical field may be delivered with an oscillating or pulsed intensity that does not thermally injure the tissue. In that case, neuromodulation in the targeted nerves is accomplished by electrical modification of the nerve signals.

The active surface area of the helical push wire electrode 22 is defined as the energy transmitting area that may be placed in intimate contact against tissue. Too much contact area between the electrode and the vessel wall may cause excessively high temperatures at or around the interface between the tissue and the electrode, thereby generating excessive heat. Excessive heat may create a lesion that is circumferentially too large. This may also lead to an undesirable thermal application to the vessel wall. In some instances, too much contact can also lead to small, shallow lesions. Too little contact between the electrode and the vessel wall may result in superficial heating of the vessel wall, thereby creating a lesion that is too small (e.g., <10% of vessel circumference) and/or too shallow.

The active surface area of contact (ASA) between the electrode 22 and the inner vessel wall (e.g., renal artery wall 55) affects the efficiency and control of the generation of a thermal energy field across the vessel wall to thermally affect targeted neural fibers in the renal plexus. While the ASA of the electrode is important for creating lesions of desirable size and depth, the ratio between the ASA and total surface area (TSA) of the helical push wire electrode 22 and electrode 46 is also important. The ASA to TSA ratio influences lesion formation in two ways: (1) the degree of resistive heating via the electric field, and (2) the effects of blood flow or other convective cooling elements such as injected or infused saline. For example, an RF electric field causes lesion formation via resistive heating of tissue exposed to the electric field. The higher the ASA to TSA ratio (i.e., the greater the contact between the electrode and tissue), the greater the resistive heating, e.g., the larger the lesion that is formed.

Figure 3D:
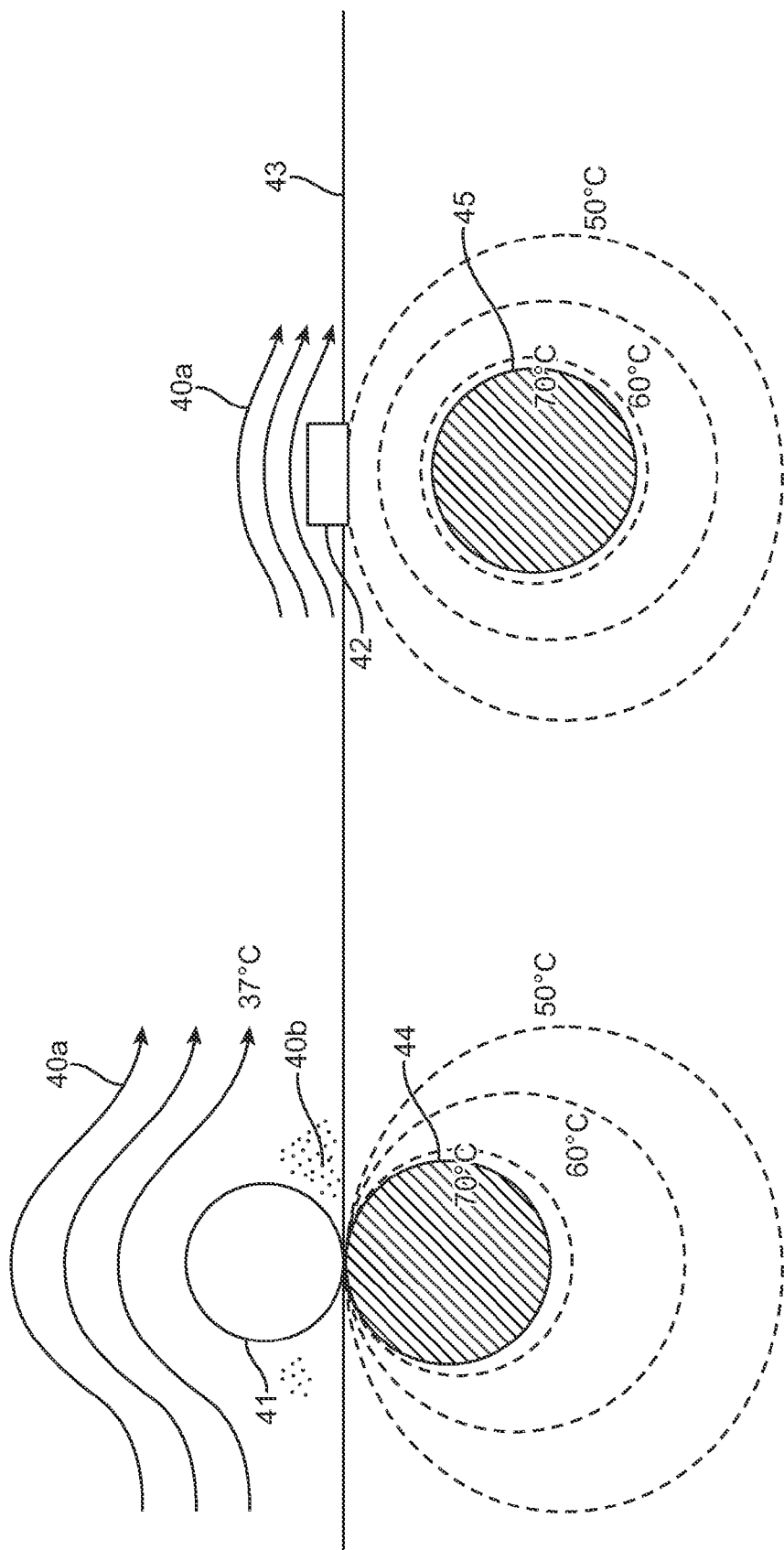
FIG. 3D is a cross-sectional end view illustrating two electrodes having different cross-sectional shapes producing different temperature zones in accordance with an embodiment of the present technology.
Figure 3E:
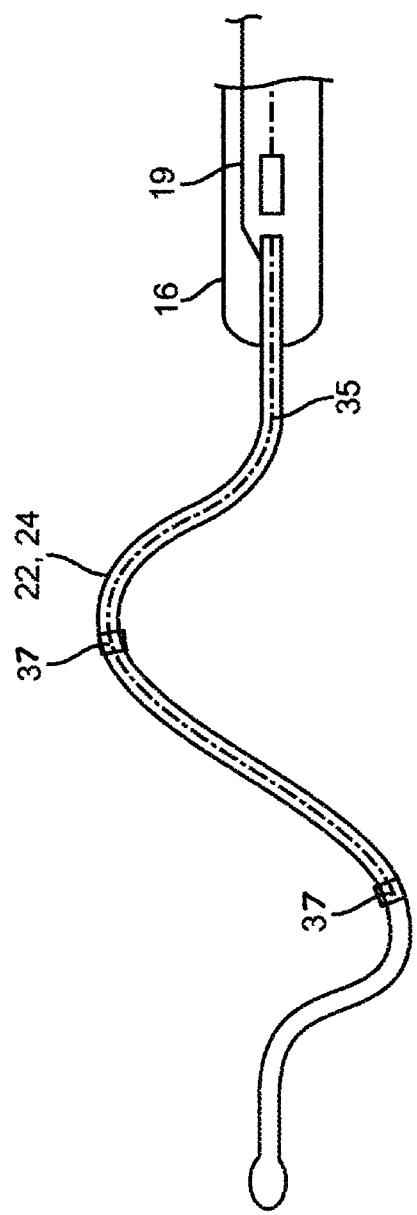
FIG. 3E is a profile view of a helical push wire electrode including sensors in accordance with an embodiment of the present technology.

FIG. 3D illustrates an example profile of two electrodes having different cross sectional shapes, and the temperature zones created as a result of RF energy radiated by the two differently shaped electrodes. The electrode 41 is representative of a round-wire electrode and the electrode 42 is representative of a flat-wire electrode. As illustrated, the electrodes 41 and 42 are provided, for example, to emit RF energy to create ablation. The temperature of the blood is 37° C., which is lower than the operating temperature of the electrodes 41 and 42. Accordingly, the flow of blood 40a carries away some of the heat generated by the electrodes 1 and 2. Further, due to the stagnancy of the blood 40b near the vessel wall with electrode 1, the temperature of the tissue close to the surface of the artery 43 may rise significantly as a result of gathering heat generated by the electrode 41. As a result, the desired temperature zone 44 tends to be closer to the surface of the artery 43 and a shallower lesion will be created. In contrast, the desired temperature zone 45 of the electrode 42 is deeper. Accordingly, because most of the nerves are 2-3 mm away from the surface of the artery, with the same amount of energy, the electrode 42 may provide a better (i.e., the lesion is closer to the nerve, larger or deeper) linear ablation than the electrode 41. The electrode 42 may also reduce the risk of charring the surface of the artery 43.

In addition, a flat wire allows flexibility in the radial direction. Therefore, it allows the wire to expand in diameter upon deployment but causes less pressure on the inner artery lumen than a round wire. The flexibility also allows it to conform better to non-symmetric arteries when making contact than the round-wire electrode 41. Because the flat geometry inherently provides resistance to twisting, more consistent contact of the flat surface with the artery wall can be maintained. As described above with reference to FIG. 3D, the flat-wire electrode 42 is more flexible in the radial dimension, and causes less pressure on the inner artery lumen. It also conforms better to non-symmetric arteries when making contact than the round-wire electrode 41. Further, the flat-wire electrode 42 maintains a more consistent pitch in the helical structure when expanded due to more contact area with the artery wall. This can be understood by considering that a structure with a cross section having a width greater than its height will, respond differently to a force applied normal to its width than it will to the same magnitude of force applied normal to its height. Particularly, the wire will require less force to flex in the direction of its height, than it will to flex in the direction of the width.

The flow of blood over the non-contacting portion of the electrode (that is, the TSA minus the ASA) provides conductive and convective cooling of the electrode, thereby carrying excess thermal energy away from the interface between the vessel wall and electrode. If the ratio of ASA to TSA is too high (e.g., more than 50%), resistive heating of the tissue may be too aggressive and not enough excess thermal energy may be carried away, resulting in excessive heat generation and the increased potential for stenotic injury, thrombus formation and undesirable lesion size. If the ratio of ASA to TSA is too low (e.g., 10%), then there is too little resistive heating of tissue, thereby resulting in superficial heating and smaller and shallower lesions. In a representative embodiment, the ASA of the electrode contacting tissue may be expressed as 0.25 TSA≤ASA≤0.50 TSA. An ASA to TSA ratio of over 50% may still be used without excessive heat generation by compensating with a reduced power delivery algorithm and/or by using convective cooling of the electrode by exposing it to blood flow. Electrode cooling can be achieved by injecting or infusing cooling liquids such as saline (e.g., room temperature saline or chilled saline) over the electrode and into the blood stream.

III. SELECTED EMBODIMENTS OF RENAL DENERVATION SYSTEMS

The representative embodiments provided herein include features that may be combined with one another and with the features of other disclosed embodiments. In an effort to provide a concise description of these embodiments, not all features of an actual implementation are described in the specification. It should be appreciated that in the development of any such actual implementation, as in any engineering or design project, numerous implementation-specific decisions should be made to achieve the developers' specific goals, such as compliance with system-related and business-related constraints, which may vary from one implementation to another.

Figure 5A:
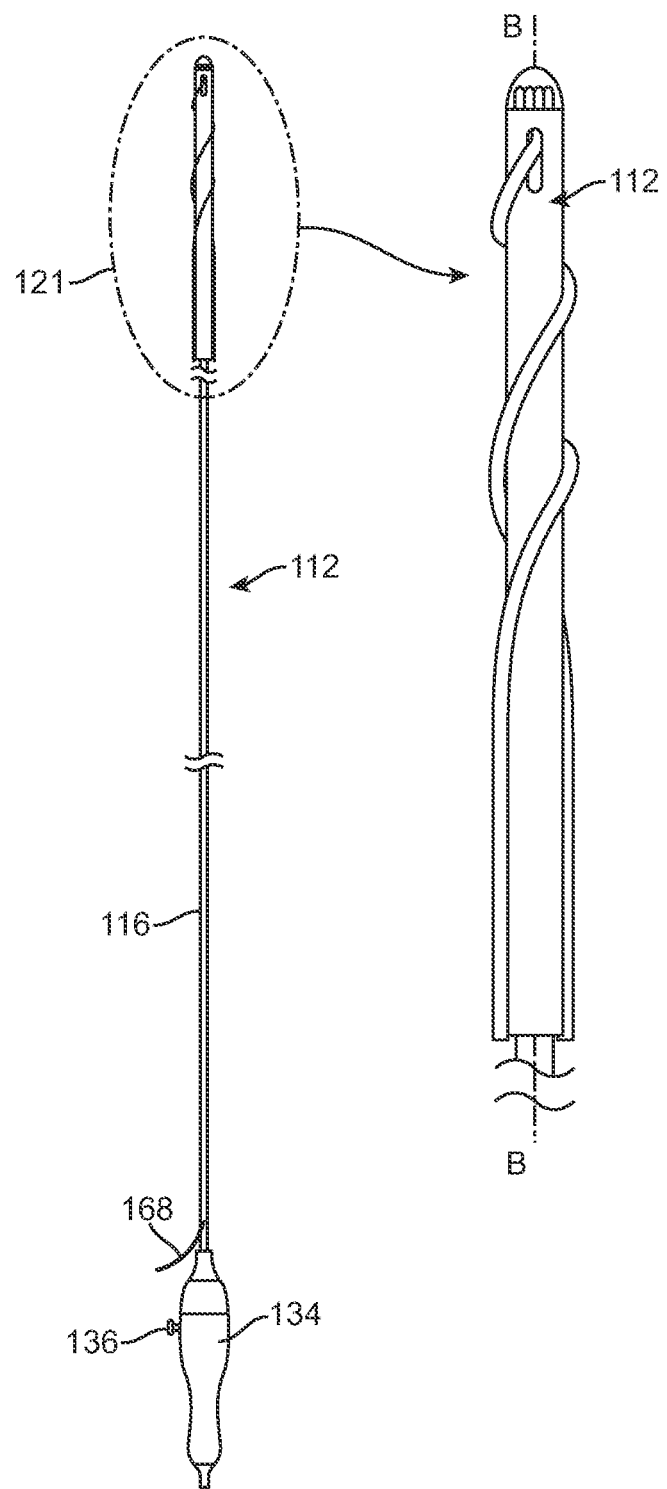
FIG. 5A is a profile view illustrating a treatment device including an elongated shaft having different mechanical and functional regions in accordance with an embodiment of the present technology.

FIG. 5A illustrates an embodiment of a treatment device 112 including an elongated shaft 116 having different mechanical and functional regions configured in accordance with an embodiment of the technology. The elongated shaft 116 of the treatment device 112, for example, includes a distal region with a therapeutic or treatment assembly 121 for delivery and deployment at a renal artery site for treatment and, in particular, for renal denervation. Disposed at a proximal end of the elongated shaft 116 is a handle assembly 134 for manipulation of the elongated shaft 116 and the therapeutic assembly 121. More specifically, the handle assembly 134 is configured with an actuator to provide for remote operation of a control member for controlling or transforming the therapeutic assembly 121 between a delivery state and a deployed state. Further details regarding suitable handle assemblies may be found, for example, in U.S. patent application Ser. No. 12/759,641, "Handle Assemblies for Intravascular Treatment Devices and Associated Systems and Methods" to Clark et al., which is incorporated herein by reference in its entirety.

The treatment device 112 is configured to deliver the therapeutic assembly 121 to a treatment site in a delivery (e.g., low-profile) state in which the assembly 121 is substantially linear (e.g., straight) such that the electrodes are collapsed and in contact with the distal electrode support section. The electrodes wind around the distal electrode support section with an axis that is substantially aligned with the axis of the distal electrode support section. Once located at the treatment site within the renal artery, the handle assembly 134 is operated for actuation of a control member that transforms the therapeutic assembly 121 from the delivery state to a deployed state. One end of the control wire may be affixed at or near the proximal end of the distal electrode support section, and the opposite end of the control wire may terminate within the handle assembly 134. The tension in the control wire 168 provides for a proximally and axially directed force that acts on the helical push wire electrodes. Under the influence of the tension force in the control wire 168 and the radial constraint of the patient's renal arterial wall, the electrodes expand, deploying into the helical geometry to create stable contact with the wall of the renal artery.

The control member 168 can be a control rod or wire that extends the axial length of the catheter device 112 from at or near the distal end of the electrode support section and/or the shaft to the handle assembly 134. The control wire 168 can comprise ultra high molecular weight (UHMW) fiber, such as, for example, high strength, gel-spun fiber sold under the trademark SPECTRA or other sufficiently strong polyethylene fiber. Alternatively, nitinol, a para-aramid synthetic fiber sold under the trademark KEVLAR, or other mono or multi filament types can be used provided that they are compatible with the application and can transfer the tensile force to the proximal end of the therapeutic assembly 121.

To provide for the desired expansion upon deployment, the distal electrode support section may be a tubular member 122. In various embodiments, the tubular support structure 122 may be electrically nonconductive. The tubular support structure 122 may be formed from biocompatible metals and/or polymers, including PET, polyamide, polyimide, polyethylene block amide copolymer, polypropylene, or PEEK polymers. Moreover, in some embodiments, the tubular support structure 122 may be formed, at least in part, from radiopaque materials that are capable of being imaged fluoroscopically to allow a clinician to determine if the tubular support structure 122 is appropriately placed and/or deployed in the renal artery. Radiopaque materials may include barium sulfate, bismuth trioxide, bismuth subcarbonate, powdered tungsten, powdered tantalum, or various formulations of certain metals, including gold, platinum, and platinum-iridium. These materials may be directly incorporated into the tubular support structure 122 or may form a partial or complete coating of the tubular support structure 122.

FIG. 5B is a perspective view of the treatment device 112 comprising helical push wire electrodes in a delivery state (e.g., low-profile or collapsed configuration) outside of a patient in accordance with an embodiment of the present technology, and FIG. 5C is a perspective view of the treatment device 112 comprising helical push wire electrodes in a deployed state (e.g., expanded configuration).

Referring to FIGS. 5B and 5C, the distal electrode support structure 122 comprises a tubular member having a central lumen to define a longitudinal axis B-B. In one embodiment, the cross sectional shape of the distal electrode support structure 122 can be a square cross section which may create a smaller profile allowing use with a smaller diameter catheter. In one embodiment, a portion of the distal support structure 122 is square and a portion of the distal support structure 122 is rounded. In another embodiment, the entire distal support structure 122 is square. The illustrated treatment device 112 comprises a shaft 125, one or more helical push wire electrodes 123, a distal electrode support section 122, and thermocouple wires 124. The shaft 125 is mounted to the distal electrode support section 122. A joint may be provided to couple the distal electrode support section 122 to the shaft 125, thereby providing the desired transfer of torque from the shaft 125 to the electrode support section 122 when navigating to the treatment site. More specifically, each end of the electrode support section 122 and the shaft 125 may respectively include mating notches that permit the ends of the tubular members to interlock. In some embodiments, disposed about the joint is a stainless steel sleeve that is crimped about the juncture to provide additional support to the joint. In various embodiments, the shaft 125 is fixed to the distal electrode support section 122 by adhesive, welding, crimping, over-molding, and/or soldering.

The shaft 125 and the distal electrode support section 122 may together define a lumen where the thermocouple wires 124 are disposed. The thermocouple wires 124 are disposed along or in parallel to the longitudinal axis B-B. In one embodiment, the thermocouple wires 124 may be fixed to the proximal end 122a of the distal electrode support section 122. In another embodiment, the thermocouple wires 124 may be fixed to the distal end 122b of the distal electrode support section 122.

In further embodiments, the helical push wire electrodes 123 may be coupled to the thermocouple wires 124 at the distal end 122b of the distal electrode support section 122. The helical push wire electrodes 123 and the thermocouple wires 124 may be coupled by soldering or a by mechanical lock. In one embodiment, the therapeutic assembly may comprise a cover 129 encasing the joint of the helical push wire electrodes and the thermocouple wires. The cover 129 may be made of various materials. In one embodiment, the cover 129 may be coated with Titanium Nitride (TiN). In further embodiments, the therapeutic assembly may comprise a temperature sensor, such as a thermometer. In one embodiment, the cover 129 encloses the temperature sensor. The cover 129 could also be used to electrically connect the supply wire to multiple wire electrodes (such as electrode 123). Accordingly, the same supply wire would also transmit temperature and impedance measurements. In embodiments with a single electrode (such as electrode 603 illustrated in FIG. 6A), the same supply wire may act as a TC wire which can transmit temperature and impedance.

In various embodiments, the helical push wire electrodes 123 are disposed within the lumen defined by the shaft 125. The treatment device 112 may further comprise sheaths 126 defining additional lumens where the helical push wire electrodes 123 are disposed. The electrodes 123 surrounded by the sheaths 126 are disposed in parallel to the longitudinal axis B-B. The helical push wire electrodes 123 wind around the distal electrode support section 122 and are axially and radially spaced from one another about the distal electrode support section 122. When in the delivery configuration, the helical push wire electrodes 123 are in contact with the distal electrode support section 122. When in the deployed configuration, the helical push wire electrodes 123 are expanded from the distal electrode support section 122. When delivered into the renal artery, the deployed helical push wire electrodes 123 are in contact with the inner wall of the renal artery.

The distal electrode support section 122 may comprise one or more slots 130. In various embodiments, the slots 130 may be adjacent to or in close proximity to the distal end of the distal electrode support section 122. The slots 130 may be evenly spaced along a circumference of the distal electrode support section 122. The slots 130 hold the distal portion 123b of the electrodes 123 close to the surface of the distal electrode support section 122 and may prevent the distal portion 123b of the electrodes 123 from buckling.

In various embodiments, the helical push wire electrodes 123 are retractable. The proximal ends 123c of the helical push wire electrodes 123 are retractable whereas the distal ends of the helical push wire 123 are fixed. Pushing the helical push wire 123 relative to the distal end of the therapeutic assembly places the electrodes 123 into the deployment configuration. When the electrode 122 is placed under compression, at least a portion of the electrode 122 (in the absence of any restriction in the radial direction) deflects from the substantially straight shape of FIG. 5B to form the substantial helical shape of FIG. 5C. Pulling the helical push wire 123 relative to the distal end of the therapeutic assembly places the electrodes 123 into the delivery configuration.

In some embodiments, fixing the distal ends of the electrodes can create a more stable structure as compared to electrodes having free-floating distal ends. Although, electrodes with free-floating distal ends may offer other advantages. The electrodes with fixed distal ends may provide a secure and steady contact with the inner wall of the renal artery when the electrodes are deployed. As both ends and the pitch of the helical structure are fixed, helixes of different diameters may be formed by adjusting the retractable end of the electrode 123. As such, therapeutic assemblies with helical push wire electrodes may be used in vessels of various sizes, where the inner wall of a renal artery constrains the size of the helix that the electrode 122 creates. The electrodes 123 wind around the distal electrode support section and provide a fixed number of windings. As such, the electrodes 123 form a set of intertwined helixes are formed. In one embodiment, a push rod (not shown) may be coupled to the proximal end of the electrode 123c for adjusting purposes. In various embodiments, as illustrated in FIG. 5C, the retractable end of the electrode 123 may be joined such that multiple electrodes 123 may be adjusted collectively and uniformly. In a further embodiment, a push rod may be coupled to the distal end of the electrodes 123 rather than the proximal end.

The proximal portions 123a of the electrodes may be surrounded by proximal sleeves 127. As illustrated in FIG. 5C, the proximal sleeves 127 may prevent the proximal portions 123a from buckling and forming a sharp curve when the electrodes 123 are in the deployed configuration. The proximal sleeves 127 may provide the proximal portions 123a of the electrodes 123 with a curve 130. In various embodiments, the proximal sleeves 127 are positioned to provide a curve 130 that is less than a predetermined value to prevent the electrodes 123 from forming sharp angles on the proximal portion. The proximal sleeves 127 may also provide a lubricated or low-friction lumen to allow the electrodes 123 to be pushed out of and retracted back into the sleeves. The distal portions 123b of the electrodes 123 may be further surrounded by distal sleeves 128, or in place of sleeves the distal portion 123b may be laminated or coated.

Further, as illustrated in FIG. 5B, the proximal sleeves 127 and the distal sleeves 128 may provide complete or near complete insulation of electrodes 123 when the therapeutic assembly is in the delivery configuration with helical push wire electrodes. Accordingly, the impedance of the deployed electrodes is reduced and more RF energy is delivered. In the illustrated example, the proximal sleeves 127 and the distal sleeves 128, or the proximal sleeves 127 and the distal coating or lamination on the electrode 123 have a spacing between them in the collapsed configuration. In other embodiments, the sleeves 127 and 128, or the proximal sleeves 127 and the distal coating may make contact or even overlap, that is, the distal sleeve 127 or lamination or coating may axially telescope within the lumen of the proximal sleeve 127. In the illustrated example, the electrodes 123 are round wires. In other embodiments, the electrodes 123 may be flat wires or wires of other geometries as previously described. In the case of flat wires, the electrodes 123 can be positioned such that when deployed, the flat surface is in contact with the inner wall of the renal artery. The fixed distal end 122b of the electrodes, the proximal sleeves 127 and the distal sleeves 128 may prevent the flat-wire electrodes from rotating and may ensure that the flat surface is in contact with the inner wall of the renal artery when the electrodes are deployed.

Referring to FIGS. 5E and 5F, the distal support section 122 may include helical grooves 132 on its surface. The helical grooves 132 can be configured to correspond to the electrodes 123, such that in the collapsed delivery configuration, the electrodes 123 are flush with (or at least partially recessed into) the surface of the distal support section 122. Accordingly, providing grooves can allow a smaller cross section in the collapsed delivery configuration. Further, the treatment device 112 can be provided with a smooth, low friction outer surface, which helps prevent the device from getting caught within the vessel when inserted into and retracted out of a guide catheter.

Therapeutic assemblies with helical push wire electrodes may provide variable power densities. In various embodiments, the wire may include different insulation levels along its length to create discrete lesions that consume different levels of electric power. The proximal portions 123a of the electrodes may be insulated. Although various sizes of helix may be formed in arteries of different sizes, because the proximal portions are insulated, the surface of the electrodes, when deployed, is fixed. Accordingly, the electric power consumption is unaffected by the artery size. A flat wire may be insulated on its inner surface to prevent RF energy dissipation in the bloodstream. Accordingly, the electrodes would deliver a greater percentage of power into the tissue.

The helical push wire electrode 123 is selectively transformable between the delivery state (FIG. 5B) and the deployed state (FIG. 5C) by application of a force having at least a proximally directed axial component and preferably applied at or near the proximal end 123a to transform the entire electrode 123. In one embodiment, an axial force applied at or near the proximal end 123a in the distal direction deflects the electrode 123 such that it forms the helically-shaped support structure shown in FIG. 5C, thus bringing one or more portions 123c of the electrodes 123 into contact with the inner wall of the renal artery.

Figure 5D:
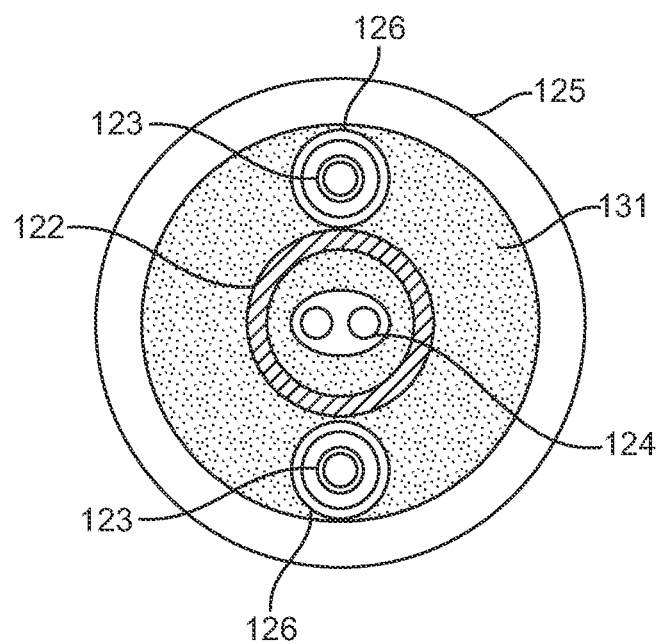
FIG. 5D is a cross-sectional end view illustrating the treatment device shown in FIG. 5A.

FIG. 5D is a cross sectional view of a treatment device 112 comprising helical push wire electrodes in accordance with an embodiment. In the illustrated example, the treatment device 112 comprises two electrodes 123 that are placed opposite of each other. The gap 131 defined by the shaft 125 and the distal electrode support section 126 may be filled with adhesives to maintain even distribution of the electrodes 123 about the central axis of the therapeutic assembly and to keep the portions of the electrodes enclosed therein stationary. As such, both ends of the helical structure formed by the electrodes 123 are fixed.

Figure 5G:
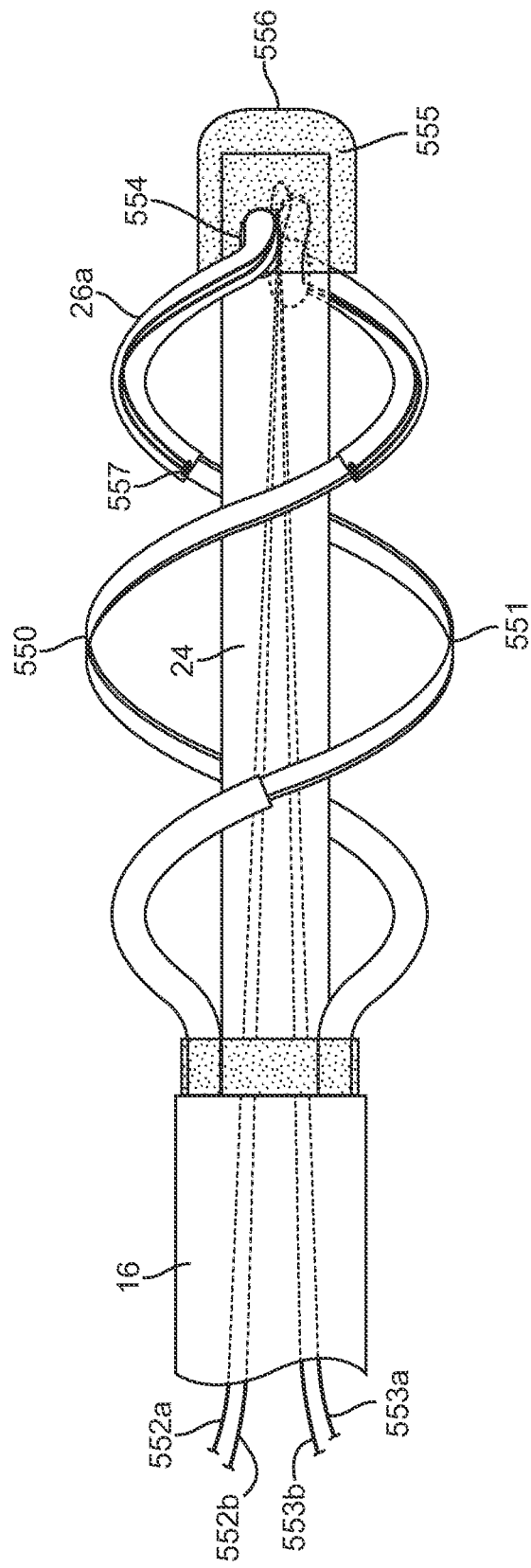
FIG. 5G is a profile view illustrating a therapeutic assembly including push wire electrodes in accordance with an embodiment of the present technology.

FIG. 5G illustrates an exemplary therapeutic assembly comprising push wire electrodes 550 and 551. In this embodiment, a separate TC/supply wire pair 552a-b, 553a-b is coupled to each push wire electrode 550, 551 respectively. In this manner, separate temperature measurements may be obtained and each push wire electrode 550 may be energized independently. One push wire electrode 550 coupled with TC/supply wire pair 552a-b will be described but it should be understood that this same configuration could apply to the other push wire electrode 551 (or any other push wire electrode 550 for an embodiment with a plurality of push wire electrodes).

The TC/supply wire pair 552a-b may run from the proximal end of the treatment device 12 (shown in FIG. 1) through a lumen in the elongated shaft 16 through a central lumen of the distal electrode support section 24 out the push wire electrode's distal exit port 554. The TC/supply wire pair 552a-b runs along the push wire electrode 550 itself, being routed across the inner (non-tissue contact) surface of the push wire electrode 550. The TC/supply wire pair 552a-b can be fixed to the push wire electrode 550 at an attachment point 557 near the end of the distal sleeve 26a. Alternatively, the TC/supply wire pair 552a-b can be routed within a lumen of the distal sleeve 26a and fixed to the distal sleeve 26a itself at its end (i.e. exit port of the push wire electrode 550).

The distal tip 556 of the push wire electrode 550 could be covered with adhesive 555 which protects the distal tip, configures the distal tip to be atraumatic, as well as secures the TC/supply wires 552a-b into place. As with previous embodiments, the TC/supply wire pair 552a-b could act as a wire to provide temperature and impedance measurements as well as supply RF energy. Alternatively, RF energy could be supplied to the distal tip with a separate RF supply wire and within the lumen of the catheter, provided the RF supply wire is electrically coupled to the push wire electrode 550.

In an alternative embodiment (not shown), a single TC/supply wire could be provided for a plurality of push wire electrodes. In this embodiment, the push wire electrodes would be electrically coupled within the distal tip thus energizing all push wire electrodes simultaneously. The distal point of attachment of the TC/supply wire to the push wire electrode would be the measurement point of temperature. For certain embodiments, a single temperature measurement on a single push wire electrode could be sufficient.

Accordingly, the TC wires 552a-b would be measuring the temperature of the push wire electrode 550 at a much closer proximity to tissue. In embodiments where the TC wire terminates at the distal tip of the treatment device, the temperature would read near the center of the artery lumen. Reading temperature farther from the target tissue site as well as exposing the tip to a greater amount of blood flow could provide a less accurate tissue temperature. giving more of an estimate of tissue temperature.

FIG. 6A is a perspective view of the treatment device comprising a helical push wire electrode in a delivery state in accordance with an embodiment. FIG. 6B is a perspective view of the treatment device comprising a helical push wire electrode in a deployed state in accordance with an embodiment. Similar to the multiple-electrode configuration illustrated in FIGS. 5B and 5C, the illustrated treatment device comprises a shaft 601, one helical push wire electrode 603, a distal electrode support section 602, and thermocouple wires 606. In one embodiment, the thermocouple wires 606 may be fixed to the distal end of the distal electrode support section 602 and coupled to the helical push wire electrode 603. The proximal end of the helical push wire electrode 603 is retractable whereas the distal end of the helical push wire 603 is fixed. Pushing the helical push wire 603 relative to the distal end of the therapeutic assembly places the electrodes 603 into the deployment configuration. When the electrode 602 is placed under tension, at least a portion of the electrode 602 (in the absence of any restriction in the radial direction) deflects from the substantially straight shape of FIG. 6A to form the substantial helical shape of FIG. 6B. Pulling the helical push wire 603 relative to the distal end of the therapeutic assembly places the electrodes 603 into the delivery configuration.

Figure 6C:
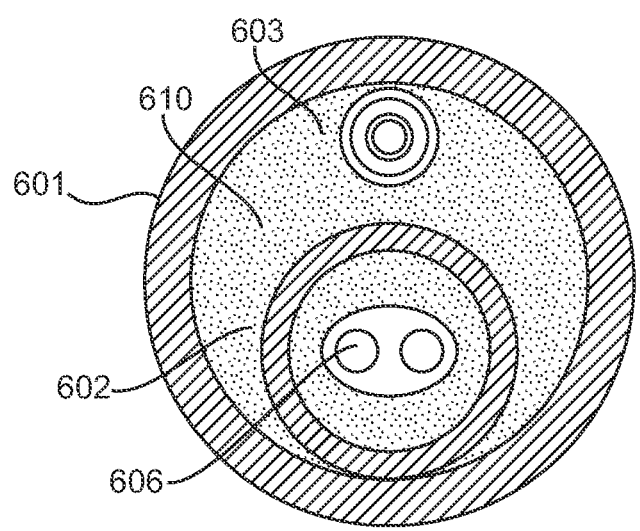
FIG. 6C is a cross-sectional end view of a treatment device including a helical push wire electrode in accordance with an embodiment of the present technology.

FIG. 6C is a cross sectional view of a treatment device comprising a helical push wire electrode in accordance with an embodiment. In the illustrated example, the treatment device comprise an electrode 603 that is placed within the lumen defined by the shaft 601. The gap 610 defined by the shaft 601 and the distal electrode support section 602 may be filled with adhesives to keep the portion of the electrode 603 enclosed therein stationary. As such, both ends of the helical structure formed by the electrode 603 are fixed.

IV. APPLYING ENERGY TO TISSUE VIA THE HELICAL PUSH WIRE ELECTRODE

Referring back to FIG. 1, the energy generator 26 may supply a continuous or pulsed RF electric field to the helical push wire electrode 22. The application of RF energy in pulses may allow the application of relatively higher energy levels (e.g., higher power), longer or shorter total duration times, and/or better controlled intravascular renal neuromodulation therapy. Pulsed energy may also allow for the use of a smaller electrode.

Although many of the embodiments described herein pertain to electrical systems configured for the delivery of RF energy, it is contemplated that the desired treatment may be accomplished by other means, e.g., by coherent or incoherent light; direct thermal modification (e.g., with a heated or cooled fluid or resistive heating element or cryogenic applicator); microwave; ultrasound (including high intensity focused ultrasound); diode laser; radiation; a tissue heating fluid; and/or a cryogenic refrigerant.

Energy delivery may be monitored and controlled via data collected with one or more sensors, such as temperature sensors (e.g., thermocouples, thermistors, etc.), impedance sensors, pressure sensors, optical sensors, flow sensors, chemical sensors, etc., which may be incorporated into or on the helical push wire electrode 22, the distal electrode support section 24, and/or in/on adjacent areas on the distal portion 20. A sensor may be incorporated into the helical push wire electrode 22 in a manner that specifies whether the sensor(s) are in contact with tissue at the treatment site and/or are facing blood flow. The ability to specify sensor placement relative to tissue and blood flow is highly significant, since a temperature gradient across the electrode from the side facing blood flow to the side in contact with the vessel wall may be up to about 15° C. Significant gradients across the electrode in other sensed data (e.g., flow, pressure, impedance, etc.) also are expected.

The sensor(s) may, for example, be incorporated on the side of one or more helical push wire electrode 22 that contact the vessel wall at the treatment site during power and energy delivery or may be incorporated on the opposing side of one or more helical push wire electrode 22 that face blood flow during energy delivery, and/or may be incorporated within certain regions of the helical push wire electrode 22 (e.g., distal, proximal, quadrants, etc.). In some embodiments, multiple sensors may be provided at multiple positions along the electrode or energy delivery element array and/or relative to blood flow. For example, a plurality of circumferentially and/or longitudinally spaced sensors may be provided. In one embodiment, a first sensor may contact the vessel wall during treatment, and a second sensor may face blood flow.

Additionally or alternatively, various microsensors may be used to acquire data corresponding to the helical push wire electrode 22, the vessel wall and/or the blood flowing across the helical push wire electrode 22. For example, arrays of micro thermocouples and/or impedance sensors may be implemented to acquire data along the helical push wire electrode 22 or other parts of the treatment device. Sensor data may be acquired or monitored prior to, simultaneously with, or after the delivery of energy or in between pulses of energy, when applicable. The monitored data may be used in a feedback loop to better control therapy, e.g., to determine whether to continue or stop treatment, and it may facilitate controlled delivery of an increased or reduced power or a longer or shorter duration therapy.

V. PERTINENT ANATOMY AND PHYSIOLOGY

The following discussion provides further details regarding pertinent patient anatomy and physiology. This section is intended to supplement and expand upon the previous discussion regarding the relevant anatomy and physiology, and to provide additional context regarding the disclosed technology and the therapeutic benefits associated with renal denervation. For example, as mentioned previously, several properties of the renal vasculature may inform the design of treatment devices and associated methods for achieving renal neuromodulation via intravascular access, and impose specific design requirements for such devices. Specific design requirements may include accessing the renal artery, facilitating stable contact between the energy delivery elements of such devices and a luminal surface or wall of the renal artery, and/or effectively modulating the renal nerves with the neuromodulatory apparatus.

A. The Sympathetic Nervous System

The Sympathetic Nervous System (SNS) is a branch of the autonomic nervous system along with the enteric nervous system and parasympathetic nervous system. It is always active at a basal level (called sympathetic tone) and becomes more active during times of stress. Like other parts of the nervous system, the sympathetic nervous system operates through a series of interconnected neurons. Sympathetic neurons are frequently considered part of the peripheral nervous system (PNS), although many lie within the central nervous system (CNS). Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation may elicit the release of adrenaline from the adrenal medulla.

Once released, norepinephrine and epinephrine bind adrenergic receptors on peripheral tissues. Binding to adrenergic receptors causes a neuronal and hormonal response. The physiologic manifestations include pupil dilation, increased heart rate, occasional vomiting, and increased blood pressure. Increased sweating is also seen due to binding of cholinergic receptors of the sweat glands.

The sympathetic nervous system is responsible for up- and down-regulating many homeostatic mechanisms in living organisms. Fibers from the SNS innervate tissues in almost every organ system, providing at least some regulatory function to things as diverse as pupil diameter, gut motility, and urinary output. This response is also known as sympathoadrenal response of the body, as the preganglionic sympathetic fibers that end in the adrenal medulla (but also all other sympathetic fibers) secrete acetylcholine, which activates the secretion of adrenaline (epinephrine) and to a lesser extent noradrenaline (norepinephrine). Therefore, this response that acts primarily on the cardiovascular system is mediated directly via impulses transmitted through the sympathetic nervous system and indirectly via catecholamines secreted from the adrenal medulla.

Science typically looks at the SNS as an automatic regulation system, that is, one that operates without the intervention of conscious thought. Some evolutionary theorists suggest that the sympathetic nervous system operated in early organisms to maintain survival as the sympathetic nervous system is responsible for priming the body for action. One example of this priming is in the moments before waking, in which sympathetic outflow spontaneously increases in preparation for action.

1. The Sympathetic Chain

Figure 7:
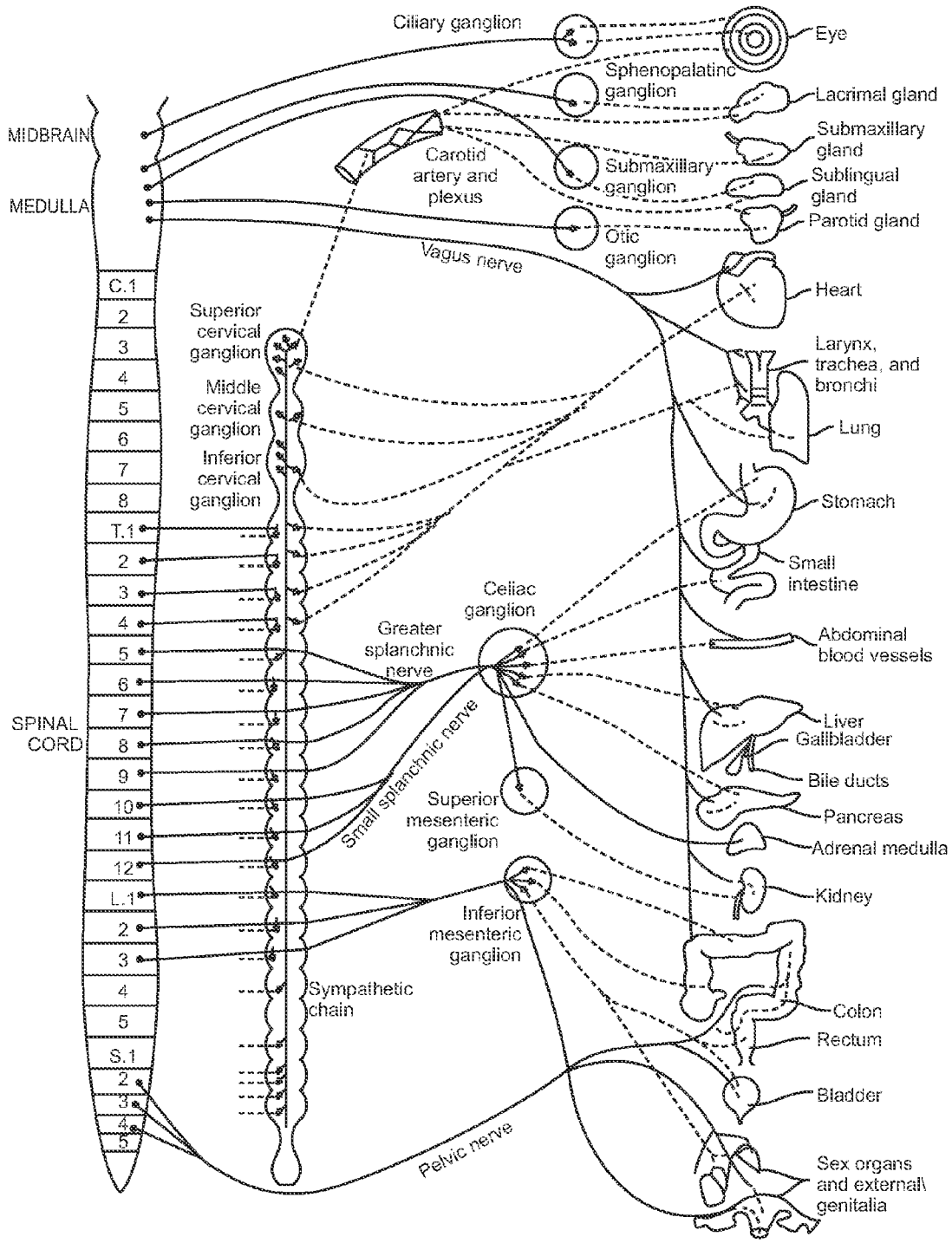
FIG. 7 is a conceptual illustration of the sympathetic nervous system (SNS) and how the brain communicates with the body via the SNS.

As shown in FIG. 7, the SNS provides a network of nerves that allows the brain to communicate with the body. Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Axons of these nerves leave the spinal cord through the anterior rootlet/root. They pass near the spinal (sensory) ganglion, where they enter the anterior rami of the spinal nerves. However, unlike somatic innervation, they quickly separate out through white rami connectors which connect to either the paravertebral (which lie near the vertebral column) or prevertebral (which lie near the aortic bifurcation) ganglia extending alongside the spinal column.

In order to reach the target organs and glands, the axons should travel long distances in the body, and, to accomplish this, many axons relay their message to a second cell through synaptic transmission. The ends of the axons link across a space, the synapse, to the dendrites of the second cell. The first cell (the presynaptic cell) sends a neurotransmitter across the synaptic cleft where it activates the second cell (the postsynaptic cell). The message is then carried to the final destination.

In the SNS and other components of the peripheral nervous system, these synapses are made at sites called ganglia. The cell that sends its fiber is called a preganglionic cell, while the cell whose fiber leaves the ganglion is called a postganglionic cell. As mentioned previously, the preganglionic cells of the SNS are located between the first thoracic (T1) segment and third lumbar (L3) segments of the spinal cord. Postganglionic cells have their cell bodies in the ganglia and send their axons to target organs or glands.

The ganglia include not just the sympathetic trunks but also the cervical ganglia (superior, middle and inferior), which sends sympathetic nerve fibers to the head and thorax organs, and the celiac and mesenteric ganglia (which send sympathetic fibers to the gut).

2. Innervation of the Kidneys

Figure 8:
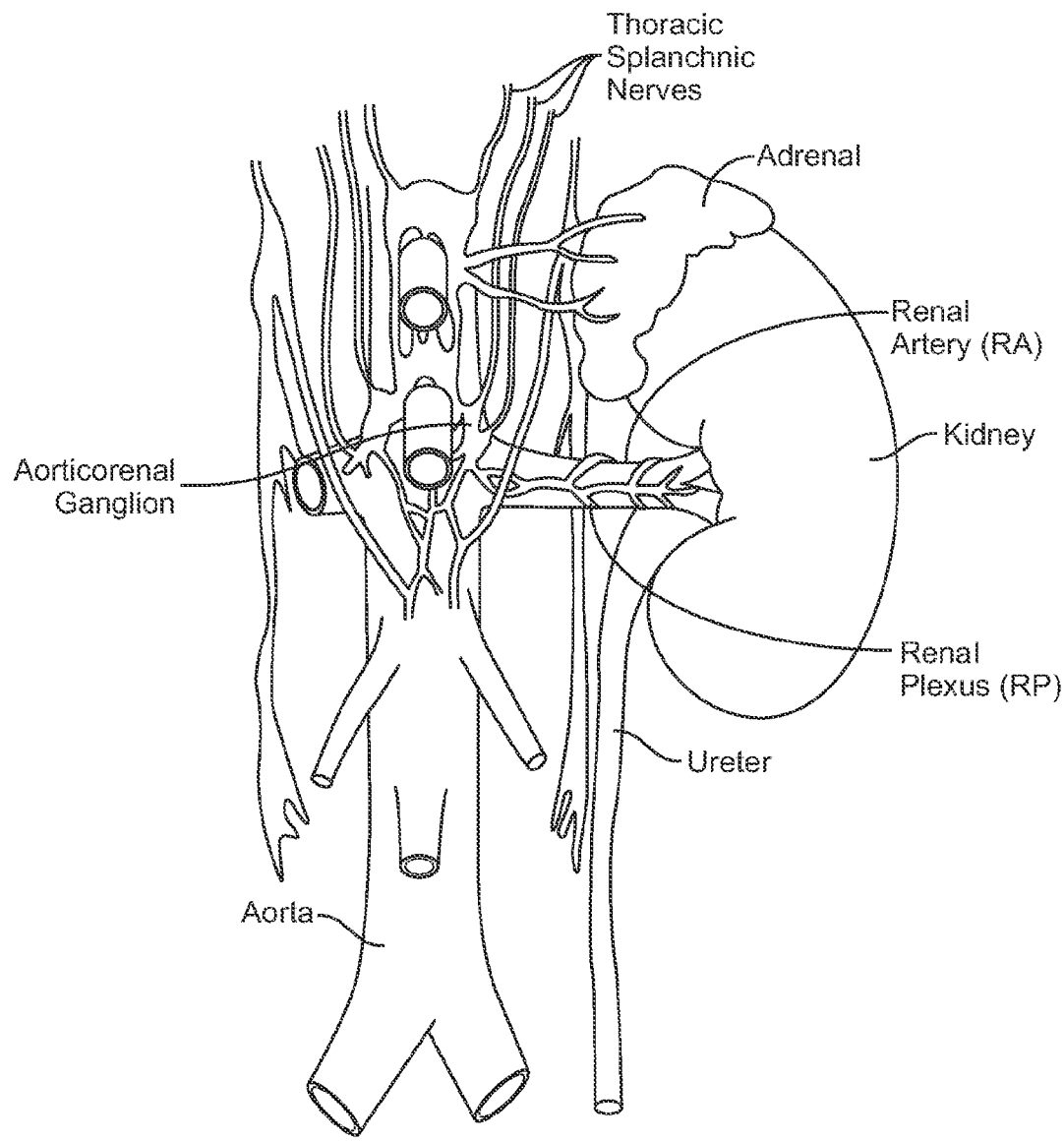
FIG. 8 is an anatomical view of nerves innervating a left kidney to form the renal plexus surrounding a left renal artery.

As shown in FIG. 8, the kidney is innervated by the renal plexus (RP), which is intimately associated with the renal artery. The renal plexus (RP) is an autonomic plexus that surrounds the renal artery and is embedded within the adventitia of the renal artery. The renal plexus (RP) extends along the renal artery until it arrives at the substance of the kidney. Fibers contributing to the renal plexus (RP) arise from the celiac ganglion, the superior mesenteric ganglion, the aorticorenal ganglion and the aortic plexus. The renal plexus (RP), also referred to as the renal nerve, is predominantly comprised of sympathetic components. There is no (or at least very minimal) parasympathetic innervation of the kidney.

Preganglionic neuronal cell bodies are located in the intermediolateral cell column of the spinal cord. Preganglionic axons pass through the paravertebral ganglia (they do not synapse) to become the lesser splanchnic nerve, the least splanchnic nerve, first lumbar splanchnic nerve, second lumbar splanchnic nerve, and travel to the celiac ganglion, the superior mesenteric ganglion, and the aorticorenal ganglion. Postganglionic neuronal cell bodies exit the celiac ganglion, the superior mesenteric ganglion, and the aorticorenal ganglion to the renal plexus (RP) and are distributed to the renal vasculature.

3. Renal Sympathetic Neural Activity

Messages travel through the SNS in a bidirectional flow. Efferent messages may trigger changes in different parts of the body simultaneously. For example, the sympathetic nervous system may accelerate heart rate; widen bronchial passages; decrease motility (movement) of the large intestine; constrict blood vessels; increase peristalsis in the esophagus; cause pupil dilation, piloerection (goose bumps) and perspiration (sweating); and raise blood pressure. Afferent messages carry signals from various organs and sensory receptors in the body to other organs and, particularly, the brain.

Hypertension, heart failure and chronic kidney disease are a few of many disease states that result from chronic activation of the SNS, especially the renal sympathetic nervous system. Chronic activation of the SNS is a maladaptive response that drives the progression of these disease states. Pharmaceutical management of the renin-angiotensin-aldosterone system (RAAS) has been a longstanding, but somewhat ineffective, approach for reducing over-activity of the SNS.

As mentioned above, the renal sympathetic nervous system has been identified as a major contributor to the complex pathophysiology of hypertension, states of volume overload (such as heart failure), and progressive renal disease, both experimentally and in humans. Studies employing radiotracer dilution methodology to measure overflow of norepinephrine from the kidneys to plasma revealed increased renal norepinephrine (NE) spillover rates in patients with essential hypertension, particularly so in young hypertensive subjects, which in concert with increased NE spillover from the heart, is consistent with the hemodynamic profile typically seen in early hypertension and characterized by an increased heart rate, cardiac output, and renovascular resistance. It is now known that essential hypertension is commonly neurogenic, often accompanied by pronounced sympathetic nervous system overactivity.

Activation of cardiorenal sympathetic nerve activity is even more pronounced in heart failure, as demonstrated by an exaggerated increase of NE overflow from the heart and the kidneys to plasma in this patient group. In line with this notion is the recent demonstration of a strong negative predictive value of renal sympathetic activation on all-cause mortality and heart transplantation in patients with congestive heart failure, which is independent of overall sympathetic activity, glomerular filtration rate, and left ventricular ejection fraction. These findings support the notion that treatment regimens that are designed to reduce renal sympathetic stimulation have the potential to improve survival in patients with heart failure.

Both chronic and end stage renal disease are characterized by heightened sympathetic nervous activation. In patients with end stage renal disease, plasma levels of norepinephrine above the median have been demonstrated to be predictive for both all-cause death and death from cardiovascular disease. This is also true for patients suffering from diabetic or contrast nephropathy. There is compelling evidence suggesting that sensory afferent signals originating from the diseased kidneys are major contributors to initiating and sustaining elevated central sympathetic outflow in this patient group; this facilitates the occurrence of the well known adverse consequences of chronic sympathetic over activity, such as hypertension, left ventricular hypertrophy, ventricular arrhythmias, sudden cardiac death, insulin resistance, diabetes, and metabolic syndrome.

(i) Renal Sympathetic Efferent Activity

Sympathetic nerves to the kidneys terminate in the blood vessels, the juxtaglomerular apparatus and the renal tubules. Stimulation of the renal sympathetic nerves causes increased renin release, increased sodium (Na+) reabsorption, and a reduction of renal blood flow. These components of the neural regulation of renal function are considerably stimulated in disease states characterized by heightened sympathetic tone and clearly contribute to the rise in blood pressure in hypertensive patients. The reduction of renal blood flow and glomerular filtration rate as a result of renal sympathetic efferent stimulation is likely a cornerstone of the loss of renal function in cardio-renal syndrome, which is renal dysfunction as a progressive complication of chronic heart failure, with a clinical course that typically fluctuates with the patient's clinical status and treatment. Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release) and diuretics (intended to counter the renal sympathetic mediated sodium and water retention).

However, the current pharmacologic strategies have significant limitations including limited efficacy, compliance issues, side effects and others.

(ii) Renal Sensory Afferent Nerve Activity

Figure 9A:
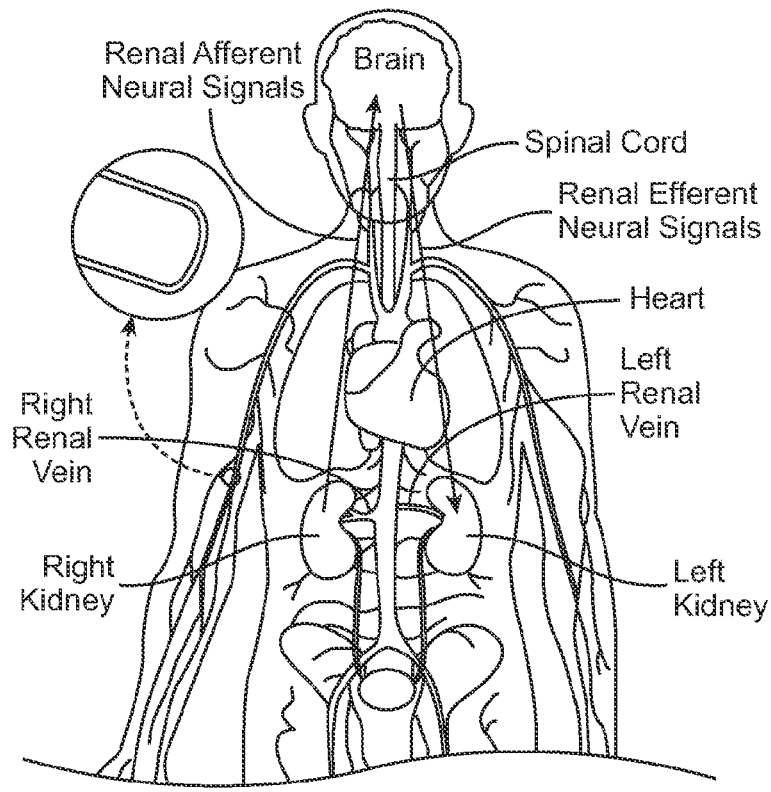
FIGS. 9A and 9B are anatomical and conceptual views, respectively, illustrating neural efferent and afferent communication between the brain and kidneys.
Figure 9B:
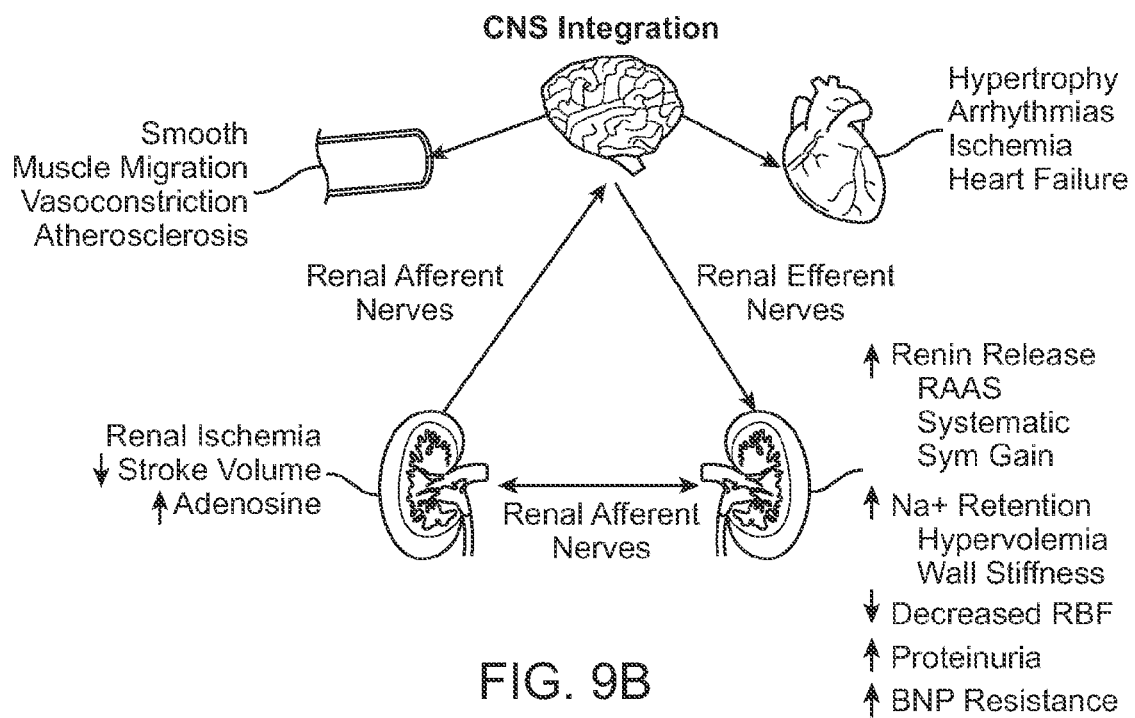

The kidneys communicate with integral structures in the central nervous system via renal sensory afferent nerves. Several forms of "renal injury" may induce activation of sensory afferent signals. For example, renal ischemia, reduction in stroke volume or renal blood flow, or an abundance of adenosine enzyme may trigger activation of afferent neural communication. As shown in FIGS. 9A and 9B, this afferent communication might be from the kidney to the brain or might be from one kidney to the other kidney (via the central nervous system). These afferent signals are centrally integrated and may result in increased sympathetic outflow. This sympathetic drive is directed towards the kidneys, thereby activating the RAAS and inducing increased renin secretion, sodium retention, volume retention and vasoconstriction. Central sympathetic over activity also impacts other organs and bodily structures innervated by sympathetic nerves such as the heart and the peripheral vasculature, resulting in the described adverse effects of sympathetic activation, several aspects of which also contribute to the rise in blood pressure.

The physiology therefore suggests that (i) modulation of tissue with efferent sympathetic nerves will reduce inappropriate renin release, salt retention, and reduction of renal blood flow, and that (ii) modulation of tissue with afferent sensory nerves will reduce the systemic contribution to hypertension and other disease states associated with increased central sympathetic tone through its direct effect on the posterior hypothalamus as well as the contralateral kidney. In addition to the central hypotensive effects of afferent renal denervation, a desirable reduction of central sympathetic outflow to various other sympathetically innervated organs such as the heart and the vasculature is anticipated.

B. Additional Clinical Benefits of Renal Denervation

As provided above, renal denervation is likely to be valuable in the treatment of several clinical conditions characterized by increased overall and particularly renal sympathetic activity such as hypertension, metabolic syndrome, insulin resistance, diabetes, left ventricular hypertrophy, chronic end stage renal disease, inappropriate fluid retention in heart failure, cardio-renal syndrome, and sudden death. Since the reduction of afferent neural signals contributes to the systemic reduction of sympathetic tone/drive, renal denervation might also be useful in treating other conditions associated with systemic sympathetic hyperactivity. Accordingly, renal denervation may also benefit other organs and bodily structures innervated by sympathetic nerves, including those identified in FIG. 7. For example, as previously discussed, a reduction in central sympathetic drive may reduce the insulin resistance that afflicts people with metabolic syndrome and Type II diabetics. Additionally, patients with osteoporosis are also sympathetically activated and might also benefit from the down regulation of sympathetic drive that accompanies renal denervation.

C. Achieving Intravascular Access to the Renal Artery

Figure 10A:
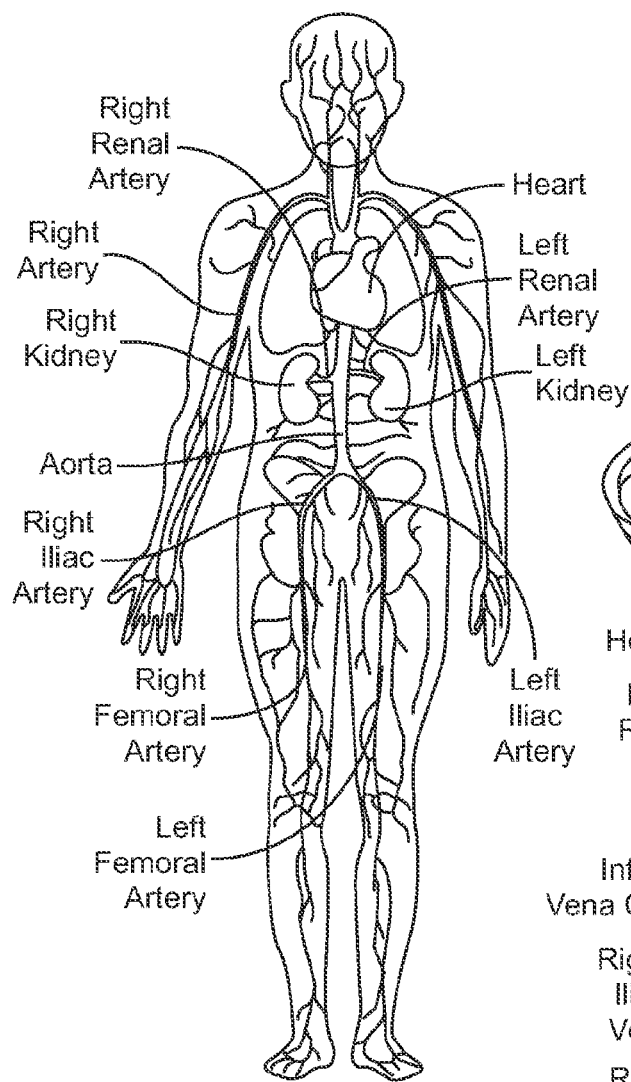
FIGS. 10A and 10B are anatomical views of the arterial vasculature and venous vasculature, respectively, of a human.

In accordance with the present technology, neuromodulation of a left and/or right renal plexus (RP), which is intimately associated with a left and/or right renal artery, may be achieved through intravascular access. As FIG. 10A shows, blood moved by contractions of the heart is conveyed from the left ventricle of the heart by the aorta. The aorta descends through the thorax and branches into the left and right renal arteries. Below the renal arteries, the aorta bifurcates at the left and right iliac arteries. The left and right iliac arteries descend, respectively, through the left and right legs and join the left and right femoral arteries.

Figure 10B:
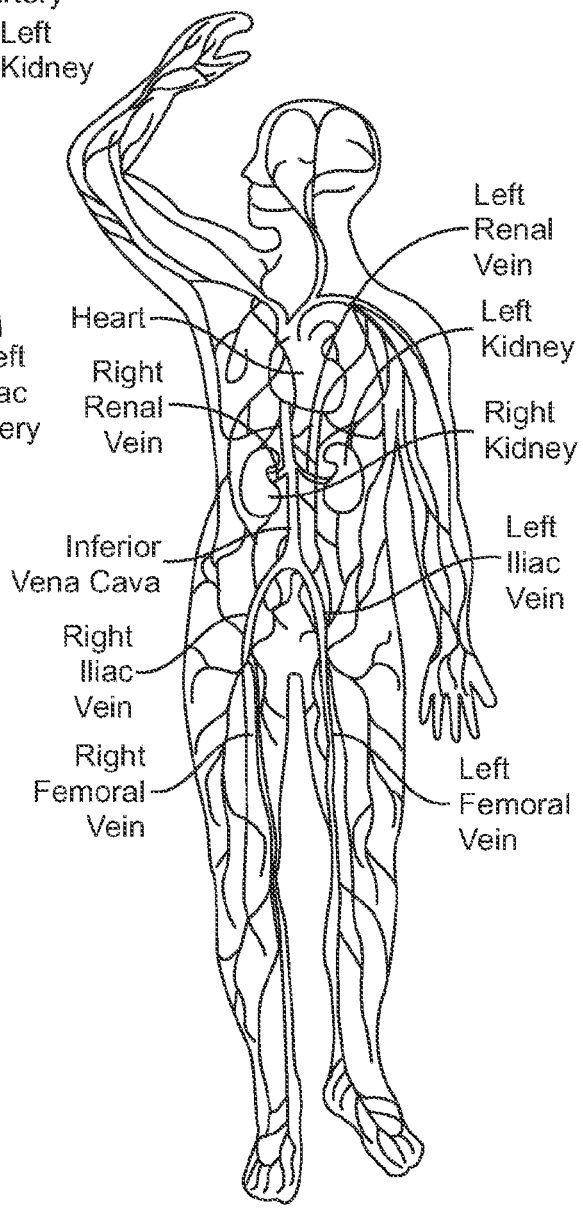

As FIG. 10B shows, the blood collects in veins and returns to the heart, through the femoral veins into the iliac veins and into the inferior vena cava. The inferior vena cava branches into the left and right renal veins. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed into the left atrium. From the left atrium, the oxygenated blood is conveyed by the left ventricle back to the aorta.

As will be described in greater detail later, the femoral artery may be accessed and cannulated at the base of the femoral triangle just inferior to the midpoint of the inguinal ligament. A catheter may be inserted percutaneously into the femoral artery through this access site, passed through the iliac artery and aorta, and placed into either the left or right renal artery. This comprises an intravascular path that offers minimally invasive access to a respective renal artery and/or other renal blood vessels.

The wrist, upper arm, and shoulder region provide other locations for introduction of catheters into the arterial system. For example, catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the renal arteries using standard angiographic technique.

D. Properties and Characteristics of the Renal Vasculature

Since neuromodulation of a left and/or right renal plexus (RP) may be achieved in accordance with the present technology through intravascular access, properties and characteristics of the renal vasculature may impose constraints upon and/or inform the design of apparatus, systems, and methods for achieving such renal neuromodulation. Some of these properties and characteristics may vary across the patient population and/or within a specific patient across time, as well as in response to disease states, such as hypertension, chronic kidney disease, vascular disease, end-stage renal disease, insulin resistance, diabetes, metabolic syndrome, etc. These properties and characteristics, as explained herein, may have bearing on the efficacy of the procedure and the specific design of the intravascular device. Properties of interest may include, for example, material/mechanical, spatial, fluid dynamic/hemodynamic and/or thermodynamic properties.

As discussed previously, a catheter may be advanced percutaneously into either the left or right renal artery via a minimally invasive intravascular path. However, minimally invasive renal arterial access may be challenging, for example, because as compared to some other arteries that are routinely accessed using catheters, the renal arteries are often extremely tortuous, may be of relatively small diameter, and/or may be of relatively short length. Furthermore, renal arterial atherosclerosis is common in many patients, particularly those with cardiovascular disease. Renal arterial anatomy also may vary significantly from patient to patient, which further complicates minimally invasive access. Significant inter-patient variation may be seen, for example, in relative tortuosity, diameter, length, and/or atherosclerotic plaque burden, as well as in the take-off angle at which a renal artery branches from the aorta. Apparatus, systems and methods for achieving renal neuromodulation via intravascular access should account for these and other aspects of renal arterial anatomy and its variation across the patient population when minimally invasively accessing a renal artery.

In addition to complicating renal arterial access, specifics of the renal anatomy also complicate establishment of stable contact between neuromodulatory apparatus and a luminal surface or wall of a renal artery. When the neuromodulatory apparatus includes an energy delivery element, such as an electrode, consistent positioning and appropriate contact force applied by the energy delivery element to the vessel wall are important for predictability. However, navigation is impeded by the tight space within a renal artery, as well as tortuosity of the artery. Furthermore, establishing consistent contact is complicated by patient movement, respiration, and/or the cardiac cycle because these factors may cause significant movement of the renal artery relative to the aorta, and the cardiac cycle may transiently distend the renal artery (i.e., cause the wall of the artery to pulse).

Even after accessing a renal artery and facilitating stable contact between neuromodulatory apparatus and a luminal surface of the artery, nerves in and around the adventia of the artery should be safely modulated via the neuromodulatory apparatus. Effectively applying thermal treatment from within a renal artery is non-trivial given the potential clinical complications associated with such treatment. For example, the intima and media of the renal artery are highly vulnerable to thermal injury. As discussed in greater detail below, the intima-media thickness separating the vessel lumen from its adventitia means that target renal nerves may be multiple millimeters distant from the luminal surface of the artery. Sufficient energy should be delivered to or heat removed from the target renal nerves to modulate the target renal nerves without excessively cooling or heating the vessel wall to the extent that the wall is frozen, desiccated, or otherwise potentially affected to an undesirable extent. A potential clinical complication associated with excessive heating is thrombus formation from coagulating blood flowing through the artery. Given that this thrombus may cause a kidney infarct, thereby causing irreversible damage to the kidney, thermal treatment from within the renal artery should be applied carefully. Accordingly, the complex fluid mechanics and thermodynamic conditions present in the renal artery during treatment, particularly those that may impact heat transfer dynamics at the treatment site, may be important in applying energy (e.g., heating thermal energy) and/or removing heat from the tissue (e.g., cooling thermal conditions) from within the renal artery.

The neuromodulatory apparatus should also be configured to allow for adjustable positioning and repositioning of the energy delivery element within the renal artery since location of treatment may also impact clinical efficacy. For example, it may be tempting to apply a full circumferential treatment from within the renal artery given that the renal nerves may be spaced circumferentially around a renal artery. In some situations, full-circle lesion likely resulting from a continuous circumferential treatment may be potentially related to renal artery stenosis. Therefore, the formation of more complex lesions along a longitudinal dimension of the renal artery via the mesh structures described herein and/or repositioning of the neuromodulatory apparatus to multiple treatment locations may be desirable. It should be noted, however, that a benefit of creating a circumferential ablation may outweigh the potential of renal artery stenosis or the risk may be mitigated with certain embodiments or in certain patients and creating a circumferential ablation could be a goal. Additionally, variable positioning and repositioning of the neuromodulatory apparatus may prove to be useful in circumstances where the renal artery is particularly tortuous or where there are proximal branch vessels off the renal artery main vessel, making treatment in certain locations challenging. Manipulation of a device in a renal artery should also consider mechanical injury imposed by the device on the renal artery. Motion of a device in an artery, for example by inserting, manipulating, negotiating bends and so forth, may contribute to dissection, perforation, denuding intima, or disrupting the interior elastic lamina.

Blood flow through a renal artery may be temporarily occluded for a short time with minimal or no complications. However, occlusion for a significant amount of time should be avoided to prevent injury to the kidney such as ischemia. It could be beneficial to avoid occlusion all together or, if occlusion is beneficial to the embodiment, to limit the duration of occlusion, for example to 2-5 minutes.

Based on the above described challenges of (1) renal artery intervention, (2) consistent and stable placement of the treatment element against the vessel wall, (3) effective application of treatment across the vessel wall, (4) positioning and potentially repositioning the treatment apparatus to allow for multiple treatment locations, and (5) avoiding or limiting duration of blood flow occlusion, various independent and dependent properties of the renal vasculature that may be of interest include, for example, (a) vessel diameter, vessel length, intima-media thickness, coefficient of friction, and tortuosity; (b) distensibility, stiffness and modulus of elasticity of the vessel wall; (c) peak systolic, end-diastolic blood flow velocity, as well as the mean systolic-diastolic peak blood flow velocity, and mean/max volumetric blood flow rate; (d) specific heat capacity of blood and/or of the vessel wall, thermal conductivity of blood and/or of the vessel wall, and/or thermal convectivity of blood flow past a vessel wall treatment site and/or radiative heat transfer; (e) renal artery motion relative to the aorta induced by respiration, patient movement, and/or blood flow pulsatility; and (f) the take-off angle of a renal artery relative to the aorta and tortuous renal arteries. These properties will be discussed in greater detail with respect to the renal arteries. However, dependent on the apparatus, systems and methods utilized to achieve renal neuromodulation, such properties of the renal arteries, also may guide and/or constrain design characteristics.

As noted above, an apparatus positioned within a renal artery should conform to the geometry of the artery. Renal artery vessel diameter, DRA, typically is in a range of about 2-10 mm, with most of the patient population having a DRA of about 4 mm to about 8 mm and an average of about 6 mm. Renal artery vessel length, LRA, between its ostium at the aorta/renal artery juncture and its distal branchings, generally is in a range of about 5-70 mm, and a significant portion of the patient population is in a range of about 20-50 mm. Since the target renal plexus is embedded within the adventitia of the renal artery, the composite Intima-Media Thickness, IMT, (i.e., the radial outward distance from the artery's luminal surface to the adventitia containing target neural structures) also is notable and generally is in a range of about 0.5-2.5 mm, with an average of about 1.5 mm. Although a certain depth of treatment is important to reach the target neural fibers, the treatment should not be too deep (e.g., >5 mm from inner wall of the renal artery) to avoid non-target tissue and anatomical structures such as the renal vein.

An additional property of the renal artery that may be of interest is the degree of renal motion relative to the aorta, induced by respiration and/or blood flow pulsatility. A patient's kidney, which located at the distal end of the renal artery, may move as much as 4" cranially with respiratory excursion. This may impart significant motion to the renal artery connecting the aorta and the kidney, thereby requiring from the neuromodulatory apparatus a unique balance of stiffness and flexibility to maintain contact between the thermal treatment element and the vessel wall during cycles of respiration. Furthermore, the take-off angle between the renal artery and the aorta may vary significantly between patients, and also may vary dynamically within a patient, e.g., due to kidney motion. The take-off angle generally may be in a range of about 30 degrees-135 degrees.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus, the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus, the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A catheter comprising:
   an elongate shaft having proximal and distal ends and a lumen extending proximally therethrough from an exit point at the distal end;
   a support structure extending distally a fixed distance from the shaft distal end, the shaft being configured to deliver the support structure to a treatment site within a vessel of a human patient; and
   a wire electrode slidably disposed within the shaft lumen and having a helical portion extending through the exit point and wrapped around the support structure to terminate in a fixed attachment at a distal end of the support structure, the helical portion being configured to modulate one or more nerves within tissue at or otherwise proximate to a wall of the vessel;
   wherein the wire electrode is adapted to be pushed distally through the exit point to cause radial expansion of the helical portion about the support structure, and the wire electrode is further adapted to be withdrawn proximally through the exit point to cause radial collapse of the helical portion about the support structure.

2. The catheter of claim 1 wherein:
   the wire electrode is a first wire electrode, the helical portion is a first helical portion, and the fixed attachment is a first fixed attachment; and
   the catheter further comprises a second wire electrode slidably disposed within the shaft lumen and having a second helical portion extending through the exit point and wrapped around the support structure to terminate in a second fixed attachment at the distal end of the support structure, the second helical portion being configured to modulate one or more nerves within tissue at or otherwise proximate to a wall of the vessel, wherein the first and second helical portions are intertwined;
   wherein the second wire electrode is adapted to be pushed distally through the exit point to cause radial expansion of the second helical portion about the support structure, and the second wire electrode is further adapted to be withdrawn proximally through the exit point to cause radial collapse of the second helical portion about the support structure.

3. The catheter of claim 2 wherein the first and second wire electrodes are each surrounded by a distal sleeve or coating extending proximally from the fixed attachment.

4. The catheter of claim 2 wherein the first and second wire electrodes are each surrounded by a slidable proximal sleeve extending distally from the exit point.

5. The catheter of claim 4 wherein the proximal sleeves are configured to guide the first and second wire electrodes through the exit point.

6. The catheter of claim 5 wherein the proximal sleeves are configured to prevent the first and second wire electrodes from buckling and/or forming a sharp angle while distally or proximally sliding through the exit point.

7. The catheter of claim 4 wherein the proximal sleeves are electrically insulative.

8. The catheter of claim 4 wherein the proximal sleeves are more flexible than the catheter shaft and less flexible than the first and second wire electrodes.

9. The catheter of claim 2 wherein the radial expansion transforms the first and second helical portions from a delivery state to a deployed state and wherein the first and second helical portions in the deployed state each have an inconsistent helical diameter.

10. The catheter of claim 1 wherein a transverse cross section of the wire electrode at the helical portion is not round.

11. The catheter of claim 10 wherein the transverse cross section has a greater width than height, the height being perpendicular to a longitudinal axis of the support structure.

12. The catheter of claim 10 wherein the helical portion has a first flat surface facing away from the support structure, a second flat surface facing toward the support structure, a first edge extending along one side of the wire electrode between the first and second flat surfaces, and a second edge extending along an opposite side of the wire electrode between the first and second flat surfaces.

* * * * *